(12) United States Patent
Damiano et al.

(10) Patent No.: US 12,195,542 B2
(45) Date of Patent: Jan. 14, 2025

(54) ANTIBODIES DIRECTED TO TIE-2 AND METHODS OF USE

(71) Applicant: Unity Biotechnology, Inc., South San Francisco, CA (US)

(72) Inventors: Jason Damiano, South San Francisco, CA (US); Kristina Oresic Bender, South San Francisco, CA (US); Richard Theolis, South San Francisco, CA (US); Deepika Bhatnagar, South San Francisco, CA (US); Nina Ly, South San Francisco, CA (US)

(73) Assignee: Unity Biotechnology, Inc., South San Francisco, CA (US)

( * ) Notice: Subject to any disclaimer, the term of this patent is extended or adjusted under 35 U.S.C. 154(b) by 234 days.

(21) Appl. No.: 16/953,165

(22) Filed: Nov. 19, 2020

(65) Prior Publication Data
US 2021/0155697 A1    May 27, 2021

Related U.S. Application Data

(60) Provisional application No. 62/938,816, filed on Nov. 21, 2019.

(51) Int. Cl.
| | |
|---|---|
| C07K 16/28 | (2006.01) |
| A61K 31/713 | (2006.01) |
| A61P 27/02 | (2006.01) |
| C12N 5/10 | (2006.01) |
| C12N 15/63 | (2006.01) |

(52) U.S. Cl.
CPC ........ *C07K 16/2863* (2013.01); *A61K 31/713* (2013.01); *A61P 27/02* (2018.01); *C12N 5/10* (2013.01); *C12N 15/63* (2013.01); *C07K 2317/21* (2013.01); *C07K 2317/31* (2013.01); *C07K 2317/33* (2013.01); *C07K 2317/60* (2013.01); *C07K 2317/622* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,811,785 B2 * | 10/2010 | Fuh | ........................ A61P 25/00 435/71.1 |
| 9,017,670 B2 | 4/2015 | Thurston | |
| 9,382,333 B2 | 7/2016 | Pajuelo et al. | |
| 2003/0040044 A1 | 2/2003 | Heavner et al. | |
| 2010/0021466 A1 | 1/2010 | Granger et al. | |
| 2011/0223615 A1 | 9/2011 | Lewis et al. | |
| 2011/0236411 A1 | 9/2011 | Scholler et al. | |
| 2015/0023979 A1 | 1/2015 | Kuhne | |
| 2016/0024195 A1 | 1/2016 | Economides et al. | |
| 2016/0289314 A1 * | 10/2016 | Shandilya | .............. C07K 16/22 |
| 2017/0165366 A1 | 6/2017 | Hicklin et al. | |
| 2017/0174789 A1 | 6/2017 | Thurston | |
| 2018/0105600 A1 | 4/2018 | Pons et al. | |
| 2018/0155422 A1 | 6/2018 | Bhatt et al. | |
| 2019/0002581 A1 | 1/2019 | Stafford et al. | |
| 2019/0194335 A1 | 6/2019 | Pfizer et al. | |

FOREIGN PATENT DOCUMENTS

| | | |
|---|---|---|
| WO | WO 1995021866 | 8/1995 |
| WO | WO 2000018804 | 4/2000 |
| WO | WO 2006/103100 | 10/2006 |

* cited by examiner

*Primary Examiner* — Marianne P Allen
(74) *Attorney, Agent, or Firm* — Rudy J. Ng; Bozicevic, Field & Francis LLP

(57) ABSTRACT

The invention relates to anti-Tie2 antibodies and methods of using the same.

18 Claims, 19 Drawing Sheets
Specification includes a Sequence Listing.

IP: anti-Tie2
WB: Tie2 and pTyrosine

WB: pAKT and AKT

WB: pERK and ERK

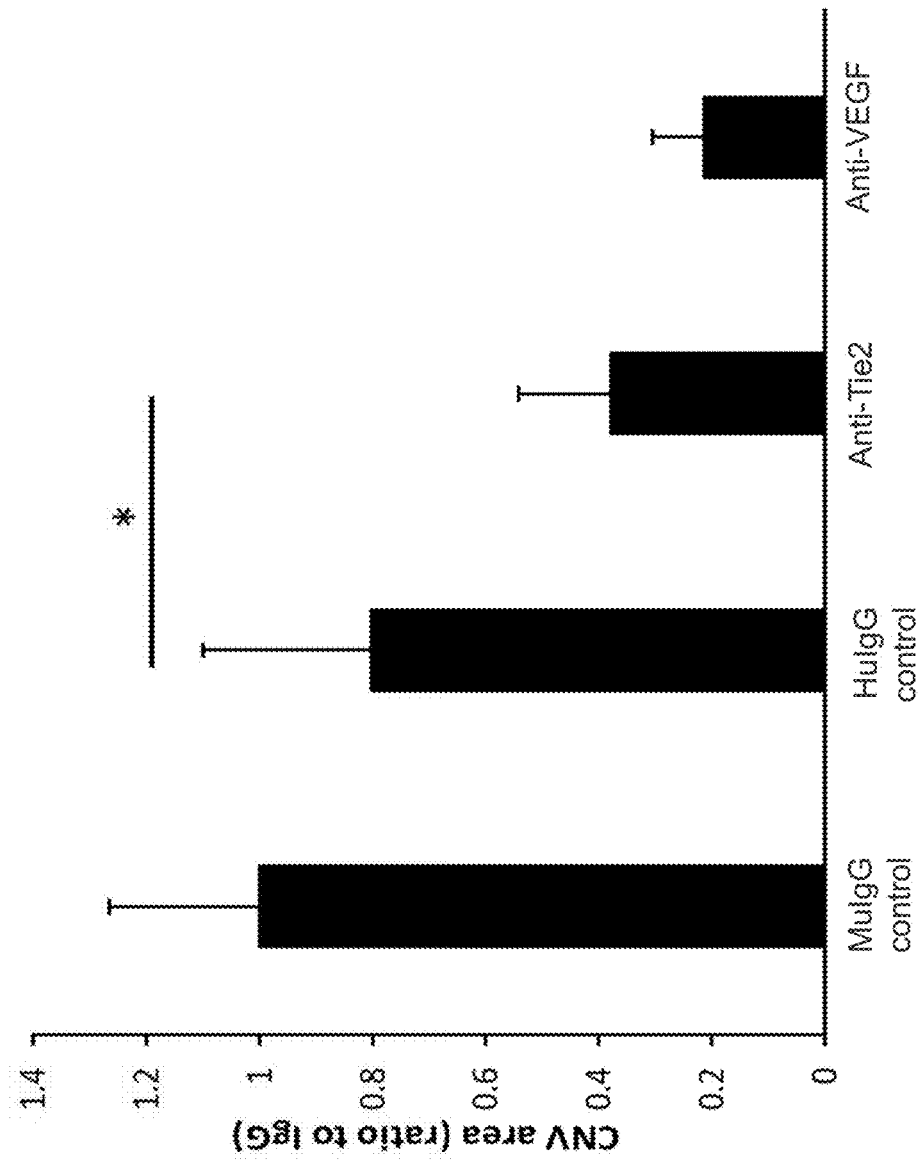

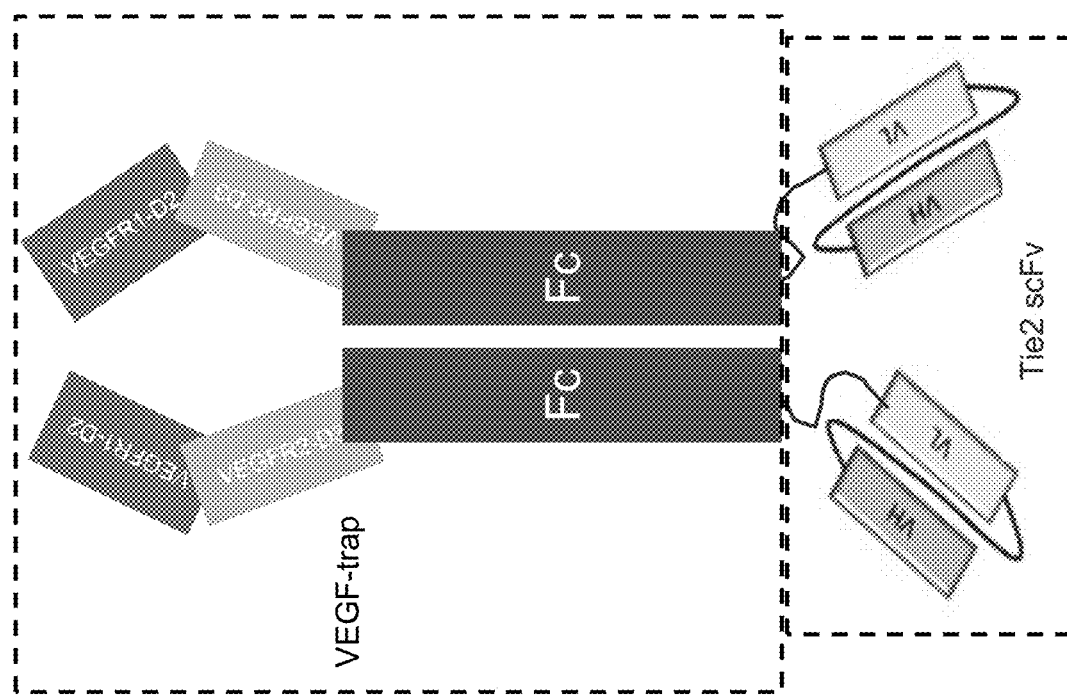

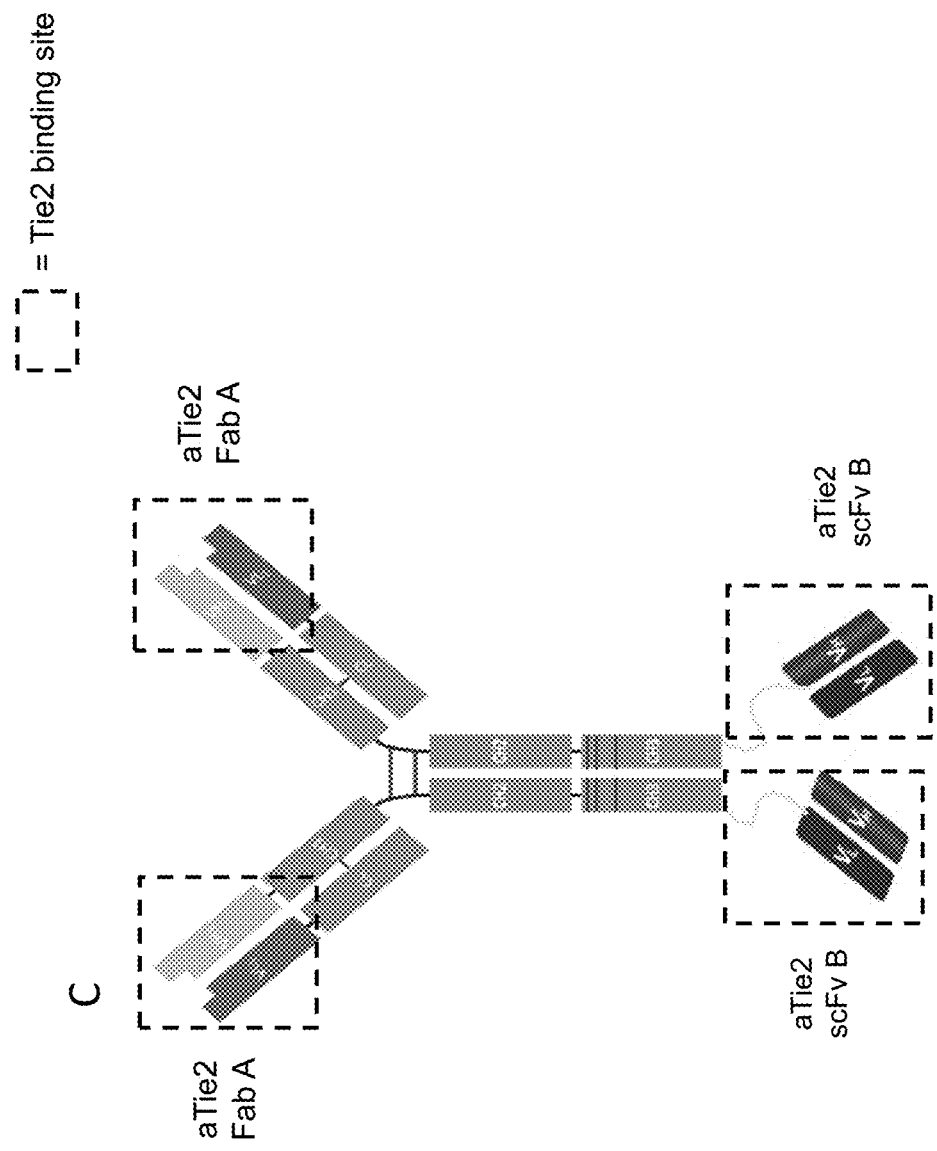
Figure 12, continued

ANTIBODIES DIRECTED TO TIE-2 AND METHODS OF USE

CROSS-REFERENCE TO RELATED APPLICATIONS

This application claims the benefit of priority to U.S. Provisional Application No. 62/938,816, filed Nov. 21, 2019, the disclosure of which is incorporated herein by reference in its entirety.

Incorporation-by-Reference of Sequence Listing Provided as a Text File

A Sequence Listing, filed on Nov. 19, 2020, is provided herewith as a text file, "UNITY-022_Seq_Listing_ST25" created on Nov. 19, 2020, and having a size of 162,514 bytes. The contents of the text file are incorporated by reference herein in their entirety.

FIELD OF THE INVENTION

The invention relates to anti-Tie2 antibodies and methods of using the same.

BACKGROUND OF THE INVENTION

Tie2 is a receptor tyrosine kinase that is predominantly expressed on the surface of endothelial cells, where it plays a central role in vessel stability, survival and maturation (Suri, C., et al., 1996. *Requisite Role of Angiopoietin-1, a Ligand for the TIE2 Receptor, during Embryonic Angiogenesis*. Cell 87 (7): 1171-80); Thurston, G., et al., 1999. *Leakage-Resistant Blood Vessels in Mice Transgenically Overexpressing Angiopoietin-1*. Science 286 (5449): 2511-14.; Saharinen, et al., 2010. *How Do Angiopoietins Tie with Vascular Endothelial Growth Factors?* Current Opinion in Hematology; Augustin, et al., 2009. *Control of Vascular Morphogenesis and Homeostasis through the Angiopoietin-Tie System*. Nature Reviews. Molecular Cell Biology 10 (3): 165-77; Milam, et al., 2015. *The Angiopoietin-Tie2 Signaling Axis in the Vascular Leakage of Systemic inflammation*. Tissue Barriers 3 (1-2)). Tie2 activity is tightly regulated by at least four soluble protein factors known as angiopoietins 1 to 4. Angiopoietin-1 (Ang1) and angiopoietin-2 (Ang2) are believed to be the predominant regulators of Tie2 function. Under normal physiological conditions, high Ang1 levels and low Ang2 levels maintain constitutive activation of the Tie2 signaling axis. Specifically, the Ang1 agonist ligand binds directly to the Tie2 receptor, leading to Tie2 clustering, autophosphorylation and downstream signaling events including the activation of the PI3-kinase/Akt and MAPK pathways.

Gene-targeting experiments have indicated that the Ang/Tie signaling system is needed for physiological and pathological remodeling of both lymphatic and blood vessels in embryonic, postnatal and adult mice (Eklund L, Kangas J, Saharinen P. *Angiopoietin-Tie signaling in the cardiovascular and lymphatic systems*. Clin Sci (Lond) 2017; 131: 87-103). In humans, an altered expression of angiopoietins is implicated in many vascular diseases (Saharinen P, Eklund L, Alitalo K. *Therapeutic targeting of the angiopoietin-TIE pathway*. Nat Rev Drug Discov 2017; 16: 635-61).

There remains a need for anti-Tie2 antibodies with improved properties as well as therapeutic and diagnostic uses thereof.

SUMMARY OF THE INVENTION

The present invention provides anti-Tie2 antibodies and methods of using the same for therapeutic and diagnostic purposes. The anti-Tie2 antibodies of the invention demonstrate unique properties that make them particularly suitable for use in therapy.

Specifically contemplated as part of the disclosed invention is:

Embodiment 1. An isolated anti-Tie2 antibody, or an antigen-binding fragment thereof, comprising three heavy chain complementarity-determining regions (CDR H1-3) and three light chain CDRs (CDR L1-3) as follows:

| Antibody Clone # | HCDR1 SEQ ID No. | HCDR2 SEQ ID No. | HCDR3 SEQ ID No. | LCDR1 SEQ ID No. | LCDR2 SEQ ID No. | LCDR3 SEQ ID No. |
|---|---|---|---|---|---|---|
| 3 | 1 | 41 | 81 | 121 | 161 | 201 |
| 8 | 2 | 42 | 82 | 122 | 162 | 202 |
| 9 | 3 | 43 | 83 | 123 | 163 | 203 |
| 10 | 4 | 44 | 84 | 124 | 164 | 204 |
| 4 | 5 | 45 | 85 | 125 | 165 | 205 |
| 11 | 6 | 46 | 86 | 126 | 166 | 206 |
| 12 | 7 | 47 | 87 | 127 | 167 | 207 |
| 13 | 8 | 48 | 88 | 128 | 168 | 208 |
| 14 | 9 | 49 | 89 | 129 | 169 | 209 |
| 15 | 10 | 50 | 90 | 130 | 170 | 210 |
| 16 | 11 | 51 | 91 | 131 | 171 | 211 |
| 17 | 12 | 52 | 92 | 132 | 172 | 212 |
| 18 | 13 | 53 | 93 | 133 | 173 | 213 |
| 19 | 14 | 54 | 94 | 134 | 174 | 214 |
| 20 | 15 | 55 | 95 | 135 | 175 | 215 |
| 21 | 16 | 56 | 96 | 136 | 176 | 216 |
| 22 | 17 | 57 | 97 | 137 | 177 | 217 |
| 23 | 18 | 58 | 98 | 138 | 178 | 218 |
| 24 | 19 | 59 | 99 | 139 | 179 | 219 |
| 25 | 20 | 60 | 100 | 140 | 180 | 220 |
| 1 | 21 | 61 | 101 | 141 | 181 | 221 |
| 26 | 22 | 62 | 102 | 142 | 182 | 222 |
| 27 | 23 | 63 | 103 | 143 | 183 | 223 |
| 28 | 24 | 64 | 104 | 144 | 184 | 224 |
| 29 | 25 | 65 | 105 | 145 | 185 | 225 |
| 30 | 26 | 66 | 106 | 146 | 186 | 226 |
| 6 | 27 | 67 | 107 | 147 | 187 | 227 |
| 2 | 28 | 68 | 108 | 148 | 188 | 228 |
| 31 | 29 | 69 | 109 | 149 | 189 | 229 |
| 5 | 30 | 70 | 110 | 150 | 190 | 230 |
| 32 | 31 | 71 | 111 | 151 | 191 | 231 |
| 33 | 32 | 72 | 112 | 152 | 192 | 232 |
| 39 | 33 | 73 | 113 | 153 | 193 | 233 |
| 22 | 34 | 74 | 114 | 154 | 194 | 234 |
| 34 | 35 | 75 | 115 | 155 | 195 | 235 |
| 35 | 36 | 76 | 116 | 156 | 196 | 236 |
| 36 | 37 | 77 | 117 | 157 | 197 | 237 |
| 37 | 38 | 78 | 118 | 158 | 198 | 238 |
| 38 | 39 | 79 | 119 | 159 | 199 | 239 |
| 40 | 40 | 80 | 120 | 160 | 200 | 240 |

Embodiment 2. An isolated anti-Tie2 antibody, or an antigen-binding fragment thereof comprising:
a heavy chain variable (VH) domain comprising an amino acid sequence of SEQ ID NO.242 and a light chain variable (VL) domain comprising an amino acid sequence of SEQ ID NO.243;
a heavy chain variable (VH) domain comprising an amino acid sequence of SEQ ID NO.244 and a light chain variable (VL) domain comprising an amino acid sequence of SEQ ID NO.245;
a heavy chain variable (VH) domain comprising an amino acid sequence of SEQ ID NO.246 and a light chain variable (VL) domain comprising an amino acid sequence of SEQ ID NO.247;

a heavy chain variable (VH) domain comprising an amino acid sequence of SEQ ID NO.248 and a light chain variable (VL) domain comprising an amino acid sequence of SEQ ID NO.249;
a heavy chain variable (VH) domain comprising an amino acid sequence of SEQ ID NO.250 and a light chain variable (VL) domain comprising an amino acid sequence of SEQ ID NO.251;
a heavy chain variable (VH) domain comprising an amino acid sequence of SEQ ID NO.252 and a light chain variable (VL) domain comprising an amino acid sequence of SEQ ID NO.253;
a heavy chain variable (VH) domain comprising an amino acid sequence of SEQ ID NO.254 and a light chain variable (VL) domain comprising an amino acid sequence of SEQ ID NO.255;
a heavy chain variable (VH) domain comprising an amino acid sequence of SEQ ID NO.256 and a light chain variable (VL) domain comprising an amino acid sequence of SEQ ID NO.257;
a heavy chain variable (VH) domain comprising an amino acid sequence of SEQ ID NO.258 and a light chain variable (VL) domain comprising an amino acid sequence of SEQ ID NO.259;
a heavy chain variable (VH) domain comprising an amino acid sequence of SEQ ID NO.260 and a light chain variable (VL) domain comprising an amino acid sequence of SEQ ID NO.261;
a heavy chain variable (VH) domain comprising an amino acid sequence of SEQ ID NO.262 and a light chain variable (VL) domain comprising an amino acid sequence of SEQ ID NO.263;
a heavy chain variable (VH) domain comprising an amino acid sequence of SEQ ID NO.264 and a light chain variable (VL) domain comprising an amino acid sequence of SEQ ID NO.265;
a heavy chain variable (VH) domain comprising an amino acid sequence of SEQ ID NO.266 and a light chain variable (VL) domain comprising an amino acid sequence of SEQ ID NO.267;
a heavy chain variable (VH) domain comprising an amino acid sequence of SEQ ID NO.268 and a light chain variable (VL) domain comprising an amino acid sequence of SEQ ID NO.269; or
a heavy chain variable (VH) domain comprising an amino acid sequence of SEQ ID NO.270 and a light chain variable (VL) domain comprising an amino acid sequence of SEQ ID NO.271.

Embodiment 3. An isolated anti-Tie2 antibody, wherein the antibody specifically binds to an epitope within the human Tie2 extracellular domain, said epitope comprising amino acid residues K312, S316, C332, H358, K387, and T391, according to EU numbering as in Kabat, as measured by crosslink mass spectrometry.

Embodiment 4. The antibody of embodiments 1-3, wherein the antibody is an allosteric activator of Tie2.

Embodiment 5. The antibody of embodiments 1-4, wherein the antibody is a non-ligand competitive binder of Tie2.

Embodiment 6. The antibody of embodiments 3-5, wherein the antibody is cross-reactive against human, mouse, rat, rabbit and monkey Tie2.

Embodiment 7. The antibody of embodiments 1-6, wherein said antibody is fully human, humanized, monoclonal, or chimeric.

Embodiment 8. The antibody of embodiments 1-7, wherein said antibody is monospecific.

Embodiment 9. The antibody of embodiments 1-7, wherein said antibody is multispecific.

Embodiment 10. The antibody of embodiment 9, wherein the multispecific antibody is bispecific.

Embodiment 11. The antibody of embodiment 10, wherein the bispecific antibody comprises one binding arm that specifically binds human Tie-2 of claim 8 and a second binding arm that specifically binds VEGF-A, VEGF-B, VEGF-C, VEGF variants, Ang-1, Ang-2, Ang-3, Ang-4, PDGF-β, interleukin-1β, VE-PTP, complement factor C3, integrin α5β1, amyloid beta, PD-1, PD-L1, or CTLA-4.

Embodiment 12. The antibody of embodiment 9, wherein the multispecific antibody is a biparatopic antibody.

Embodiment 13. The antibody of embodiment 12, wherein the biparatopic antibody comprises one binding arm that specifically binds a first epitope on the ECD of human Tie2 and the other binding arm that specifically binds to a second epitope on the ECD of human Tie2.

Embodiment 14. The antibody of embodiment 9, wherein the multispecific antibody is a trivalent, a tetravalent, a pentavalent, a hexavalent antibody, wherein the trivalent, tetravalent, pentavalent, or hexavalent antibody comprises at least one binding arm that specifically binds human Tie2 of claim 8 and other remaining binding arms that specifically binds VEGF-A, VEGF-B, VEGF-C, VEGF variants, Ang-1, Ang-2, Ang-3, Ang-4, PDGF-β, interleukin-1β, VE-PTP, complement factor C3, integrin α5β1, amyloid beta, PD-1, PD-L1, or CTLA-4.

Embodiment 15. The antibody of embodiments 1-14, wherein said antibody is an antibody fragment that specifically binds human Tie2.

Embodiment 16. The antibody of embodiment 15, wherein the antibody fragment is a Fab, a Fab'-SH, a Fv, a scFv, or a (Fab')$_2$ fragment.

Embodiment 17. The antibody of embodiment 16, wherein the multispecific antibody is comprised of scFv antibody fragments linked together by a polypeptide linker.

Embodiment 18. The antibody of embodiments 1-17, wherein the antibody possesses reduced effector function.

Embodiment 19. The antibody of embodiment 18, wherein the antibody comprises at least one substitution mutation at amino acid residue N297, L234, L235, P329, D265, and E430 according to EU numbering as in Kabat.

Embodiment 20. The antibody of embodiment 19, wherein the at least one substitution mutation is selected from the group consisting of amino acid residue N297G, N297A, L234A, L235A, P329G, D265A, and E430G according to EU numbering as in Kabat.

Embodiment 21. The antibody of embodiment 20, wherein the antibody comprises the substitution mutation at residue N297A or N297G.

Embodiment 22. The antibody of embodiment 20, wherein the antibody comprises the substitution mutation at residues L234A, L235A and P329G.

Embodiment 23. The antibody of embodiment 20, wherein the antibody comprises the substitution mutation at residues D265A and N297G.

Embodiment 24. The antibody of embodiment 21, wherein the antibody further comprises the substitution mutation at residue E430G.

Embodiment 25. The antibody of embodiment 22, wherein the antibody further comprises the substitution mutation at residue E430G.

Embodiment 26. The antibody of embodiment 23, wherein the antibody further comprises the substitution mutation at residue E430G.

Embodiment 27. The antibody of embodiment 25, wherein the antibody comprises a heavy chain comprising an amino acid sequence of SEQ ID NO:174 and a light chain comprising an amino acid sequence of SEQ ID NO:175.

Embodiment 28. The antibody of embodiment 22 comprising: a heavy chain comprising an amino acid sequence of SEQ ID NO:276 and a light chain comprising an amino acid sequence of SEQ ID NO:277;

a heavy chain comprising an amino acid sequence of SEQ ID NO:278 and a light chain comprising an amino acid sequence of SEQ ID NO:279;

a heavy chain comprising an amino acid sequence of SEQ ID NO:280 and a light chain comprising an amino acid sequence of SEQ ID NO:281;

a heavy chain comprising an amino acid sequence of SEQ ID NO:282 and a light chain comprising an amino acid sequence of SEQ ID NO:283;

a heavy chain comprising an amino acid sequence of SEQ ID NO:286 and a light chain comprising an amino acid sequence of SEQ ID NO:287; or a heavy chain comprising an amino acid sequence of SEQ ID NO:288 and a light chain comprising an amino acid sequence of SEQ ID NO:289.

Embodiment 29. The antibody of embodiment 10 comprising:

an amino acid sequence of SEQ ID NO:284; or an amino acid sequence of SEQ ID NO:285.

Embodiment 30. An isolated nucleic acid encoding the antibody of embodiments 1-29.

Embodiment 31. A vector comprising the isolated nucleic acid of embodiment 30.

Embodiment 32. A host cell comprising the vector of embodiment 31.

Embodiment 33. A method of producing the antibody of embodiments 1-29, the method comprising culturing the host cell of embodiment 32 in a culture medium and isolating the resulting antibody.

Embodiment 34. An immunoconjugate comprising the antibody of embodiments 1-29.

Embodiment 35. A fusion polypeptide comprising the antibody of embodiments 1-29.

Embodiment 36. A pharmaceutical composition comprising the antibody of embodiments 1-29, the immunoconjugate of embodiment 34, or the fusion polypeptide of embodiment 35.

Embodiment 37. The pharmaceutical composition of embodiment 36, wherein the antibody, the immunoconjugate, or the fusion polypeptide is co-formulated with an anti-VEGF antibody or a VEGF extracellular trap protein.

Embodiment 38. A method of treating a Tie2 dysregulated disease in a subject in need thereof, the method comprising administering to the subject the pharmaceutical composition of embodiment 36.

Embodiment 39. A method of treating a Tie2 dysregulated disease in a subject in need thereof, the method comprising administering to the subject the pharmaceutical composition of embodiment 37.

Embodiment 40. The method of embodiment 38, further comprising co-administering to the subject a pharmaceutical composition comprising an anti-VEGF antibody or a VEGF extracellular trap protein.

Embodiment 41. The method of embodiments 38-40, wherein the Tie2 dysregulated disease comprise infectious diseases, acute respiratory distress syndrome (ARDS), ischemic injuries, ocular disorders, radiation injury, cancer, systemic sclerosis, traumatic brain injury, neuroinflammation, radiation injury, wound healing, myocardial infarction, blood brain barrier compromise, cerebral cavernous malformations, Duchenne Muscular dystrophy (DMD) or Clarkson Disease.

Embodiment 42. The method of embodiment 38-40, wherein the Tie2 dysregulated infectious diseases comprise sepsis, dengue virus infection, tuberculosis, or influenza.

Embodiment 43. The method of embodiment 38-40, wherein the Tie2 dysregulated ischemic injuries comprise diabetic nephropathy, acute kidney injury, chronic kidney disease, organ transplant, critical limb ischemia, traumatic brain injury or stroke.

Embodiment 44. The method of embodiment 38-40, wherein the Tie2 dysregulated ocular disorders comprise diabetic retinopathy, diabetic macular edema (DME), proliferative diabetic retinopathy (PDR) age-related macular degeneration (AMD), retinopathy of prematurity (ROP), or glaucoma.

Embodiment 45. The isolated anti-Tie2 antibody of embodiments 1-29, or the immunoconjugate of embodiment 34, or the fusion polypeptide of embodiment 35 for use in the treatment of the Tie2 dysregulated diseases of embodiments 41-44.

Embodiment 46. Use of the isolated anti-Tie2 antibody of embodiments 1-29, or the immunoconjugate of embodiment 34, or the fusion polypeptide of embodiment 35 for the manufacture of a medicament for treating the Tie2 dysregulated diseases of embodiments 41-44.

BRIEF DESCRIPTION OF THE DRAWINGS

FIG. 1A shows Tie2 was immunoprecipitated from lysates using anti-Tie2 antibodies and levels of pTie2 were determined by western blotting with an anti-phospho-tyrosine antibody. For pAkt and pERK analysis, western blotting for pAkt, and total Akt (FIG. 1B) or pERK and total ERK (FIG. 1C) in whole cell lysates was performed. See Example 3.

FIGS. 9A to 9B. Anti-Tie2 antibodies inhibit laser-induced choroidal neovascularization (CNV) in a mouse model. Quantification of neovascularization in lesion area and vascular density in retina was carried out by Image J. P values were assessed by Student's t test (significant change, p<0.05). See Example 11.

FIGS. 10A to 10B. Schematics of Tie2/VEGF bispecific constructs of the invention. FIG. 10A shows a schematic of an anti-Tie2 antibody linked via polypeptide linkers to two VEGF scFv antibody fragments. Exemplary constructs are embodied in antibody clone #57 and in antibody clone #58. FIG. 10B shows a schematic of two anti-Tie2 scFv antibody fragments linked to two VEGF-trap proteins comprised of R1-D2 and R3-D3. Exemplary constructs are embodied in antibody clone #55 and #56. See Example 13.

DETAILED DESCRIPTION OF THE INVENTION

I. Definitions

Figure 1A:
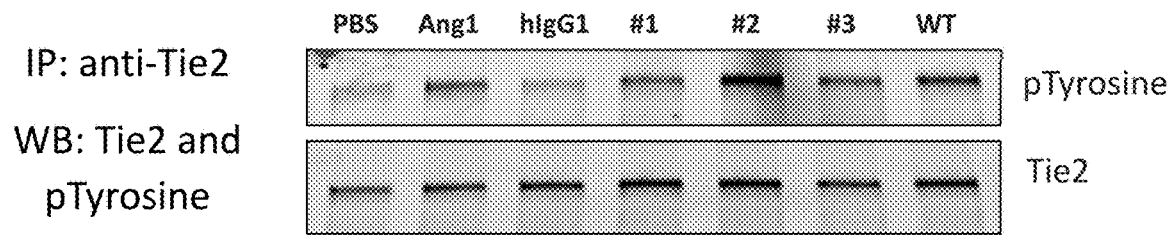
FIGS. 1A to 1C. Anti-Tie2 antibodies increase the levels of phospho-Tie2 (pTie2) as well as phospho-Akt (pAkt) and phospho-ERK (pERK) as determined by western blotting. HUVEC cells were serum starved and then treated with either PBS, Ang1 (12 nM), control hIgG1 (12 nM), or human anti-Tie2 antibodies #1, #2 and #3 or a wild-type (WT) chicken anti-Tie2 antibody (12 nM) for 20 minutes, followed by cell lysis.

"Tie2" is also known as angiopoietin-1 receptor, or TEK receptor tyrosine kinase, or CD202B (cluster of differentiation 202B), and is a protein that in humans is encoded by the TEK gene (Partanen J et al., (April 1992). *A novel endothelial cell surface receptor tyrosine kinase with extracellular epidermal growth factor homology domains*. Molecular and Cellular Biology. 12 (4): 1698-707). This receptor possesses a unique extracellular domain containing three immunoglobulin-like loops, three epidermal growth factor-like repeats and three fibronectin type III-like repeats (see Fiedler et al., 2006. *Angiopoietins: A Link between Angiogenesis and inflammation*. Trends in Immunology 27 (12): 552-58; Barton et al., *Crystal structures of the Tie2 receptor ectodomain and the angiopoietin-2-Tie2 complex*. Nature Struc. & Mol. Biology, 13, pp 524-532 (2006)). The contact residues for angiopoietin-1 and angiopoietin-2 are mostly overlapping on the Tie-2 receptor and are predominantly located in the second Ig-like loop, as suggested by the analysis of the crystal structure of the Ang2/Tie2 complex (Barton et al., Nat Str Biol 2006). Other work supports the concept that the binding domains for Ang1 and Ang2 are similar or identical (Fiedler et al., *Angiopoietin-1 and angiopoietin-2 share the same binding domains in the Tie-2 receptor involving the first Ig-like loop and the epidermal growth factor-like repeats*. JBC. Vol. 278 (3): 1721-7 (2003)). The amino acid sequence of an exemplary human Tie2 may be found under UniProt Accession Number Q02763 (SEQ ID NO:241).

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Active" or "activity" or "biological activity" in the context of an antibody of the present invention is the ability to agonize (partially or fully activate) a biological activity of its target, for example, in vitro and/or in vivo. One example of a biological activity of an antibody is the ability to achieve a measurable improvement in the state, e.g., pathology, of a disorder associated with its target. For example, for an anti-Tie2 antibody, the disorder may be a Tie2-associated disorder, such as, for example, AMD (e.g., geographic atrophy). The activity of an anti-Tie2 antibody can be determined in in vitro or in vivo tests, including binding assays, activity assays (e.g., FRET-based activity assays (e.g., using an H2-Opt substrate) or mass spectrometry-based activity assays or signal transduction assays), using a relevant animal model, or human clinical trials. The activity of an anti-Tie2 antibody of the invention can be determined in in vitro or in vivo tests, including binding assays, alternative pathway hemolysis assays (e.g., assays measuring inhibition of the alternative pathway complement activity or activation), using a relevant animal model, or human clinical trials.

The term "active site on Tie2" is defined as the Ang 1/Ang 2 binding domain on Tie2, which is known to be within the Ig2-like domain of the extracellular domain of Tie2.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein.

An "affinity matured" antibody refers to an antibody with one or more alterations in one or more hypervariable regions (CDRs) and/or framework regions (FRs), compared to a parent antibody which does not possess such alterations, such alterations resulting in an improvement in the affinity of the antibody for antigen.

"Allosteric activation of Tie2" is the activation of Tie2 by an agonistic anti-Tie2 antibody that specifically interacts with regions of Tie2 outside of the described ligand binding or active site, such that the binding results in a change in Tie2 conformation or clustering that enhances the receptor's activity.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire light (L) chain along with the variable region domain of the heavy (FI) chain (VH), and the first constant domain of one heavy chain (CH1). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md. (1991).

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

"Single-chain Fv" also abbreviated as "sFv" or "scFv" are antibody fragments that comprise the VH and VL antibody domains connected into a single polypeptide chain. The sFv polypeptide may further comprise a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448, 1993.

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonistic" or "activating" antibody is one which activates, stimulates or increases biological or signaling activity of the antigen it binds. In some situations, it is contemplated that an agonistic antibody can act in a similar manner to how a ligand engages and activates its cognate receptor. In other situations, it is contemplated that the anti-Tie2 antibodies of the invention are considered agonistic if they induce Tie2 signaling as determined by increased levels of one or more of intracellular phosphorylated Tie2 (pTie2), and/or phosphorylated Akt (pAkt), and/or phosphorylated ERK (pERK), as described in Example 3. In addition, it is further contemplated that an agonistic Tie2 antibody of the invention can also be capable of activating downstream signaling of its target antigen in the presence or absence of endogenous activating (i.e. Ang1) or inhibitory (i.e. Ang2) ligands, as described in Examples 6 and 7.

An "antibody that binds to the same epitope" as a reference antibody refers to an antibody that contacts an overlapping set of amino acid residues of the antigen as compared to the reference antibody or blocks binding of the reference antibody to its antigen in a competition assay by 50% or more. The amino acid residues of an antibody that contact an antigen can be determined, for example, by determining the crystal structure of the antibody in complex with the antigen or by performing hydrogen/deuterium exchange. In some embodiments, residues of an antibody that are within 5 angstroms of the antigen are considered to contact the antigen. In some embodiments, an antibody that binds to the same epitope as a reference antibody blocks binding of the reference antibody to its antigen in a competition assay by 50% or more, and conversely, the reference antibody blocks binding of the antibody to its antigen in a competition assay by 50% or more. An exemplary competition assay is provided herein.

The term "biparatopic" as used herein, refers to a bispecific antibody where the first antigen-binding moiety and the second antigen-binding moiety bind to different epitopes on the same antigen.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ and μ, respectively.

"Complement factors" means the various proteins and glycoproteins that make up the complement cascade which is a part of the immune system that enhances (complements) the ability of antibodies and phagocytic cells to clear microbes and damaged cells from an organism, promote inflammation, and attack the pathogen's cell membrane. It is part of the innate immune system. Complement factors contemplated herein include, for example, C1, C2, C2a, C2b, C3, C3a, C3b, C4, C4a, C4b, C5, C5a, C5b, C6, C7, C8 and C9.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down-regulation of cell surface receptors (e.g., B cell receptor); and B cell activation.

"Framework" or "framework region" or "FR" refers to variable domain residues other than hypervariable region (CDR) residues. The FR of a variable domain generally consists of four FR domains: FR1, FR2, FR3, and FR4.

The terms "full-length antibody," "intact antibody," and "whole antibody" are used herein interchangeably to refer to an antibody having a structure substantially similar to a native antibody structure or having heavy chains that contain an Fc region as defined herein.

The term "fusion polypeptide" encompasses anti-Tie2 antibodies of the invention fused to, for example, an immunoglobulin Fc region. An Fc region may comprise, for example, a CH3 domain of an immunoglobulin, which may be naturally occurring or modified in some way. Such Fc fusion polypeptides can exhibit a greater half-life in vivo than the unfused counterpart. Also, a fusion to an Fc region allows for dimerization/multimerization of the fusion polypeptide. As contemplated, the Fc region may be a naturally occurring Fc region, or may be altered to improve certain qualities, such as therapeutic qualities, circulation time, decrease aggregation problems, for example. In another embodiment, a fusion polypeptide contemplates anti-Tie2 antibody fragments fused to a ligand, such as, for example, Ang1 to enhance agonistic activity of the fusion polypeptide. In another embodiment, a fusion polypeptide contemplates an anti-Tie2 antibody fragments fused to, for example, a cytokine to elicit other desired biology.

As used herein, a "hexamerized antibody" is one in which the introduction of the E430G mutation in the Fc region facilitates the natural process of antibody hexamer formation through increased intermolecular Fc-Fc interactions upon binding to membrane-bound antigens at the cell surface (Diebolder et al., Science. 2014; de Jong et al., PLoS Biol. 2016).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, FR residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr Op. Struct. Biol. 2:593-596 (1992).

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the span of the variable domains. Instead, the V regions consist of relatively invariant stretches called framework regions (FRs) of 15-30 amino acids separated by shorter regions of extreme variability called "hypervariable regions" that are each 9-12 amino acids long. The term "hypervariable region" or "CDR" when used herein refers to the amino acid residues of an antibody which are responsible for antigen-binding. The hypervariable region generally comprises amino acid residues from, for example, around about residues 24-34 (L1), 50-56 (L2) and 89-97 (L3) in the VL, and around about residues 26-35 (H1), 49-65 (H2) and 95-102 (H3) in the VH (in one embodiment, H1 is around about residues 31-35); Kabat et al., Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2), and 91-96 (L3) in the VL, and 26-32 (H1), 53-55 (H2), and 96-101 (H3) in the VH; Chothia and Lesk, J. Mol. Biol. 196:901-917 (1987). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). Accordingly, the CDR and FR sequences generally appear in the following sequence in VH (or VL): FR1-H1 (L1)-FR2-H2(L2)-FR3-H3(L3)-FR4. The constant domains are not involved directly in binding an antibody to an antigen, but exhibit various effector functions, such as participation of the antibody in antibody dependent cellular cytotoxicity (ADCC).

The terms "residue numbering as in Kabat," "Kabat amino acid residue," or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc., according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system. Unless otherwise indicated, CDR residues and other residues in the variable domain (e.g., FR residues) are numbered herein according to Kabat et al., supra.

An "immunoconjugate" is an antibody conjugated to one or more heterologous molecule(s) that delivers a cell-killing or cell-altering activity, including but not limited to a small molecule drug (inhibitor or activator), or cytotoxic agent, such as chemotherapeutic agents or drugs, growth inhibitory agents, toxins (e.g., protein toxins, enzymatically active toxins of bacterial, fungal, plant, or animal origin, or fragments thereof), or radioactive isotopes.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) approaches. For a review of methods for assessment of antibody purity, see, for example, Flatman et al., J. Chromatogr. B 848:79-87 (2007). In certain embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "multispecific antibody" is used in the broadest sense and specifically covers an antibody or antibody fragment having polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 µM to 0.001 pM, 3 µM to 0.001 pM, 1 µM to 0.001 pM, 0.5 µM to 0.001 pM or 0.1 µM to 0.001 pM. "Monospecific" refers to an antibody having the ability to bind only one epitope on a particular antigen.

With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a KD for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a KD in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and KD values are inversely related. A high affinity for an antigen is measured by a low KD value. In one embodiment, the term "specific binding" refers to binding where a molecule, such as an antibody of the invention, binds to a particular polypeptide or epitope on a particular polypeptide without substantially binding to any other polypeptide or polypeptide epitope.

The term "non-ligand competitive binder" is an anti-Tie2 antibody of the invention that does not compete for the active site of Tie2 with either Ang 1 or Ang 2, while still allowing either Ang 1 or Ang 2 to bind at the active site.

A "nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell. In some embodiments, the nucleic acid encodes an anti-Tie2 antibody.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell but may contain mutations. Mutant progeny that have the same function or biological activity as screened or selected for in the originally transformed cell are included herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

A protein, including an antibody, is said to be "stable" if it essentially retains the intact conformational structure and biological activity. Various analytical techniques for measuring protein stability are available in the art and are reviewed in, e.g., Peptide and Protein Drug Delivery, 247-301, Vincent Lee Ed., Marcel Dekker, Inc., New York, N.Y., Pubs. (1991) and Jones (1993) Adv. Drug Delivery Rev. 10: 29-90. An antibody variant with "improved stability" refers to an antibody variant that is more stable comparing to the starting reference antibody. Antibody variants with improved stability are variants of the reference (wild-type) antibodies in which specific amino acid residues are altered for the purpose of improving physical stability, and/or chemical stability, and/or biological activity, and/or reducing immunogenicity of the native antibodies.

In certain embodiments, the anti-Tie2 antibody can be used as a therapeutic agent in targeting and interfering with diseases or conditions wherein the Tie2 activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062).

The term "trispecific" as used herein, refers to a type of antibody which possesses three antigen-recognition and binding sites, some of which may bind to Tie2. In another case, at least one binding arm specifically binds Tie2 and other binding sites may bind to either Tie2 or another antigen of interest (listed under "bispecific antibodies"). In one aspect, such trispecific antibodies comprise antibody fragments (e.g., Fabs, scFvs, single-domain antibodies). As a non-limiting example, three antibody-binding fragments of the invention may be assembled into a trispecific antibody such that at least one antibody-binding fragments bind Tie2 and the remaining antibody-binding fragments bind another antigen, such as, for example, VEGF. See Runcie et al., Bi-specific and Tri-specific antibodies—the next big thing in solid tumor therapeutics., Mol. Med., 24, (50)(2018).

The term "tetravalent" as used herein, refers to a type of antibody which possesses four antigen-recognition and binding sites, some of which may bind to Tie2. In another case, at least one binding arm specifically binds Tie2 and other binding sites may bind to either Tie2 or another antigen of interest (listed under "bispecific antibodies"). In one aspect, such tetravalent antibodies comprise antibody fragments (e.g., Fabs, scFvs, single-domain antibodies). As a non-limiting example, four antibody-binding fragments of the invention may be assembled into a tetravalent antibody such that two antibody-binding fragments bind Tie2 and the other two antibody-binding fragments bind another antigen, such as, for example, VEGF.

The term "pentavalent" as used herein, refers to a type of antibody which possesses five antigen-recognition and binding sites, some of which may bind to Tie2. In another case, at least one binding arm specifically binds Tie2 and other binding sites may bind to either Tie2 or another antigen of interest (listed under "bispecific antibodies". In one aspect, such pentavalent antibodies comprise antibody fragments (e.g., Fabs, scFvs, single-domain antibodies). As a non-limiting example, five antibody-binding fragments of the invention may be assembled into a pentavalent antibody such that at least one antibody-binding fragment binds Tie2 and the other antibody-binding fragments bind another antigen, such as, for example, VEGF.

The term "hexavalent" as used herein, refers to a type of antibody which possesses six antigen-recognition and binding sites, some of which may bind to Tie2. In another case, at least one binding arm specifically binds Tie2 and other binding sites may bind to either Tie2 or another antigen of interest, listed under "bispecific antibodies". In one aspect, such hexavalent antibodies comprise antibody fragments (e.g., Fabs, scFvs, single-domain antibodies). As a non-limiting example, six antibody-binding fragments of the invention may be assembled into a hexavalent antibody such that at least one antibody-binding fragment binds Tie2 and the other antibody-binding fragments bind another antigen, such as, for example, VEGF.

A "polypeptide linker" as used herein is a polypeptide comprising two or more amino acid residues joined by peptide bonds that are used to link two polypeptides (e.g., a VH and VL domain, two scFv antibody fragments or a variable domain and an extracellular trap protein or a scFv antibody fragment and an extracellular trap protein). Linkers may be flexible or rigid/non-flexible. Examples of such linker polypeptides are well known in the art (see, e.g., Hollinger P, et al., PNAS USA. 90:6444-6448 (1993); Poljak R J. Structure 2: 1121-1123 (1994)). Non-limiting examples of suitable, non-immunogenic linker peptides are: (G4S)n, (SG4)n or G4(SG4)n flexible peptide linkers, or rigid/non-flexible linkers (EAAAK)n or (XP)n, in both cases where "n" is a number between 1 and 10, or between 1 and 4, as well as oligomers of such linkers.

A "Tie2 dysregulation disease" is any condition that would benefit from treatment with the anti-Tie2 antibody of the invention. Non-limiting examples of diseases to be treated herein include, without limitation, any disease or disorder that results from an imbalance or disruption of the Ang-1, Ang-2, Ang-3 or Ang-4 and Tie2 interactions. Non-limiting examples may encompass, for example, infectious diseases, acute respiratory distress syndrome (ARDS), ischemic injuries, ocular disorders, radiation injury, cancer, systemic sclerosis, traumatic brain injury, radiation injury, wound healing, myocardial infarction, blood brain barrier compromise (i.e. in Alzheimer's disease or other neurodegenerative diseases), neuroinflammation, cerebral cavernous malformations, Duchenne Muscular dystrophy (DMD) or Clarkson Disease. In one embodiment, the Tie2 dysregulated infectious disease comprise sepsis, dengue virus infection, tuberculosis, or influenza. In another embodiment, the Tie2 dysregulated disease may encompass ischemic injuries, such as, for example, diabetic nephropathy, acute kidney injury, chronic kidney disease, kidney or other organ transplantation, critical limb ischemia, traumatic brain injury or stroke. In another embodiment, the Tie2 dysregulated ocular disorders may include, for example, diabetic retinopathy, diabetic macular edema (DME), proliferative diabetic retinopathy (PDR) age-related macular degeneration (AMD), retinopathy of prematurity (ROP) or glaucoma.

As used herein, "administering" is meant a method of giving a dosage of a therapeutic (e.g., an anti-Tie2 antibody of the invention, a nucleic acid encoding an anti-Tie2 antibody of the invention) or a composition (e.g., a pharmaceutical composition, e.g., a pharmaceutical composition including an anti-Tie2 antibody of the invention) to a subject in need thereof. The compositions utilized in the methods described herein can be administered, for example, intravitreally (e.g., by intravitreal injection), ocularly (e.g., by ocular injection), intraocularly (e.g., by intraocular injection), sub-cutaneously or intravenously. The compositions utilized in the methods described herein can also be administered systemically or locally. The method of administration can vary depending on various factors (e.g., the compound or composition being administered, and the severity of the condition, disease, or disorder being treated).

As used herein, "co-administering" means the administration of two or more separate therapeutics (e.g., an anti-Tie2 antibody of the invention and an anti-VEGF antibody therapeutic or a recombinant VEGF fusion protein therapeutic) or compositions (e.g., an anti-Tie2 antibody pharmaceutical composition of the invention and an anti-VEGF antibody composition or a recombinant VEGF fusion protein composition) concurrently or at the same time to a subject in need thereof.

As used herein, "co-formulated" means two or more separate therapeutics (e.g., an anti-Tie2 antibody of the invention and an anti-VEGF antibody or a recombinant VEGF fusion protein) or compositions (e.g., an anti-Tie2 antibody pharmaceutical composition of the invention and an anti-VEGF antibody composition or a recombinant VEGF fusion protein composition) that are combined in a single formulation that is administered to a subject in need thereof.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. A "subject" may be a "patient."

As used herein, "treatment" (and "treat" or "treating") refers to clinical intervention in an attempt to alter the natural course of the individual being treated and can be performed either for prophylaxis or during the course of clinical pathology. Desirable effects of treatment include, but are not limited to, preventing recurrence of the disease or disorder, alleviation of symptoms, diminishment of any direct or indirect pathological consequences of the disease or disorder, decreasing the rate of disease progression, amelioration or palliation of the disease or disorder state, and remission or improved prognosis. In some embodiments, antibodies of the invention are used to delay development of a disease or disorder or to slow the progression of a disease or disorder.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

A "mutation" is a deletion, insertion, or substitution of a nucleotide(s) relative to a reference nucleotide sequence, such as a wild-type sequence.

A "variant" or "mutant" of a starting or reference polypeptide (e.g., a reference antibody or its variable domain(s)/ CDR(s)), is a polypeptide that (1) has an amino acid sequence different from that of the starting or reference polypeptide and (2) was derived from the starting or reference polypeptide through either natural or artificial (man-made) mutagenesis. Such variants include, for example, deletions from, and/or insertions into and/or substitutions of, residues within the amino acid sequence of the polypeptide of interest, referred to herein as "amino acid residue alterations." Thus, a variant CDR refers to a CDR comprising a variant sequence with respect to a starting or reference polypeptide sequence (such as that of a source antibody or antigen binding fragment). An amino acid residue alteration, in this context, refers to an amino acid different from the amino acid at the corresponding position in a starting or reference polypeptide sequence (such as that of a reference antibody or fragment thereof). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "VEGF extracellular trap protein" or "VEGF-Trap" as used herein is otherwise known as aflibercept (Eylea®, Regeneron-Bayer FlealthCare, Tarrytown, N.Y., US). It consists of ligand-binding elements taken from the extracellular components of VEGF receptors 1 and 2 fused to the Fc portion of IgG1. It binds all isoforms of VEGF-A as well as VEGF-B and placental growth factor (PlGF) with a high affinity and essentially renders the VEGF-A and PlGF ligands unable to bind and activate cell receptors.

A "wild-type (WT)" or "reference" sequence or the sequence of a "wild-type" or "reference" protein/polypeptide, such as an CDR or a variable domain of a reference antibody, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man-induced means. The products of such processes are "variant" or "mutant" forms of the original "wild-type" protein or gene.

A "reference antibody," as used herein, refers to an antibody or fragment thereof whose antigen-binding sequence serves as the template sequence upon which diversification according to the criteria described herein is performed. An antigen-binding sequence generally includes an antibody variable region, at least one CDR, including framework regions.

Compositions and Methods

The invention provides novel antibodies that bind to Tie2, and methods of making and using the same, for example, for therapeutic and diagnostic uses. Antibodies of the invention are useful, e.g., for the diagnosis or treatment of various disorders, including Tie2 dysregulated disease, described herein.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3*d edition* (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; Cell Biology: A Laboratory Notebook (J. E. Cellis, ed., 1998) Academic Press; Animal Cell Culture (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds, Harwood Academic Publishers, 1995).

The anti-Tie2 antibodies of the invention described herein, as well as any of the antibodies for use in a method described herein, may have any of the features, singly or in combination, described herein.

In certain embodiments, an anti-Tie2 antibody provided herein has a dissociation constant (KD) of about 1 μM, about 100 nM, about 10 nM, about 1 nM, about 0.1 nM, about 0.01 nM, or about 0.001 nM (e.g., $10^{-8}$ M or less, e.g., from $10^{-8}$ M to $10^{-13}$ M, e.g., from $10^{-9}$ M to $10^{-13}$ M). For example, in some instances, an antibody provided herein binds human Tie2 (huTie2) with a KD of about 10 nM or lower. In some instances, an antibody provided herein binds huTie2 with a KD of about 5 nM or lower. In some instances, an antibody provided herein binds huTie2 with a KD of about 2 nM or lower. For example, in some instances, the antibody binds huTie2 with a KD between about 25 pM and about 2 nM (e.g., about 25 pM, about 50 pM, about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM, about 625 pM, about 650 pM, about 675 pM, about 700 pM, about 725 pM, about 750 pM, about 775 pM, about 800 pM, about 825 pM, about 850 pM, about 875 pM, about 900 pM, about 925 pM, about 950 pM, about 975 pM, about 1 nM, about 1.1 nM, about 1.2 nM, about 1.3 nM, about 1.4 nM, about 1.5 nM, about 1.6 nM, about 1.7 nM, about 1.8 nM, about 1.9 nM, or about 2 nM). In some instances, the antibody binds huTie2 with a KD between about 75 pM and about 600 pM (e.g., about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM). In some instances, the antibody binds huTie2 with a KD between about 75 pM and about 500 pM. In some instances, the antibody binds huTie2 with a KD between about 75 pM and about 400 pM. In some instances, the antibody binds huTie2 with a KD between about 75 pM and about 300 pM. In some instances, the antibody binds huTie2 with a KD between about 75 pM and about 200 pM. In some instances, the antibody binds huTie2 with a KD between about 75 pM and about 150 pM. In some instances, the antibody binds huTie2 with a KD between about 75 pM and about 125 pM. In some instances, the antibody binds huTie2 with a KD between about 75 pM and about 100 pM. In some instances, the antibody binds huTie2 with a KD of about 80 pM. In some instances, the antibody binds huTie2 with a KD of about 60 pM. In some instances, the antibody binds huTie2 with a KD of about 40 pM.

In one embodiment, KD is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER™ multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (see Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20™) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, KD is measured using a BIACORE™ surface plasmon resonance (SPR) assay. For example, an assay using a BIACORE™-2000 or a BIACORE™-3000 (BIAcore, Inc., Piscataway, N.J.) is performed at 25° C. with immobilized antigen CM5 chips at about 10 response units (RU). In one embodiment, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (about 0.2 μM) before injection at a flow rate of 5

µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN™-20) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE™ Evaluation Software version 3.2) by simultaneously fitting the association and dissociation sensorgrams. The equilibrium dissociation constant (KD) is calculated as the ratio $k_{off}/k_{on}$. See, for example, Chen et al., J. Mol. Biol. 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette. KD may also be measured using a BIACORE™ SPR assay, known in the art.

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al., Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

In some instances, an anti-Tie2 antibody of the invention provided herein is a Fab.

In some instances, the Fab binds to Tie2 and may include at least one, two, three, four, five, or six CDRs selected from (a) a CDR-H1 comprising the amino acid sequences of any one of SEQ ID NOs: 1-40; (b) a CDR-H2 comprising the amino acid sequence of any one of SEQ ID Nos: 41-80; (c) a CDR-H3 comprising the amino acid sequence of any one of SEQ ID NOs: 81-120; (d) a CDR-L1 comprising the amino acid sequence of any one of SEQ ID NOs: 121-160; (e) a CDR-L2 comprising the amino acid sequence of any one of SEQ ID NOs: 161-200; and (f) a CDR-L3 comprising the amino acid sequence of any one of SEQ ID NOs: 201-240, or a combination of one or more of the above CDRs and one or more variants thereof having at least about 95% sequence identity (e.g., at least 95%, 96%, 97%, 98%, or 99% identity) to any one of SEQ ID NOs: 1-240.

In some instances, the Fab binds to Tie2 and comprises HCDRs 1-3 and LCDRs 1-3 comprising the SEQ ID Nos amino acid sequences as the following antibody clones:

| Antibody Clone # | HCDR1 SEQ ID No. | HCDR2 SEQ ID No. | HCDR3 SEQ ID No. | LCDR1 SEQ ID No. | LCDR2 SEQ ID No. | LCDR3 SEQ ID No. |
|---|---|---|---|---|---|---|
| 3 | 1 | 41 | 81 | 121 | 161 | 201 |
| 8 | 2 | 42 | 82 | 122 | 162 | 202 |
| 9 | 3 | 43 | 83 | 123 | 163 | 203 |
| 10 | 4 | 44 | 84 | 124 | 164 | 204 |
| 4 | 5 | 45 | 85 | 125 | 165 | 205 |
| 11 | 6 | 46 | 86 | 126 | 166 | 206 |
| 12 | 7 | 47 | 87 | 127 | 167 | 207 |
| 13 | 8 | 48 | 88 | 128 | 168 | 208 |
| 14 | 9 | 49 | 89 | 129 | 169 | 209 |
| 15 | 10 | 50 | 90 | 130 | 170 | 210 |
| 16 | 11 | 51 | 91 | 131 | 171 | 211 |
| 17 | 12 | 52 | 92 | 132 | 172 | 212 |
| 18 | 13 | 53 | 93 | 133 | 173 | 213 |
| 19 | 14 | 54 | 94 | 134 | 174 | 214 |
| 20 | 15 | 55 | 95 | 135 | 175 | 215 |
| 21 | 16 | 56 | 96 | 136 | 176 | 216 |
| 22 | 17 | 57 | 97 | 137 | 177 | 217 |
| 23 | 18 | 58 | 98 | 138 | 178 | 218 |
| 24 | 19 | 59 | 99 | 139 | 179 | 219 |
| 25 | 20 | 60 | 100 | 140 | 180 | 220 |
| 1 | 21 | 61 | 101 | 141 | 181 | 221 |
| 26 | 22 | 62 | 102 | 142 | 182 | 222 |
| 27 | 23 | 63 | 103 | 143 | 183 | 223 |
| 28 | 24 | 64 | 104 | 144 | 184 | 224 |
| 29 | 25 | 65 | 105 | 145 | 185 | 225 |
| 30 | 26 | 66 | 106 | 146 | 186 | 226 |
| 6 | 27 | 67 | 107 | 147 | 187 | 227 |
| 2 | 28 | 68 | 108 | 148 | 188 | 228 |
| 31 | 29 | 69 | 109 | 149 | 189 | 229 |
| 5 | 30 | 70 | 110 | 150 | 190 | 230 |
| 32 | 31 | 71 | 111 | 151 | 191 | 231 |
| 33 | 32 | 72 | 112 | 152 | 192 | 232 |
| 39 | 33 | 73 | 113 | 153 | 193 | 233 |
| 22 | 34 | 74 | 114 | 154 | 194 | 234 |
| 34 | 35 | 75 | 115 | 155 | 195 | 235 |
| 35 | 36 | 76 | 116 | 156 | 196 | 236 |
| 36 | 37 | 77 | 117 | 157 | 197 | 237 |
| 37 | 38 | 78 | 118 | 158 | 198 | 238 |
| 38 | 39 | 79 | 119 | 159 | 199 | 239 |
| 40 | 40 | 80 | 120 | 160 | 200 | 240 |

In some instances, the Fab binds to Tie2 and comprises: (a) a VH domain comprising an amino acid sequence having at least about 95% sequence identity (e.g., at least 95%, 96%, 97%, 98%, or 99% sequence identity) to, or has 100% the sequence of, the amino acid sequence of any one of SEQ ID NOs: 242, 244, 246, 248, 250, 252, 254, 256, 258, 260, 262, 264, 266, 268, 270, or 272; and (b) a VL domain comprising an amino acid sequence having at least about 95% sequence identity (e.g., at least 95%, 96%, 97%, 98%, or 99% sequence identity) to, or has 100% the sequence of, the amino acid sequence of any one of SEQ ID NOs: 242, 243, 245, 247, 249, 251, 253, 255, 257, 259, 261, 263, 265, 267, 269, 271, or 273.

In some instances, the Fab binds to Tie2 and comprises a VH domain and a VL domain comprising the amino acid sequences in the following combinations:

| Antibody Clone # | VH Domain SEQ ID No: | VL Domain SEQ ID No: |
|---|---|---|
| 1 | 242 | 243 |
| 2 | 244 | 245 |

-continued

| Antibody Clone # | VH Domain SEQ ID No: | VL Domain SEQ ID No: |
|---|---|---|
| 3 | 246 | 247 |
| 7 | 248 | 249 |
| 41 | 250 | 251 |
| 42 | 252 | 253 |
| 43 | 254 | 255 |
| 44 | 256 | 257 |
| 45 | 258 | 259 |
| 46 | 260 | 261 |
| 6 | 262 | 263 |
| 47 | 264 | 265 |
| 48 | 266 | 267 |
| 5 | 268 | 269 |
| 49 | 270 | 271 |
| 31 | 272 | 273 |

In certain embodiments, an antibody provided herein is a chimeric antibody. Certain chimeric antibodies are described, for example, in U.S. Pat. No. 4,816,567; and Morrison et al., Proc. Natl. Acad. Sci. USA, 81:6851-6855 (1984). In one example, a chimeric antibody comprises a non-human variable region (e.g., a variable domain derived from a mouse, rat, hamster, rabbit, or non-human primate, such as a monkey) and a human constant domain. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which CDRs, for example, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, for example, in Almagro and Fransson, Front. Biosci. 13:1619-1633 (2008), and are further described, for example, in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al., J. Immunol. 151:2296 (1993)); framework regions derived from the consensus sequence of human antibodies of a particular subgroup of light or heavy chain variable regions (see, e.g., Carter et al., Proc. Natl. Acad. Sci. USA, 89:4285 (1992); and Presta et al., J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

In certain embodiments, an antibody provided herein is a human antibody. Human antibodies can be produced using various techniques known in the art. Human antibodies are described generally in van Dijk et al., Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For review of methods for obtaining human antibodies from transgenic animals, see Lonberg, Nat. Biotech. 23:1117-1125 (2005). See also, for example, U.S. Pat. Nos. 6,075,181 and 6,150,584 describing XENOMOUSE™ technology; U.S. Pat. No. 5,770,429 describing HUANTIBODIES™ technology; U.S. Pat. No. 7,041,870 describing K-M MOUSE™ technology, and U.S. Patent Application Publication No. US 2007/0061900, describing VELOCIMOUSE™ technology, and U.S. Pat. Nos. 9,809,642 and 9,380,769, describing OmniChicken™ technology). Human variable regions from intact antibodies generated by such animals may be further modified, for example, by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222:581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

In certain embodiments, an antibody provided herein is a multispecific antibody, such as, for example, a bispecific antibody, a biparatopic antibody, a trispecific, a tetravalent antibody, a pentavalent antibody, a hexavalent antibody, to name a few examples. Multispecific antibodies are monoclonal antibodies that have binding specificities for at least two different sites. In certain embodiments, bispecific antibodies may bind to two or more different epitopes of Tie2. In certain embodiments, one of the binding specificities is for Tie2 and the other is for any other antigen, such as, for example, VEGF. Bispecific antibodies can be prepared as full-length antibodies or antibody fragments. Any of the anti-Tie2 antibodies described herein may be used to engineer a multispecific antibody.

In some instances, the multispecific anti-Tie2 antibodies of the invention are bispecific antibodies in which one arm binds Tie2 and the other arm binds VEGF. In other embodiments, such bispecific anti-Tie2 antibodies of the invention also have Fc mutations that abrogate ADCC and/or CDC as described herein. Such bispecific antibodies of the invention comprise a heavy chain and a light chain comprising the amino acid sequences in the following combinations:

| Antibody Clone # | Heavy Chain SEQ ID No: | Light Chain SEQ ID No: |
|---|---|---|
| 51 | 276 | 277 |
| 52 | 278 | 279 |
| 53 | 280 | 281 |
| 54 | 282 | 283 |
| 57 | 286 | 287 |
| 58 | 288 | 289 |

In other instances, the multispecific anti-Tie2 antibodies of the invention are fused with a VEGF extracellular trap protein. In still other instances, such multispecific anti-Tie2 antibody fusion proteins also have Fc mutations that abrogate ADCC and/or CDC as described herein. Non-limiting examples of such multispecific antibody fusion proteins comprise the following amino acid sequences:

| Antibody Clone # | SEQ ID No: |
|---|---|
| 55 | 284 |
| 56 | 285 |

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. immunol., 152:5368 (1994)); and preparing trispecific antibodies as described, for example, in Tutt et al., J. Immunol. 147:60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to Tie2 as well as another, different antigen (see, e.g., US 2008/0069820).

In certain embodiments, amino acid sequence variants (e.g., antibody variants including one or more amino acid residue alterations) of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen binding.

In certain embodiments, antibody variants having one or more amino acid substitutions are provided. Sites of interest for substitutional mutagenesis include the CDRs and FRs. Conservative substitutions are contemplated, and such are well-known in the art.

Other amino acid substitutions are described below in reference to amino acid side chain classes. Amino acid substitutions may be introduced into an antibody of interest and the products screened for a desired activity, for example, retained/improved antigen binding, decreased immunogenicity, or improved or decreased ADCC or CDC. Amino acids may be grouped according to common side-chain properties:

(1) hydrophobic: Norleucine, Met, Ala, Val, Leu, Ile:
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues and/or FR residues of a parent antibody (e.g., a humanized or human antibody). Generally, the resulting variant(s) selected for further study will have modifications (e.g., improvements) in certain biological properties (e.g., increased affinity, increased stability, increased expression, altered pi, and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more CDR residues are mutated and the variant antibodies displayed on phage and screened for a particular biological activity (e.g., binding affinity).

Alterations (e.g., substitutions) may be made in CDRs, for example, to improve antibody affinity. Such alterations may be made in CDR "hotspots," i.e., residues encoded by codons that undergo mutation at high frequency during the somatic maturation process (see, e.g., Chowdhury, Methods Mol Biol. 207:179-196 (2008)), and/or residues that contact antigen, with the resulting variant VH or VL being tested for binding affinity. Affinity maturation by constructing and reselecting from secondary libraries has been described, for example, in Hoogenboom et al., in Methods in Molecular Biology 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two or three amino acid substitutions.

In certain embodiments, substitutions, insertions, or deletions may occur within one or more FRs so long as such alterations do not substantially reduce the ability of the antibody to bind antigen. Such alterations may, for example, improve antibody affinity and/or stability (e.g., as assessed by an increased melting temperature).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid residue alteration (e.g., a substitution) at one or more amino acid positions. In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity) but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991).

Non-limiting examples of in vitro assays to assess ADCC activity of a molecule of interest are described in U.S. Pat. No. 5,500,362 (see, e.g., Hellstrom et al., Proc. Nat'l Acad. Sci. USA 83:7059-7063 (1986) and Hellstrom et al., Proc. Nat'l Acad. Sci. USA 82:1499-1502 (1985); U.S. Pat. No. 5,821,337; and Bruggemann et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc., Mountain View, Calif.; and CYTOTOX 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, for example, in an animal model such as that disclosed in Clynes et al., Proc. Nat'l Acad. Sci. USA 95:652-656 (1998). C1q binding assays may also be carried out to confirm that the antibody is unable to bind C1q and hence lacks CDC activity. See, for example, C1q and C3c binding ELISA in WO 2006/029879 and WO 2005/100402. To assess complement activation, a CDC assay may be performed (see, e.g., Gazzano-Santoro et al., J. Immunol Methods 202:163 (1996); Cragg et al., Blood 101:1045-1052 (2003); and Cragg et al., Blood 103:2738-2743 (2004)). FcRn binding and in vivo clearance/half-life determinations can also be performed using methods known in the art (see, e.g., Petkova et al., Int'l. Immunol. 18(12): 1759-1769 (2006)).

Antibodies of the invention may be engineered with reduced effector functions, such as decreased complement-dependent cytotoxicity (CDC), antibody-dependent cellular cytotoxicity (ADCC) and antibody-dependent cellular phagocytosis (ADCP) through a reduced affinity to the human FcγRIIIA and/or FcγRIIA and/or FcγRI and/or C1q binding. In some instances, such reduced effector functions are achieved by amino acid substitutions of one or more of the following Fc region residues: N297, L234, L235, D265 and P329, according to EU numbering as in Kabat. See U.S. Pat. Nos. 6,737,056, 7,332,581 and WO/2012/130831. In some embodiments, the substitution mutation is one or more of N297G, N297A, L234A, L235A, D265A, and/or P329G. In some embodiments, the substitution mutation is an N297A or an N297G substitution mutation. In some embodiments, the substitution mutation includes the so-called "DANA" Fc mutant with substitution of residues D265 and N297 to alanine (U.S. Pat. No. 7,332,581). In some embodiments, the substitution mutation includes the so-called "DANG" mutations having residues substituted as D265A and N297G. In some embodiments, the substitution mutation includes the "LALA" Fc mutant with substitution of residues L234 and L235 to alanine (see Lund, J., et al., (1992) Mol. Immunol., 29, 53-59; and Tamm, A. and Schmidt, R. E. (1997) Int. Rev. Immunol., 16, 57-85). In other embodiments, the substitution mutation includes the "LALA-PG" Fc mutant with substitution of residues L234 and L235 to alanine and the P329 to glycine (see Brünker, P., et al. (2016) Mol. Cancer Ther).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001)).

In some embodiments, substitution mutations are made in the Fc region that result in a hexamerized antibody as described herein. In some embodiments, such a substitution mutation is E430G. In other embodiments, the E430G mutation may be combined with any of the reduced effector function mutations discussed above in order to abrogate CDC functioning and/or ADCC effector function. In one embodiment, the anti-Tie2 antibodies of the invention comprise a heavy chain and a light chain comprising the amino acid sequences harboring an E430G mutation and the L234A, L235A, P329G mutations in the following combination:

| Antibody Clone # | Heavy Chain SEQ ID No: | Light Chain SEQ ID No: |
|---|---|---|
| 50 | 174 | 175 |

Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. Nos. 5,648,260; 5,624,821; and WO 94/29351 concerning other examples of Fc region variants.

The invention also provides immunoconjugates comprising an anti-Tie2 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

In another embodiment, an immunoconjugate comprises an antibody as described herein conjugated to a non-cytotoxic agent, such as, for example, the artemisinins, such as artusenate, or cannabinoids, or naltrexone, or aspirin, or statins, or metabolic agents, such as metformin, doxycycline and anthelmintic.

Conjugates of an antibody and cytotoxic or non-cytotoxic agents may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to, such conjugates prepared with cross-linker reagents including, but not limited to, BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

In one aspect, anti-Tie2 antibodies of the invention are useful for detecting the presence of Tie2 in a biological sample. The term "detecting" as used herein encompasses quantitative or qualitative detection. In certain embodiments, a biological sample comprises a cell or tissue. In certain embodiments, such tissues include normal and/or cancerous tissues that express Tie2 at higher levels relative to other tissues.

In one embodiment, an anti-Tie2 antibody for use in a method of diagnosis or detection is provided. In a further aspect, a method of detecting the presence of Tie2 in a biological sample is provided. In certain embodiments, the method comprises contacting the biological sample with an anti-Tie2 antibody as described herein under conditions permissive for binding of the anti-Tie2 antibody to Tie2 and detecting whether a complex is formed between the anti-Tie2 antibody and Tie2. Such method may be an in vitro or in vivo method. In one embodiment, an anti-Tie2 antibody is used to select subjects eligible for therapy with an anti-Tie2 antibody, e.g. where Tie2 is a biomarker for selection of patients.

Any of the antibodies (e.g., anti-Tie2 antibodies) described herein may be produced using recombinant methods and compositions, for example, as described in U.S. Pat. No. 4,816,567. In one embodiment, an isolated nucleic acid encoding an anti-Tie2 antibody described herein is provided. Such a nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such a nucleic acid are provided. In a further embodiment, a host cell comprising such a nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, for example, a Chinese Hamster Ovary (CHO) cell or lymphoid cell (e.g., YO, NSO, Sp20 cell). In one embodiment, a method of making an anti-Tie2 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Tie2 antibody, nucleic acid encoding an antibody, for example, as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, for example, U.S. Pat. Nos. 5,648,237, 5,789,199, and 5,840,523. See also Charlton, Methods in Molecular Biology, Vol. 248 (B. K. C. Lo, ed., Humana Press, Totowa, N.J., 2003), pp. 245-254, describing expression of antibody fragments in *E. coli*. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, for example, U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells ($T_{M4}$ cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as YO, NSO and Sp2/0. For a review of certain mammalian host cell lines suitable for antibody production, see, for example, Yazaki and Wu, Methods in Molecular Biology, Vol. 248 (B. K. C. Lo, ed., Humana Press, Totowa, N.J.), pp. 255-268 (2003).

The anti-Tie2 antibodies provided herein may be identified, screened for, or characterized for their physical/chemical properties and/or biological activities by various assays known in the art and described herein in the Examples and throughout the specification.

In one aspect, an antibody of the invention is tested for its antigen binding activity, e.g., by known methods such as ELISA, Western blot, surface plasmon resonance assays (e.g., BIACORE™), etc.

In one aspect, antigen binding activity (e.g., as indicated by KD) is measured using a BIACORE™ surface plasmon resonance (SPR) assay. For example, an assay using a BIACORE™-2000 or a BIACORE™-3000 (BIAcore, Inc., Piscataway, N.J.) is performed at 25° C. with immobilized antigen CM5 chips at about 10 response units (RU). In one embodiment, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (about 0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN™-20) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE™ Evaluation Software version 3.2) by simultaneously fitting the association and dissociation sensorgrams. The equilibrium dissociation constant (KD) is calculated as the ratio $k_{off}/k_{on}$. See, for example, Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette. KD may also be measured using a BIACORE™ SPR assay.

In another aspect, competition assays may be used to identify an antibody that competes with an antibody as described herein for binding to Tie2. In certain embodiments, such a competing antibody binds to the same epitope (e.g., a linear or a conformational epitope) that is bound by an antibody as described herein. Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized Tie2 is incubated in a solution comprising a first labeled antibody that binds to Tie2 and a second unlabeled antibody that is being tested for its ability to compete with the first antibody for binding to Tie2. The second antibody may be present in a hybridoma supernatant. As a control, immobilized Tie2 is incubated in a solution comprising the first labeled antibody but not the second unlabeled antibody. After incubation under conditions permissive for binding of the first antibody to Tie2, excess unbound antibody is removed, and the amount of label associated with immobilized Tie2 is measured. If the amount of label associated with immobilized Tie2 is substantially reduced in the test sample relative to the control sample, then that indicates that the second antibody is competing with the first antibody for binding to Tie2. See Harlow and Lane (1988) Antibodies: A Laboratory Manual ch.14 (Cold Spring Harbor Laboratory, Cold Spring Harbor, N.Y.).

In one aspect, assays are provided for identifying anti-Tie2 antibodies thereof having biological activity. See the Examples section. Biological activity may include, for example, activating, agonizing, increasing, enhancing one or more biological activities of Tie2. Antibodies having such biological activity in vivo and/or in vitro are also provided.

In certain embodiments, an antibody of the invention is tested for such biological activity. In certain embodiments, an anti-Tie2 antibody binds to Tie2 and reduces or inhibits its serine protease activity for one or more Tie2 substrates, including, for example, the H2-Opt substrate, α-casein, β-casein, or BODIPY™ FL casein substrates, known in the art, or any other suitable Tie2 substrate. In certain embodiments, an anti-Tie2 antibody inhibits Tie2 activity with an IC50 of less than 50 nM, 30 nM, 25 nM, 20 nM, 15 nM, 10 nM, 5 nM, 3 nM, 2.5 nM, 2 nM, 1 nM, 800 pM, 600 pM, 500 pM, 400 pM, 300 pM, 200 pM, 100 pM, 50 pM, or less for one or more Tie2 substrates.

In certain embodiments, labeled anti-Tie2 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment of the invention, the antibody need not be labeled, and the presence thereof can be detected using a labeled antibody which binds to the antibody, such as, for example, an anti-horseradish peroxidase antibody, well-known in the art.

The antibodies of the present invention may be employed in any known assay method, such as competitive binding assays, direct and indirect sandwich assays, and immunoprecipitation assays. Zola et al., *Monoclonal Antibodies: A Manual of Techniques*, pp. 147-158 (CRC Press, Inc. 1987).

Competitive binding assays rely on the ability of a labeled standard to compete with the test sample analyze for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyze that are bound to the antibodies may conveniently be separated from the standard and analyze which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, for example, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the sample may be fresh or frozen or may be embedded in paraffin and fixed with a preservative such as formalin, for example.

Pharmaceutical Formulations

Therapeutic formulations of the anti-Tie2 antibody or antibody fragments or variants thereof of the invention or immunoconjugates of the invention or fusion polypeptides of the invention including combinations thereof with an anti-VEGF antibody or a recombinant VEGF fusion protein as provided herein may be prepared for storage as lyophilized formulations or aqueous solutions by mixing the polypeptide having the desired degree of purity with optional "pharmaceutically-acceptable" carriers, excipients, or stabilizers typically employed in the art (all of which are termed "excipients"). For example, buffering agents, stabilizing agents, preservatives, isotonifiers, non-ionic detergents, antioxidants and other miscellaneous additives. See e.g., Remington's Pharmaceutical Sciences, 16$^{th}$ edition, A. Osol, Ed. (1980). Such additives must be nontoxic to the recipients at the dosages and concentrations employed.

Therapeutic Methods and Compositions

Any of the anti-Tie2 antibodies and antibody fragments of the invention or immunoconjugates of the invention or fusion polypeptides of the invention including combinations thereof with an anti-VEGF antibody or a recombinant VEGF fusion protein as provided herein may be used in therapeutic methods for treating, preventing, and/or mitigating various diseases, including any Tie2 dysregulated disease, defined herein.

EXAMPLES

The following are examples of methods and compositions of the invention. It is understood that various other embodiments may be practiced, given the general description provided above.

Example 1: Immunization of Transgenic Chickens to Isolate Fully Human Anti-Tie2 Antibodies Because the extracellular domain (ECD) of the human and chicken Tie2 orthologs are only 62% identical as opposed to the 90% identity observed between murine and human Tie2 orthologs, using chickens to generate Tie2 antibodies will vastly increase the epitope coverage that can be accessed by antibodies.

Antibodies were generated by immunizing proprietary transgenic chickens, OmniChicken® (Crystal Biosciences, Inc; Emeryville, CA) with recombinantly produced and purified human Tie2 ECD. Through the deletion of endogenous immunoglobulin-encoding genes from the chicken genome and their replacement by human immunoglobulin-encoding genes, OmniChickens are "humanized" and can produce fully human antibodies (see U.S. Pat. Nos. 9,809,642 and 9,380,769).

Next, a high throughput single B cell screening and cloning approach, a gel encapsulated microenvironment (GEM) technology (Crystal Bioscience, Inc, Emeryville, CA) was used to rapidly screen millions of B cells for antibodies that specifically bind to Tie2 (see U.S. Pat. Nos. 8,415,173 and 8,030,095). GEM involves co-localizing single antibody secreting B lymphocytes from immunized animals inside a gel micro-droplet containing one or multiple particulate reporters (Mettler Izquierdo et al. 2016). The reporters used were polystyrene beads coated with Tie2 antigen (ECD of human or mouse Tie2 recombinant protein) and/or cells expressing human Tie2. When a Tie2 antibody producing B cell was incorporated into the GEM, binding to antigen coated beads or Tie2-expressing cells was detected using a red fluorescent secondary antibody. Through the use of single B cell cloning technology, many properly paired heavy and light chain variable domains were found. These sequences were cloned into an antibody expression vector. A total of 236 recombinant antibodies were expressed via transient transfection for confirmation of specificity and assessment of functional activity in downstream assays.

Example 2: Primary Antibody Screening

All 236 antibodies generated as described above in Example 1 were tested for binding to recombinant human Tie2 ECD protein using ELISA methods. The majority of the antibodies screened were found to be strong binders by ELISA, many having EC50 values in the low pM range.

Cross-reactivity to mouse Tie2 by binding to recombinant mouse Tie2 ECD protein was used as a primary screen. These binding studies demonstrated that ~90% of the anti-Tie2 antibodies generated were cross-reactive between mouse and human Tie2 proteins, making them potentially suitable for in vivo testing in established animal models.

Next, a screen for recognition and binding to human full-length Tie2 expressed in its native conformation on the plasma membrane of living cells was performed. For these experiments, human umbilical vein endothelial cells (HUVECs) were obtained from donors. Using flow cytometry, ~70% of the antibodies that bound to human Tie2 ECD protein by ELISA also demonstrated binding to native Tie2 expressed on cells [data not shown].

Example 3: Agonistic Antibodies Identified by a Functional Screen

All Tie2 antibodies that bound HUVEC cells as described above in Example 2 were then tested for agonistic properties using a homogeneous immune-assay (AlphaLISA™) screening platform designed to detect antibodies-induced intracellular levels of phosphorylated (activated) ERK (pERK or p42/p44) and phosphorylated (active) Akt (pAkt), both of which are known downstream signal transduction effectors of Tie2.

In this screening method, HUVEC cells were plated in 96 well plates, serum starved for 3 hours, and then treated with Ang1 (positive control), hIgG1 (non-specific human IgG1 negative control antibody) or anti-Tie2 antibodies at a concentration of 180 nM. Following a 20-minute incubation, cells were lysed and lysates were analyzed for the presence of pERK and total ERK, as well as pAkt and total Akt by specific AlphaLISA assays. To be designated as "active agonistic anti-Tie2 antibody", antibodies clones were required to induce Tie2 signaling as determined by increased levels of intracellular pAkt and pERK (normalized to total Akt and total ERK, respectively). Antibodies that were able to induce increased levels of pERK and pAkt levels were ranked based on their activity relative to the levels of pERK and pAkt induced by Ang1 treatment. Antibodies that were capable of increasing pERK and pAkt levels ≥75% of those seen following Ang1 treatment were considered comparable to Ang1 and carried forward for further testing.

Figure 1B:
Figure 1C:

After hits were identified in the primary functional screen, the variable domains from the anti-Tie2 antibodies with the most activity were reformatted onto a different human IgG scaffold more amenable for therapeutic use. Specifically, the variable domains of all lead candidates were cloned into an expression plasmid containing a Fc domain from human IgG1 which contains an asparagine to alanine mutation at amino acid position 297 (N297A). The Tie2 agonist activity of these reformatted antibodies was confirmed in western blot analyses of antibody-induced increase in phospho-Tie2 (pTie2) (FIG. 1A) as well as by the previously described pERK and pAkt (FIGS. 1B and 1C).

Thus, anti-Tie2 antibodies of the invention were found to activate both proximal and distal Tie2 signaling events and were advanced for further studies.

Example 4: Determining Antibody Potency In Vitro

To enable rank-ordering of anti-Tie2 antibodies of the invention based on potency, an assay with high resolution for determining antibody EC50 values was developed.

Figure 2:
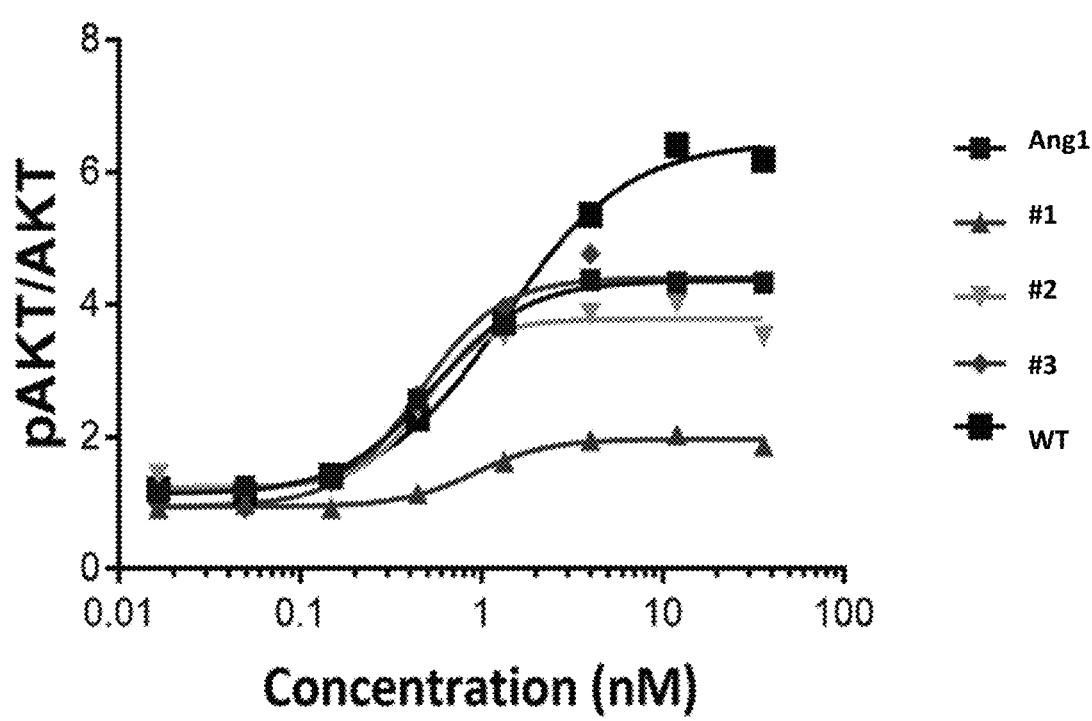
FIG. 2. Functional potencies of anti-Tie2 antibodies are comparable to Ang1 in vitro. HUVEC cells were serum starved and treated with Ang1, human anti-Tie2 antibodies #1, #2, and #3, or WT chicken anti-Tie2 antibody at varying concentrations in nM, followed by cell lysis. Western blotting using pAkt- or total Akt-specific antibodies was performed. pAkt and total Akt signal intensity was measured using a LI-COR scanning fluorometer and levels of pAkt normalized to total Akt (pAkt/Akt ratio) were plotted on Y-axis using Graphpad™ prism software, which was used to determine EC50 values. See Example 4.

In this assay, HUVEC cells were serum starved for 3 hours, then treated with increasing concentrations of Ang1, anti-Tie2 antibodies, or negative control hIgG1 for 20 minutes prior to cell lysis. Cell lysates were then subjected to western blotting and quantitative fluorescence imaging to determine the levels of pAkt relative to total Akt and analyzed to determine respective EC50 values as follows: Ang1=0.54 nM, Ab #1=0.91 nM, Ab #2=0.48 nM, Ab #3=0.45 nM, and WT=1.33 nM. See FIG. 2.

Analysis of EC50 values revealed that most of the antibodies demonstrated potent Tie2 activation at sub-nanomolar concentrations, comparable to the potency of Ang1 in the same assay. Taken together, the functional assays utilized identified anti-Tie2 antibodies that have the ability induce Tie2 signaling to levels comparable to those seen with Ang1.

Figure 3:
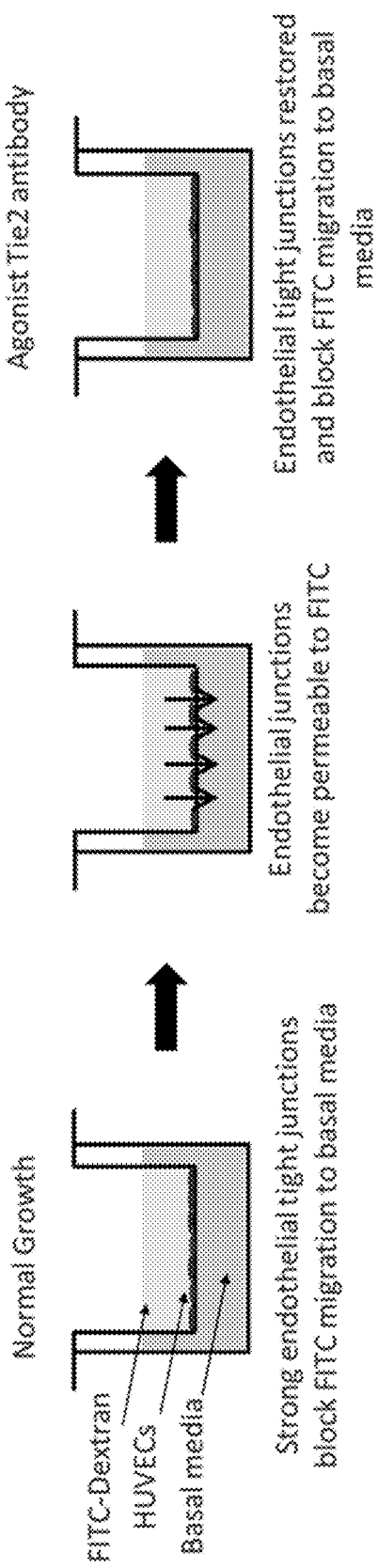
FIG. 3. A schematic of a simplified in vitro model of an endothelial barrier is depicted. See Example 5.

Example 5: Anti-Tie2 Antibodies Decrease Fluid Leak in an In Vitro Model of the Endothelial Barrier In order to investigate the potential physiological effects of anti-Tie2 antibodies on cellular ability to control permeability, a simplified in vitro model of an endothelial barrier was established. This model allowed the further characterization of the antibodies based on their ability to enhance and/or protect physiological permeability induced by increased levels of VEGF in the microenvironment. See FIG. 3 for a schematic of the model set up.

Figure 4:
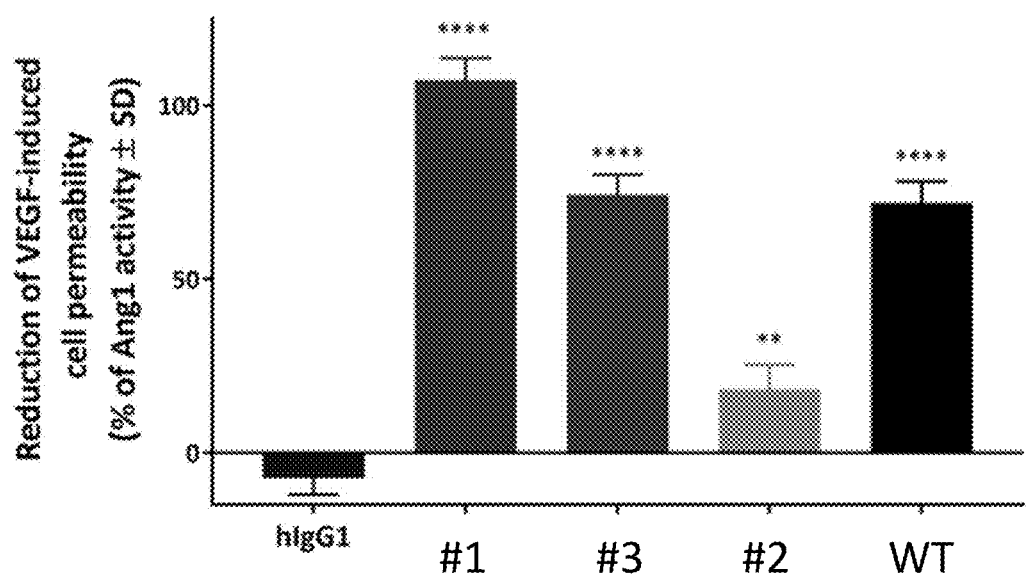
FIG. 4. Anti-Tie2 antibodies are able to reduce VEGF-induced cell permeability in an in vitro model of endothelial barrier leak. Results are represented as % of Ang1 activity (normalized to PBS treated cells). For statistical analyses (using the one-way ANOVA test), the effect of each antibody was compared to the effect of non-specific IgG1 control antibodies. Symbol meaning: $P \le 0.01$; **$\le 0.0001$. See Example 5.

An intact confluent monolayer of HUVEC cells was cultured on a semi-permeable membrane to form an adherent structure with tight junctions. Cells were treated with 100 ng/ml of VEGF with or without Ang1 or anti-Tie2 antibodies. Permeability was assayed at different time points for 6 hours by measuring the amount of fluorescein-conjugated dextran that permeated the cell monolayer into the receiver well below the membrane. The rate of leak was measured as number of fluorescein units accumulated in the receiving well over time. The differential in endothelial barrier leak between PBS (negative control) and Ang1 (positive control) was determined. The ability of anti-Tie2 antibodies to decrease endothelial barrier leak was normalized to the effect Ang1 treatment in the same assay (% Ang1 activity). See FIG. 4.

Statistical analyses revealed that anti-Tie2 antibodies significantly reduced VEGF-induced fluid leak through this matrix of primary endothelial cells, while the human IgG1 negative control did not. Thus, anti-Tie2 antibodies were able to both stimulate downstream Tie2 signaling in biochemical assays and were also able to reduce leak in an orthogonal in vitro physiological assay.

Example 6: Anti-Tie2 Agonist Antibodies Activate Tie2 in the Presence of High Levels of Ang2

Patients suffering from diabetic macular edema (DME) show significantly increased systemic and intravitreal levels of Ang2 (Loukovaara et al. 2013b; Regula et al. 2017). Given the potential for high levels of Ang2 to interfere with anti-Tie2 antibodies activity due to sharing a similar binding site on Tie2 or if binding of an antibody is impacted by an allosteric effect of Ang2 on Tie2 structure, the functional properties of anti-Tie2 antibodies in the presence of saturating concentrations of Ang2 were determined. Ang2 functions as a weak Tie2 agonist able to induce signaling in in vitro assays in the absence of Ang1, albeit at a lower level than can be achieved by Ang1 (Yuan et al. 2009). The in vitro experiments described below corroborated these findings.

Figure 5A:
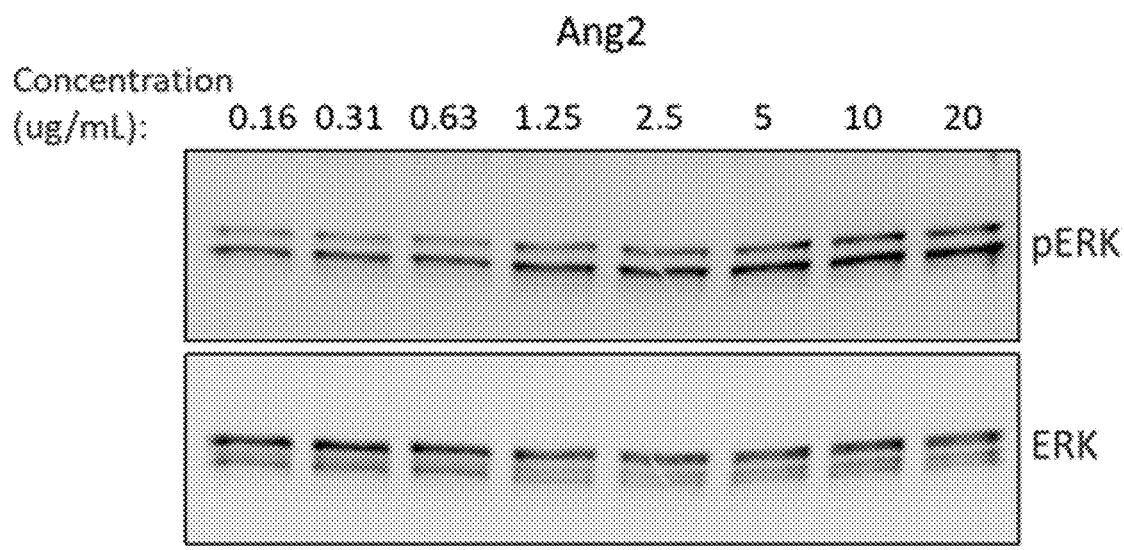
FIGS. 5A to 5F. Anti-Tie2 antibodies in combination with saturating amounts of Ang2 have an additive effect on Tie2 downstream signaling in HUVEC cells. HUVEC cells were serum starved, treated with decreasing amounts of Ang2, lysed, and analyzed for the levels of pERK and total ERK. Normalized values are plotted on the Y-axis; concentrations of Ang2 are plotted on X axis (FIG. 5A). Images were quantitated using a LI-COR scanning fluorometer and pERK levels were normalized to total ERK. Serum starved HUVEC cells were treated with 43 nM Ang2 and 12 nM anti-Tie2 antibodies for 20 minutes. Lysates were submitted to western blotting and images were quantitated for pERK and ERK (FIG. 5C), and pAKT and AKT (FIG. 5E) respectively. pERK (FIG. 5D) and pAKT (FIG. 5F) levels were normalized to total ERK and Akt levels, respectively, to control for equivalent protein loading. See Example 6.
Figure 5B:
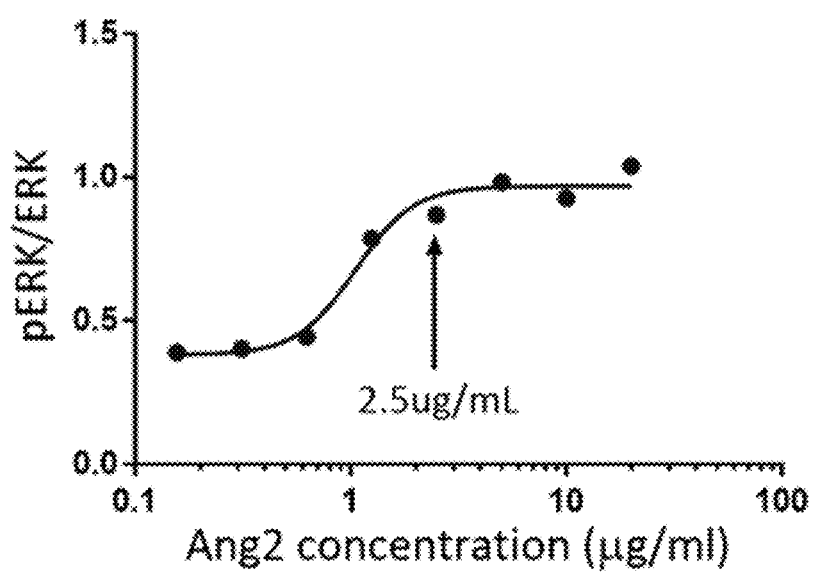
Figure 5C:
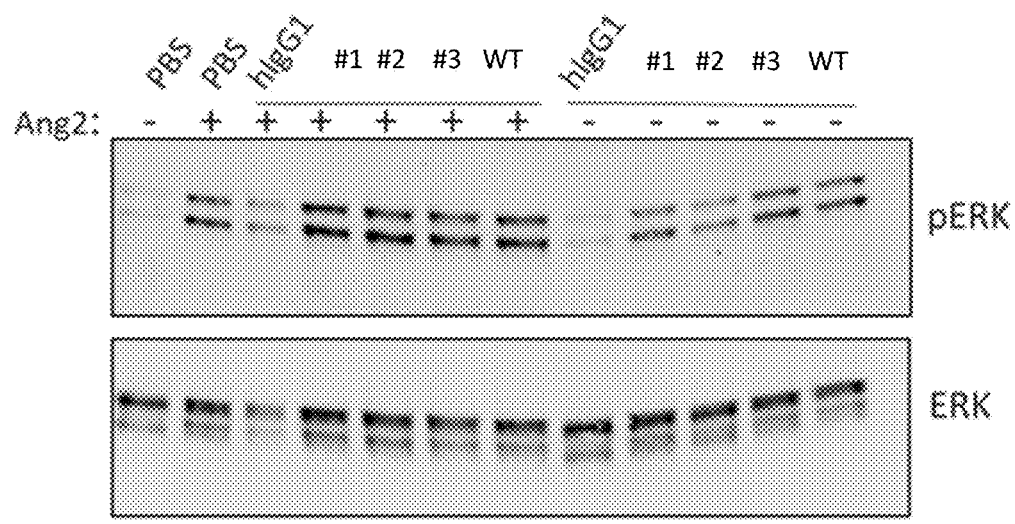
Figure 5D:
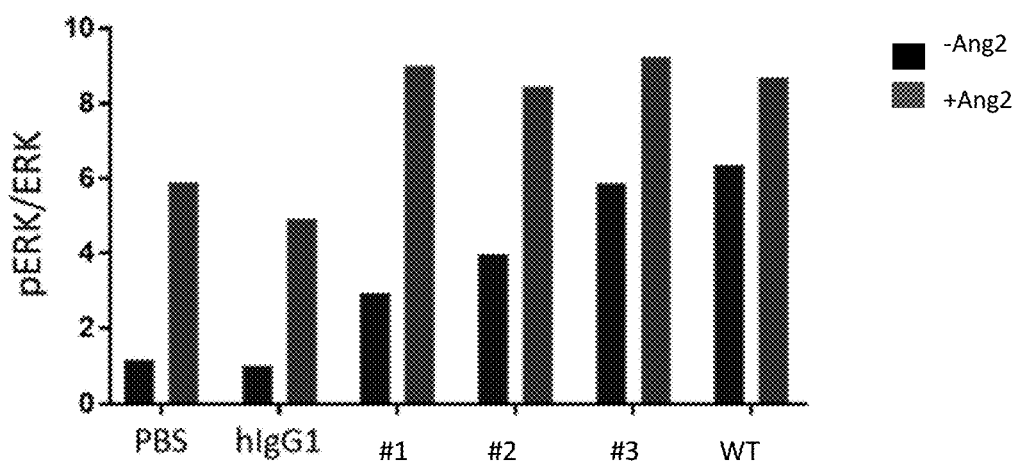
Figure 5E:
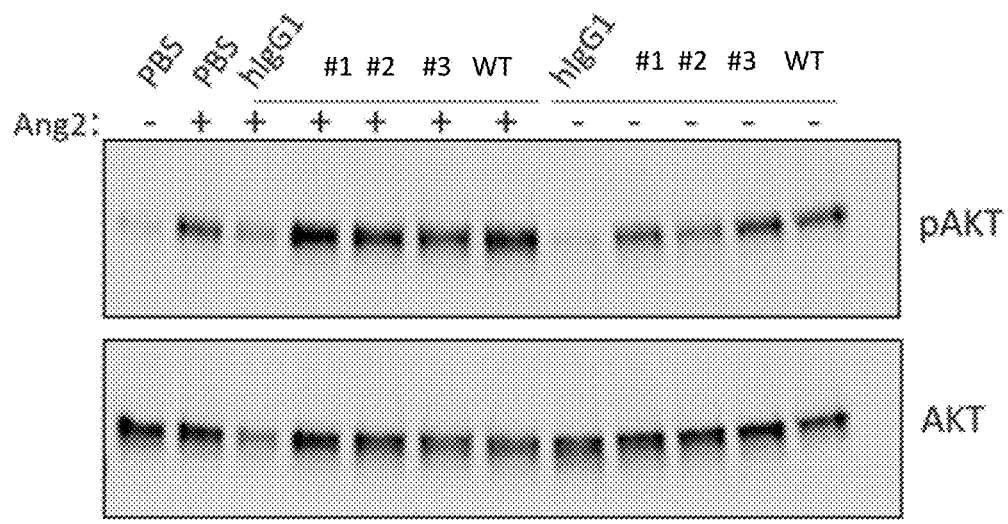
Figure 5F:
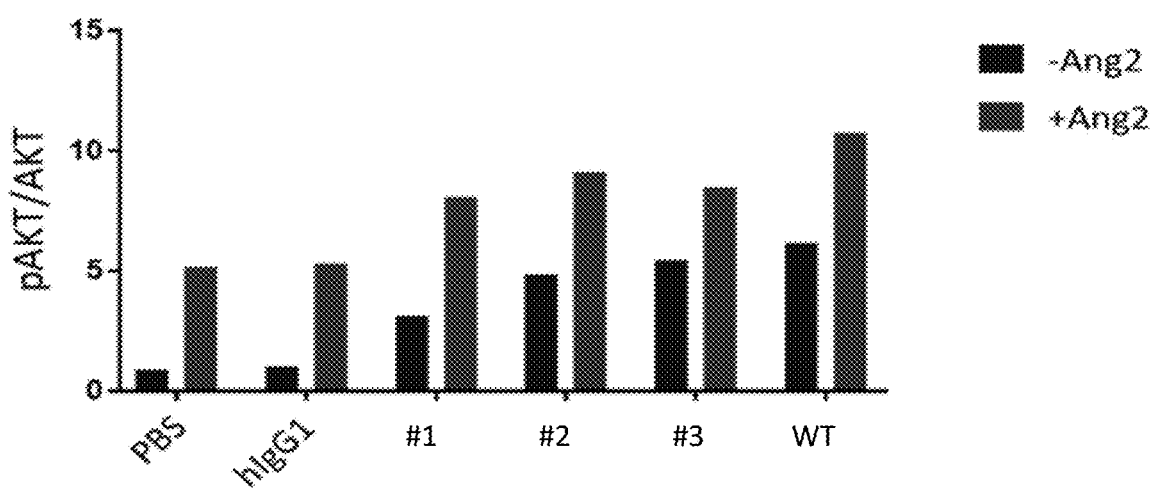

In order to determine saturating levels of Ang2 on Tie2 signaling in an in vitro model system, HUVEC cells were serum starved for 3 hours, treated with increasing concentrations of Ang2, followed by lysis and analysis of pERK/Erk levels by western blotting. See FIG. 4A. Blots were analyzed using quantitative fluorescence imaging and levels of normalized pERK were plotted as a function of Ang2 concentration. The minimum concentration of Ang2 which saturates Tie2 signaling was determined to be 2.5 ug/mL See FIG. 5B. In subsequent experiments, HUVEC cells were co-treated with Ang2 at a concentration of 2.5 ug/mL (43 nM) and anti-Tie2 antibodies at a concentration of 12 nM for 20 minutes before cell lysis and analysis of pErk/Erk (FIGS. 5C and 5D) and pAkt/Akt (FIGS. 5E and 5F) levels.

The results of these experiments demonstrated that anti-Tie2 antibodies are potent Tie2 pathway activators even in the presence of high Ang2 concentrations. Surprisingly, the Tie2 activity in cells exposed to both anti-Tie2 antibodies and Ang2 was higher than the activity seen with either treatment alone.

Example 7: Anti Tie2 Antibodies Utilize a Non-Ligand Competitive Binding Mechanism To further investigate the interplay between the anti-Tie2 antibodies and the angiopoietins at the level of the Tie2 receptor, a competitive binding assay was established using recombinant proteins and biolayer interferometry technology (BLI), a label-free technology for measuring biomolecular interactions.

Figures 6A, 6B:
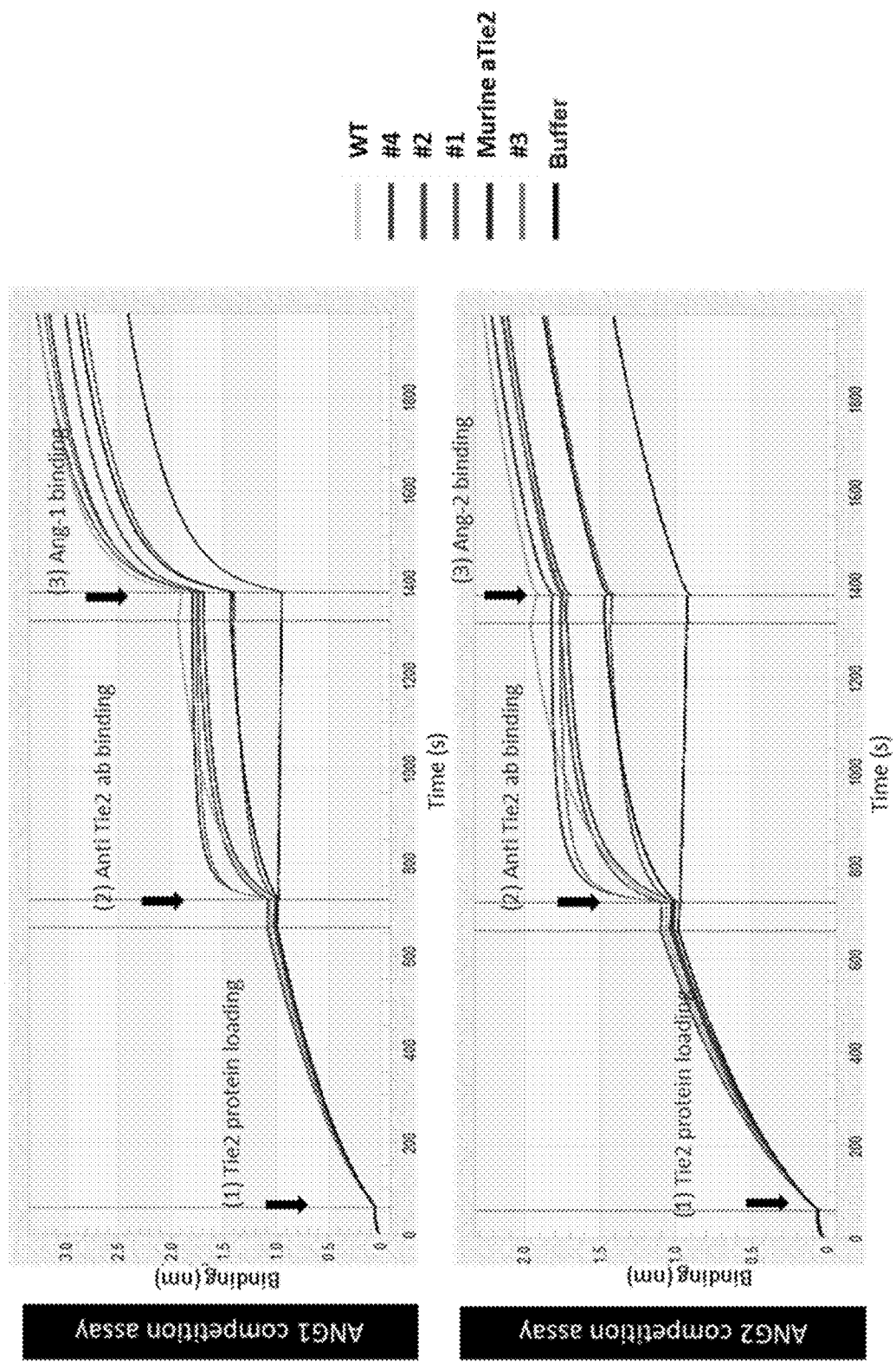
FIGS. 6A to 6B. Anti-Tie2 antibodies do not compete with Ang1 (FIG. 6A) or Ang2 (FIG. 6B) for binding to Tie2 extracellular domain (ECD). Representative competition binding data using biolayer interferometry (BLI) is depicted. The left-side panels show loading of his-tagged Tie2 ECD protein (100 nM) onto the capture biosensor (Ni-NTA) with initiation of exposure indicated by arrow (1), followed by exposure to solutions containing individual anti-Tie2 antibodies (100 nM) as indicated by arrow (2), followed by exposure to solutions containing Ang1 (FIG. 6A) or Ang2 ligand (FIG. 6B) (both at 100 nM) as indicated by arrow (3). Y-axis depicts magnitude of binding to biosensor, x-axis is time elapsed. See Example 7.

In these experiments, recombinant his-tagged Tie2 ECD was captured onto a Ni-NTA biosensor, followed by a sequential exposure to specific anti-Tie2 antibodies and then to Ang1 or Ang2 to assess potential binding competition. In these experiments, Ang1 and Ang2 were able to bind to Tie2 receptors that were pre-complexed with anti-Tie2 antibodies. See FIGS. 6A-B. Thus, the anti-Tie2 agonist antibodies of the invention were found to bind to Tie2 in a non-Ang1 and Ang2 ligand competitive manner and enhance Tie2 signaling in the presence of Ang2 to a higher level than anti-Tie2 antibody alone.

When taken together with the Tie2 pathway signaling results described above, the data characterizing the binding mechanism of the anti-Tie2 antibodies of the invention demonstrates a mode of action that is completely independent of angiopoietin levels.

Example 8: Anti-Tie2 Agonist Antibodies are Cross-Reactive to Tie2 Variants Expressed by Other Animal Species The cross-reactivity profile of anti-Tie2 antibodies to Tie2 orthologs expressed by preclinical animal model species was investigated, using engineered cell lines that overexpress the mouse, rat, rabbit, pig, and cynomolgus monkey Tie2 orthologs.

Briefly, expression plasmids containing the full-length Tie2 coding sequence for each species were used to transfect primary human endothelial cells (HUVECs) as well as human embryonic kidney (HEK293) cells. A stable cell population was selected by treating transfectants with puromycin antibiotic over the course of 2 weeks and single cell clones were generated using fluorescence activated cell sorting. Upon confirmation of cell surface expression of these Tie2 variants, cell lines were used to determine apparent Kd (EC50) values of anti-Tie2 antibodies on the various Tie2 proteins. To obtain this data, cross-reactivity profile of anti-Tie2 antibodies of the invention was determined. Cells were labeled with decreasing concentrations of anti-Tie2 antibodies #1, #2, and #3 (10, 5, 2.5, 1, 25, 0.63, 0.31, and 0.16 ug/mL) or non-specific hIgG1 antibody (10 ug/mL), followed by labeling with a rabbit anti-human IgG antibody conjugated to an Alexa Fluor 488 fluorophore (20 ug/ml). EC50 values were generated using ForeCyt™ software. See Tables 1 and 2.

TABLE 1

Cross-Reactivity Screen (mAb at 10 ug/mL)

| | HEK293 | HEK293/ Human Tie2 | HEK293/ Murine Tie2 | HEK293/ Cyno Tie2 |
|---|---|---|---|---|
| Ab #3 | 0.1 | 40.2 | 32.5 | 40.2 |
| Ab #1 | 0.2 | 60.7 | 0.4 | 74.1 |
| Ab #2 | 0.1 | 64.9 | 41.7 | 53.2 |
| Ab #5 | 0.2 | 60.2 | 0.2 | 73.1 |
| Ab #31 | 0.2 | 65.3 | 28.5 | 47.5 |
| Ab #6 | 0.1 | 63.7 | 0.3 | 78.8 |

TABLE 2

Apparent Kd in nM (EC50 binding)

| | HUVEC | HEK/ huTie2 | HEK/ mTie2 | HEK/ ratTie2 | HEK/ RbTie2 | HEK/ cyno Tie2 |
|---|---|---|---|---|---|---|
| Ab #3 | 1.7 | 1.9 | 6.3 | 4.6 | 3.3 | 3.7 |
| Ab #1 | 2.0 | 8.0 | ND | ND | ND | 7.8 |
| Ab #2 | 1.0 | 2.7 | ND | 1.4 | 4.1 | 7.7 |

These experiments demonstrate the cross-reactive binding of the anti-Tie2 antibodies across human and preclinical species.

Example 9: Anti-Tie2 Antibodies Recognize Distinct Epitopes on Human Tie2

In order to understand the diversity of epitope coverage of the Tie2 antibody panel, anti-Tie2 antibodies were assessed for cross-competition using BLI technology.

Figure 7:
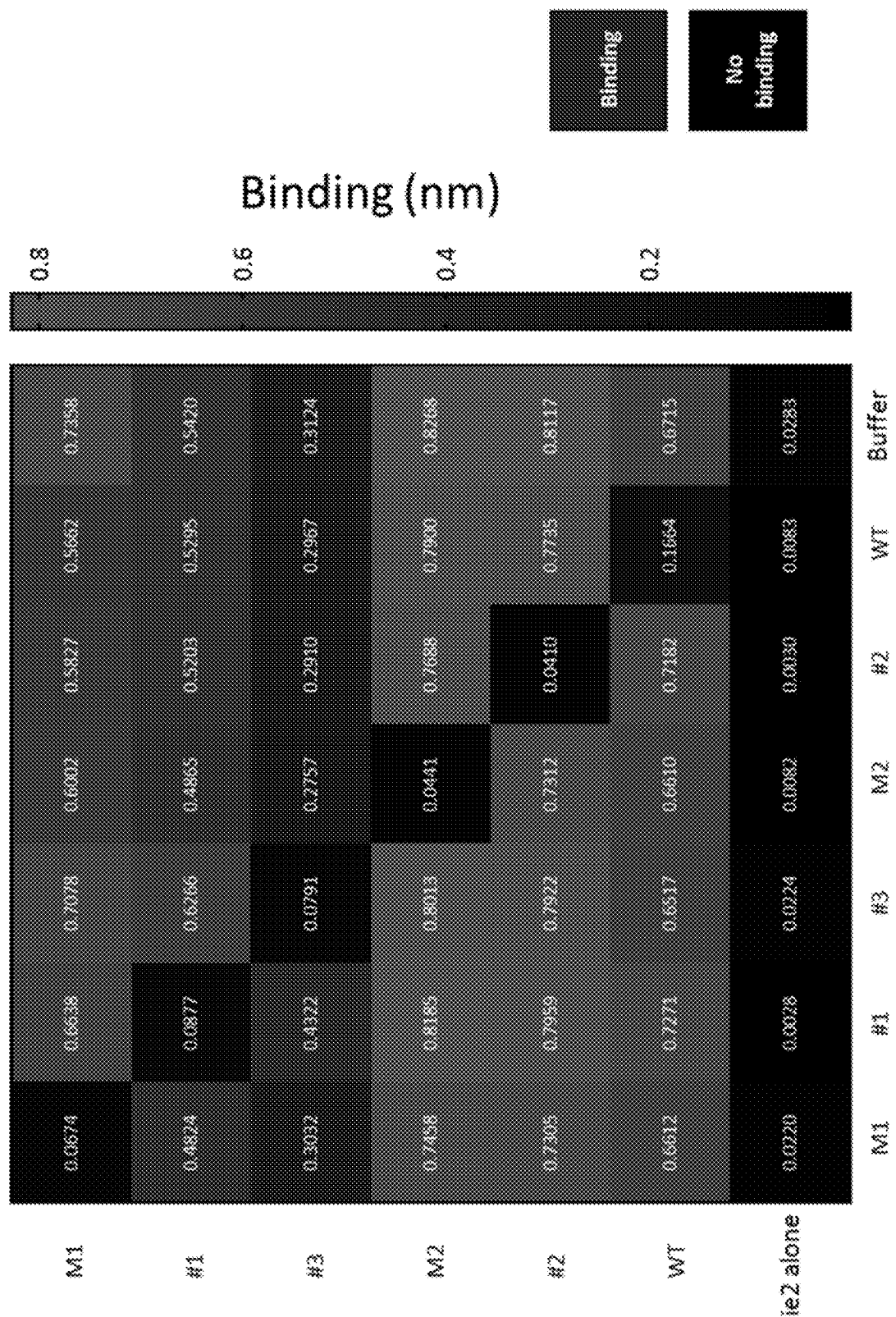
FIG. 7. Anti-Tie2 antibodies show diversity in epitope recognition by BLI binding assessment. Recombinant human Tie2 ECD protein was loaded onto each biosensor, which were subsequently exposed to a solution containing an anti-Tie2 antibody (y-axis), followed by exposure to a 2nd anti-Tie2 antibody (x-axis). Total wavelength shift (in nm) following exposure to the second antibody is annotated in each box in white numbers. Black boxes indicate lack of binding (values <0.2 nm) of the second antibody. Lack of binding was observed only with the same antibody pairs, indicating that all the antibodies tested in this panel bind to different epitopes found on the Tie2 ECD. See Example 9.

Recombinant human Tie2 ECD is loaded onto the biosensor and then exposed to anti-Tie2 antibodies (M1=murine anti-Tie2 mAb; Ab #1; Ab #3; M2=murine anti-Tie2; Ab #2; WT) to assess initial binding. The probe is then exposed to a 2nd anti-Tie2 antibody to assess the second binding event. A positive wavelength shift indicates that the second antibody can bind to the previously formed Tie2-antibody complex, indicating these antibodies bind different epitopes and do not compete for binding to Tie2 protein. Positive wavelength shifts indicating co-binding of two anti-Tie2 antibodies are indicated in grey and light grey, with shift values (nm) embedded in each cell. As expected, antibodies that were pre-bound to Tie2 prevented the binding of the same antibodies to the complex (areas shaded in black). See FIG. 7.

These experiments demonstrated that across a panel of 6 anti-Tie2 agonist antibodies, there was no cross-competition for binding to Tie2, indicating that each candidate recognizes a distinct epitope on the receptor.

Example 10: Oxygen-Induced Retinopathy (OIR) Mouse Model

In this study, 40 C57BL/6J pups at postnatal day 7 (P7) were housed in a hyperoxic chamber (75% $O_2$) for 5 days (n=10 per cage) leading to vessel regression in the center of the retina. CD-1 fostering mothers were rotated before and 2-3 days after entering the chamber. At P12, pups were returned to room air where the relative hypoxia triggers abnormal neovascularization, then endotoxin free 1×PBS vehicle, 10 mg/kg; HuIgG isotype control or 10 mg/kg anti-Tie2 clone #3) were dosed intraperitoneally. At P17, all groups, including naive OIR mice were euthanized. Eyes were enucleated and fixed in 4% paraformaldehyde for 1 hour.

Retinas were dissected and incubated overnight with rhodamine-labeled lectin from *Bandeiraea simplicifolia* (*Griffonia simplicifolia*) (1:100) in 1 mM $CaCl_2$) in PBS to visualize vaso-obliterated (VO) or neovascular (NV) areas. Stained retinas were flat mounted onto slides and imaged on the Zeiss® AxioScan. Images were analyzed on Visiopharm® to determine % VO or % NV of total retina.

Figure 8:
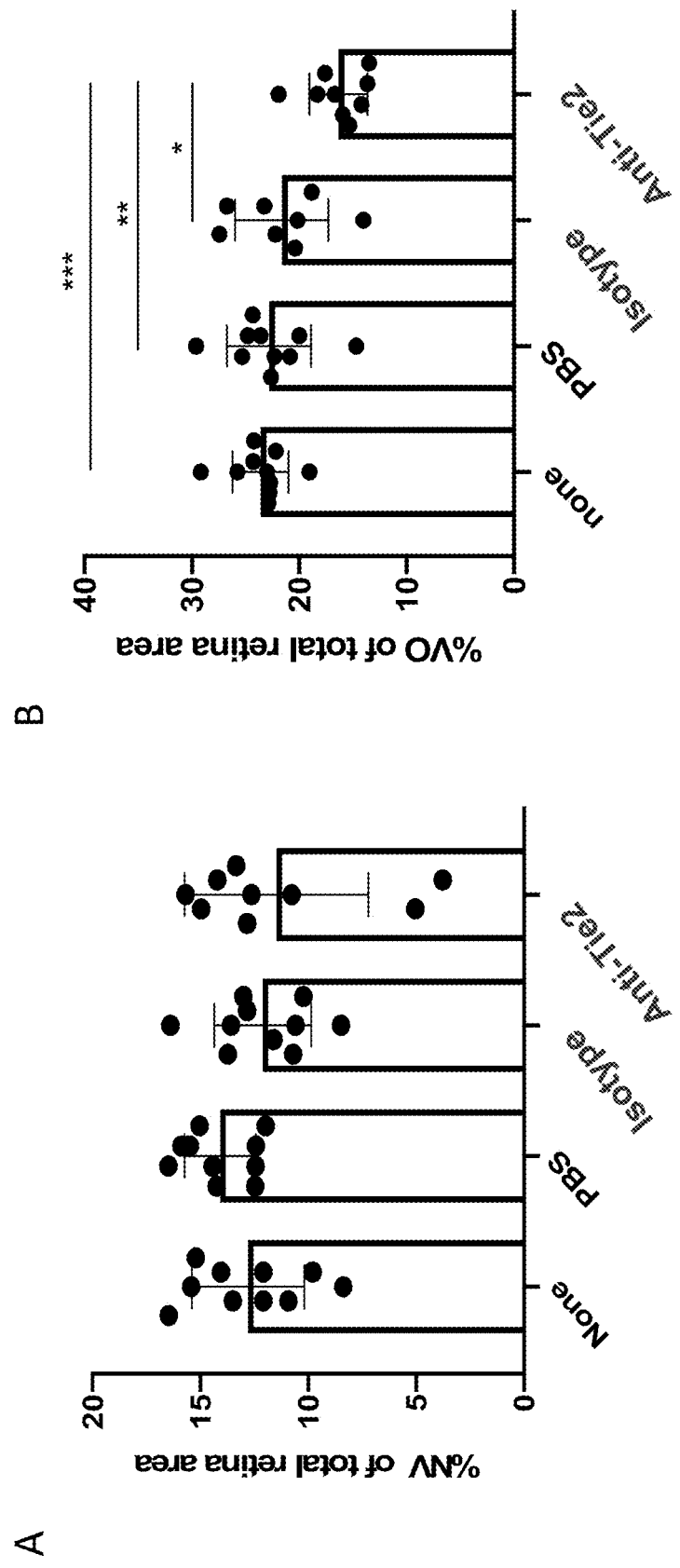
FIG. 8, panels A and B. Systemic administration of an anti-Tie2 antibody did not appear to reduce neovascularization (NV) (FIG. 8, panel A) but reduces vaso-obliteration (VO) in an oxygen-induced retinopathy (OIR) model (FIG. 8, panel B). Each data point represents an average of 2 eyes from single pup. Bars represent means+/−SEM; N=7-8 1-way ANOVA; Tukey's post hoc|*p<0.05; p<0.01; *p<0.001. See Example 10.

As shown in FIG. 8, panel B, anti-Tie2 mAb, but not isotype control mAb or vehicle, was found to have a significant positive impact on the vaso-obliterated (i.e. avascular) area but did not appear to reduce NV (FIG. 8, panel A). The promotion of the regrowth of healthy vasculature may be beneficial to mitigate the adverse consequence of chronic anti-VEGF therapies, such as geographic atrophy or capillary dropout in patients with ocular diseases. See Kim J, et al., Science Advances, Vol. 5 February 13(2019); M. Young, et al., Retina 34, 1308-1315 (2014); T. Kurihara, et al., J. Clin. Invest. 122, 4213-4217 (2012).

Example 11: Laser-Induced Choroidal Neovascularization (CNV) Mouse Model

Male C57BL/6J mice (6-8 week) were anesthetized with a ketamine/xylazine cocktail before laser treatment. CNV lesions were induced by laser photocoagulation using a diode laser (IRIDEX®, Oculight® GL) and a slit lamp (Zeiss®) with a spot size of 50 urn, power of 180 mW and exposure duration of 100 ms. Four laser burns were typically induced at 3, 6, 9 and 12 o'clock position around the optic disc in each eye. A Tie2-specific (clone #3) or isotype control antibodies or an anti-mouse VEGF control antibody (B20) were injected (10 mg/kg) intraperitoneally one day before laser induction and a total of 3 injections was performed every 3 days. Nine days after laser induction, mice were perfused with FITC-lectin or TRITC-dextran via tail vein. 5 minutes after perfusion, eyes were enucleated and fixed in 4% paraformaldehyde (PFA) for 15 min.

Choroid-sclera complexes and retinas were separated and anti-CD31 immunofluorescence (IF) was performed to evidence the vasculature by whole mount staining of both retina and choroidal tissues. For CD31 IF, rat anti-mouse antibody BD 550274 was diluted 1:100 and incubated overnight at 4° C. After 4-hour incubation with a secondary anti-rat antibody (Life Technologies, A11006) whole mounts were imaged at 488 nm. See FIG. 9A. Quantification of neovascularization in lesion area and vascular density in retina was carried out by Image J. P values were assessed by Student's t test (significant change, p<0.05). See FIG. 9B.

Figure 9A:
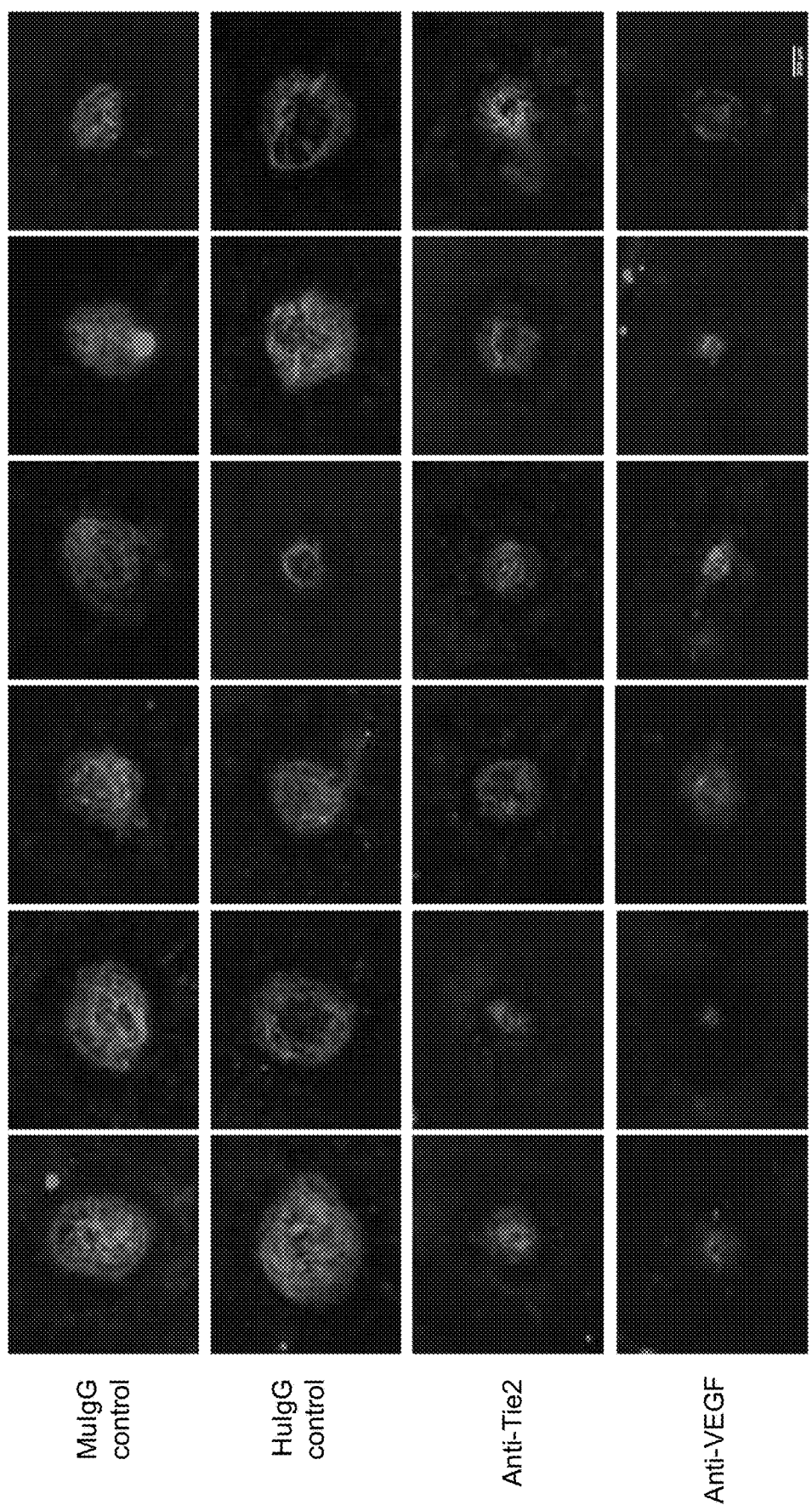

As shown in FIGS. 9A and 9B, the anti-Tie2 antibody, but not isotype control mAb, significantly inhibited choroidal neovascular lesion size following laser injury. This result indicates that the activation of Tie2 following administration of anti-Tie2 mAb has the potential to provide significant clinical benefit to humans afflicted with ophthalmological disorders such as AMD or diabetic retinopathy.

Example 12: Streptozotocin-Induced (STZ) Diabetes Mouse Model

The administration of an agonistic Tie2 antibody of the invention may have utility for the treatment of diabetic retinopathy as well as other morbidities associated with diabetes, such as nephropathy. To explore a potential therapeutic benefit, the impact of anti-Tie2 antibodies of the invention will be tested on disease-relevant endpoints such as vascular leak in the eye, visual function as assessed by electroretinogram, production of cytokines believed to be involved with human disease, such as, for example, IL-1 b, and kidney function as measured by proteinuria in a streptozotocin-induced diabetes mouse model, administered mAb via the intraperitoneal route.

C57BL/6J mice of 6- to 7-weeks in age can be weighed and their baseline glycemia measured (Accu-Chek®, Roche). Mice can be injected intraperitoneally with STZ (Sigma-Aldrich, St. Louis, MO) for 5 consecutive days at 55 mg/kg. Age-matched controls can be injected with buffer only. Glycemia can be measured again a week after the last STZ injection and mice are considered diabetic if their non-fasted glycemia is higher than 17 mM (300 mg/dL). STZ treated diabetic C57BL/6J mice can then be intravitreally (IVT) injected with appropriate amounts of an anti-Tie2 antibody of the invention, a control antibody, vehicle, or a comparator antibody, such as, for example, an anti-VEGF antibody or a recombinant VEGF fusion protein, at least 8 weeks after STZ administration.

Electroretinography (ERG) assesses global retinal cell function using the UTAS-E Visual Electrodiagnostic Test System. After overnight dark adaptation, treated mice are anesthetized with a subcutaneous injection of BW of a cocktail containing ketamine and xylazine in sterile water. One eye is proptosed and the pupil is dilated with tropicamide and phenylephrine FICL. Eyes are kept moist with Genteal® eye drops and core body temperature is maintained using a heating pad. The ERG can be recorded using ultra low impedance silver/nylon DTL Plus electrodes. Needle electrodes can be placed in the middle of the forehead and at the base of the tail. A gold contact lens electrode is used for recording ERG responses. Stimuli can consist of, for example, 50 msec flashes electronically in log steps. Responses are recorded from stimuli that range from below threshold to saturation. Analysis can include a-wave and b-wave maximum amplitudes and thresholds.

Optokinetic tracking (OKT) can also be recorded as follows. Mice can be fixed on a turntable surrounded by a collection of synchronized monitors displaying a vertical black and white grating (14°). Sinusoidal oscillation of the surrounding screens at 1 Hz and 10°/sec peak velocity is applied to induce OKT. Right eye movement is monitored with an infrared-sensitive CCD camera under illumination by an a infrared LED47. The image is sampled at 200 Hz, and the center of the pupil is calculated to estimate the eye position using Morita's Geteye software program. OKT can be recorded for 30 seconds, 3 times with intervals of about 30 seconds.

Retinal vasopermeability can be measured as followed. Mice are anesthetized and injected by tail vein with Evans blue dye dissolved in saline. Two hours after tail vein injection, mice are anesthetized with ketamine and xylazine and can be perfused through the left ventricle using saline. After perfusion, retinas are dissected, weighed and placed in formamide for 18 hours at 70° C. to extract Evans blue dye. On the next day, retinas are centrifuged for 45 minutes and removed from the formamide. Extravasation of Evans blue is measured using a plate reader at A620. A standard curve is used to convert to units of ng Evans blue/wet tissue weight.

Tissue collection for targeted transcriptome can be performed as follows. Mice are sacrificed under anesthesia, and both eyes are enucleated. Retinas are then dissected, placed into RNAlater, and processed for analysis by qRT-PCR.

Example 13: Bispecific Biologics Constructs

Figure 10A:
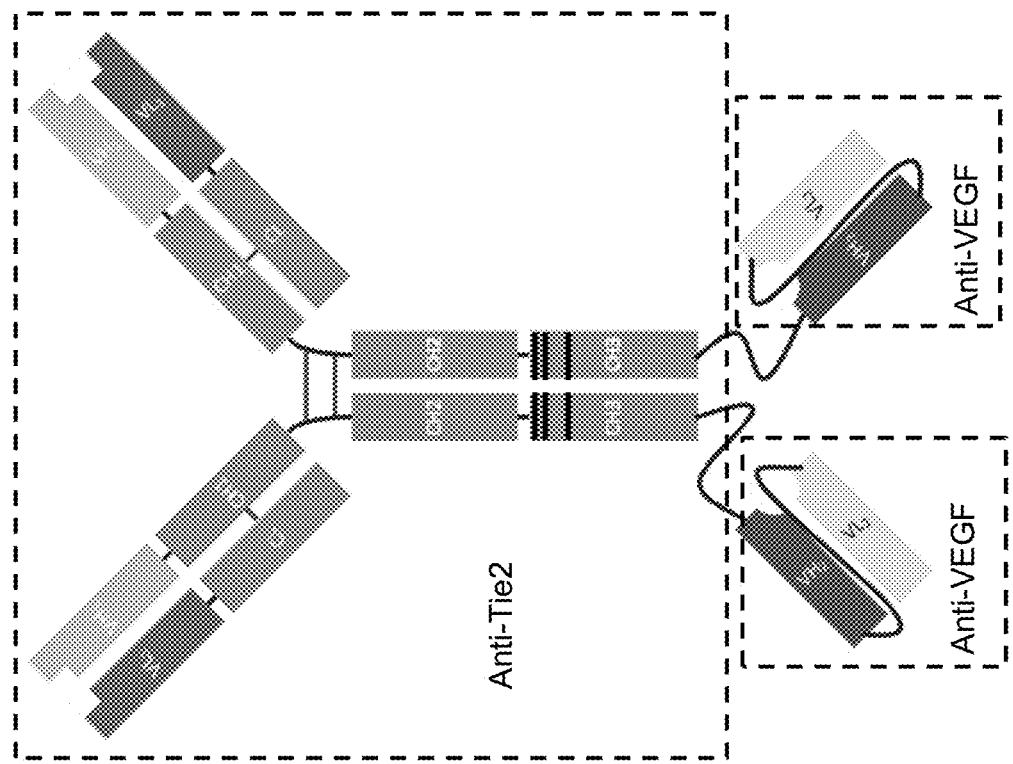

Impacting both the Tie2 and VEGFR-induced signaling pathways simultaneously may have enhanced benefit compared to modulating either pathway alone. To accomplish this, bispecific constructs designed to impact both Tie2 and VEGFR were designed, expressed and tested for activity. FIG. 10A shows an exemplary schematic of the bispecific antibodies of the invention having both Tie2 binding variable domains and VEGF binding variable domains. Antibody clone #54 was designed and generated utilizing standard cloning techniques and has the sequences of SEQ ID Nos:282 and 283. A bispecific construct comprised of the VEGFR R1D2 and R3D3 (VEGF trap proteins) and Tie2 binding domains was also generated (antibody clone #55) and has the sequence of SEQ ID No.284. Tie2 agonism was subsequently assessed for the two exemplary aTie2/VEGF bispecific constructs (antibody clone #54 and #55) using 20 nM of each in HUVEC cells using the AlphaLISA™ screening platform designed to detect antibodies-induced intracellular levels of pERK and pAkt as described in Example 3 above.

Figure 11:
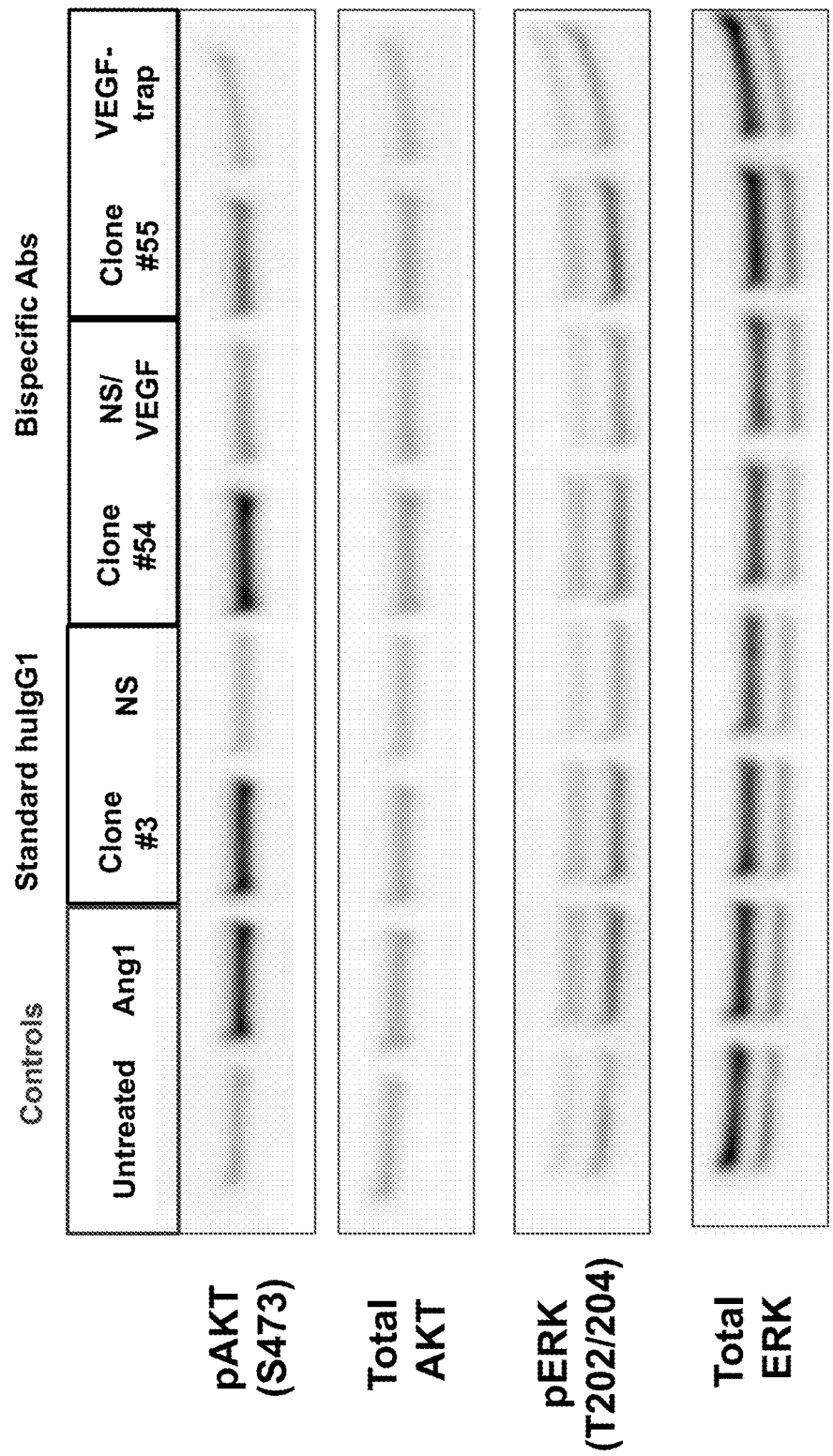
FIG. 11. Tie2 agonism of Tie2/VEGF bispecific constructs was assessed by western blot. Controls used were untreated and an anti-Ang1 antibody (Ang1). Positive controls were an anti-Tie2 antibody clone #3 or a non-specific antibody (NS). Test bispecific antibodies were an anti-Tie2/VEGF bispecific (antibody clone #54) or a non-specific antibody/VEGF bispecific (NS/VEGF) or a VEGF-trap/aTie2 (antibody clone #55) or a VEGF-trap alone. See Examples 3 and 14.

The aTie2/VEGF bispecific constructs tested were found to have the capacity to induce Tie2 signaling in vitro (FIG. 11). These bispecific molecules may allow a patient with ocular disease to receive a single drug to provide substantially more efficacy than VEGF-inhibiting or Tie2-activating monotherapies. The promotion of the regrowth of healthy vasculature provided by the Tie2 agonistic component of the bispecific molecule may also be beneficial to mitigate the potential adverse consequence of the anti-VEGF component of the molecule (i.e. geographic atrophy or capillary dropout, in patients with ocular diseases).

Figure 12:
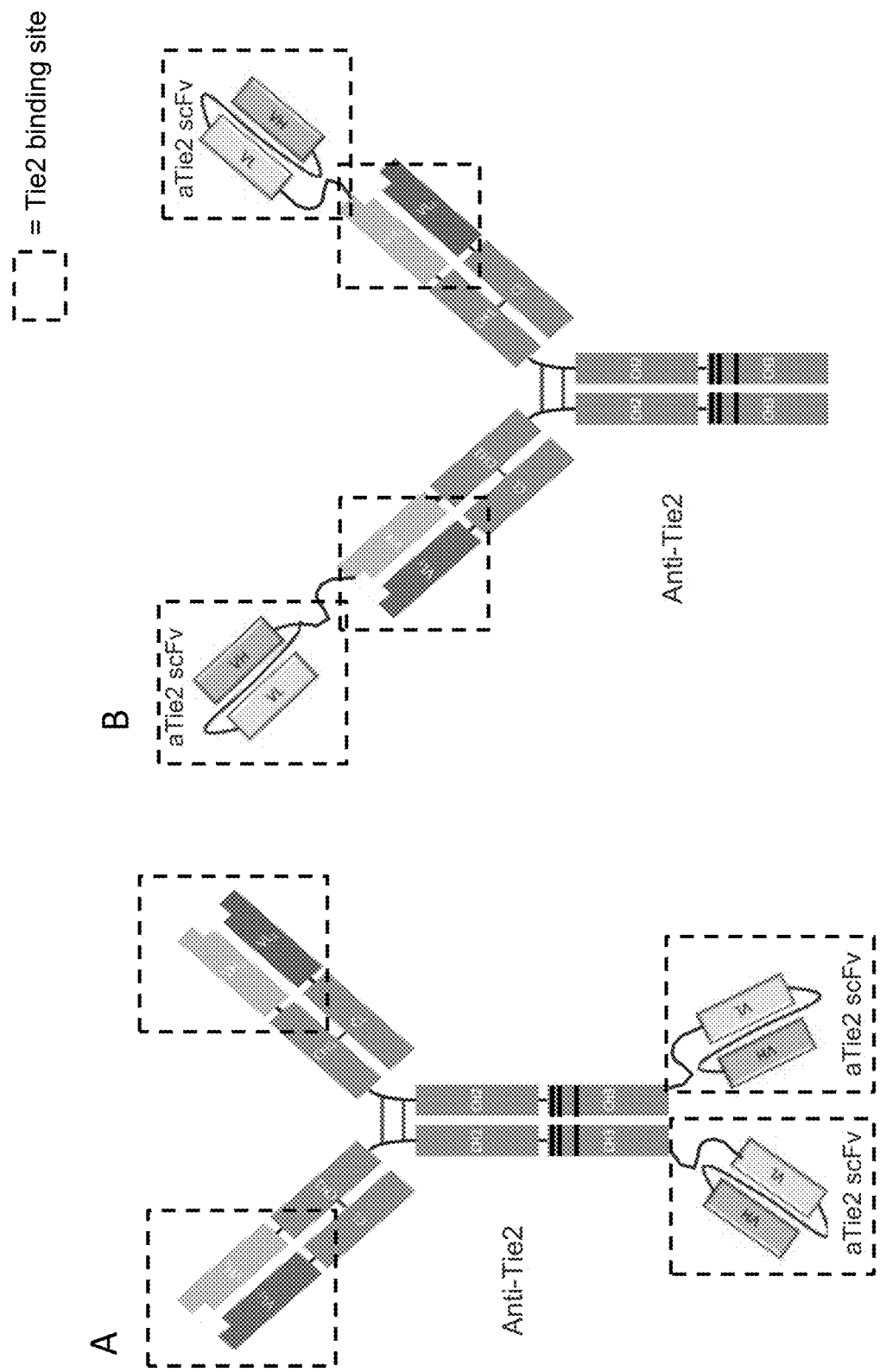
FIG. 12, panels A to C. Schematics of tetravalent and biparatopic anti-Tie2 antibody constructs of the invention to increase valency to Tie2 or cross-link multiple Tie2 epitopes. Exemplary tetravalent anti-Tie2 constructs having sequences of the heavy and light chains of an anti-Tie2 antibody linked via a polypeptide linker to an anti-Tie2 scFv sequence on the C-terminus of the IgG heavy chain (FIG. 12, panel A) or the N-terminus of the heavy chain (FIG. 12, panel B). Exemplary biparatopic anti-Tie2 antibody constructs having sequences of two anti-Tie2 scFvs from one antibody clone (aTie2 scFv B) linked via polypeptide linkers to the C-terminus of the IgG heavy chain of a second, different anti-Tie2 antibody clone (aTie2 Fab A) (FIG. 12, panel C). In all cases, the Tie2 binding site is indicated by the hatched boxes. See Example 15.

Example 14: Anti-Tie2 Antibodies with Increased Valency and Biparatopic Anti-Tie2 Antibodies Antibodies with more than two Tie2 binding moieties, or those which may engage multiple epitopes on the Tie2 extracellular domain, may provide a means to enhance the activation of the Tie2 pathway in vivo to a greater degree than possible by divalent anti-Tie2 antibodies. An exemplary tetravalent anti-Tie2 construct having the sequences of the heavy and light chains of anti-Tie2 antibody clone #3 with the addition of a polypeptide linker and B12 scFv sequence on the C-terminus of the heavy chain (antibody clone #51) or the N-terminus of the heavy chain (antibody clone #52) were generated using standard techniques. See FIG. 12, panels A to C for exemplary schematics.

Figure 14:
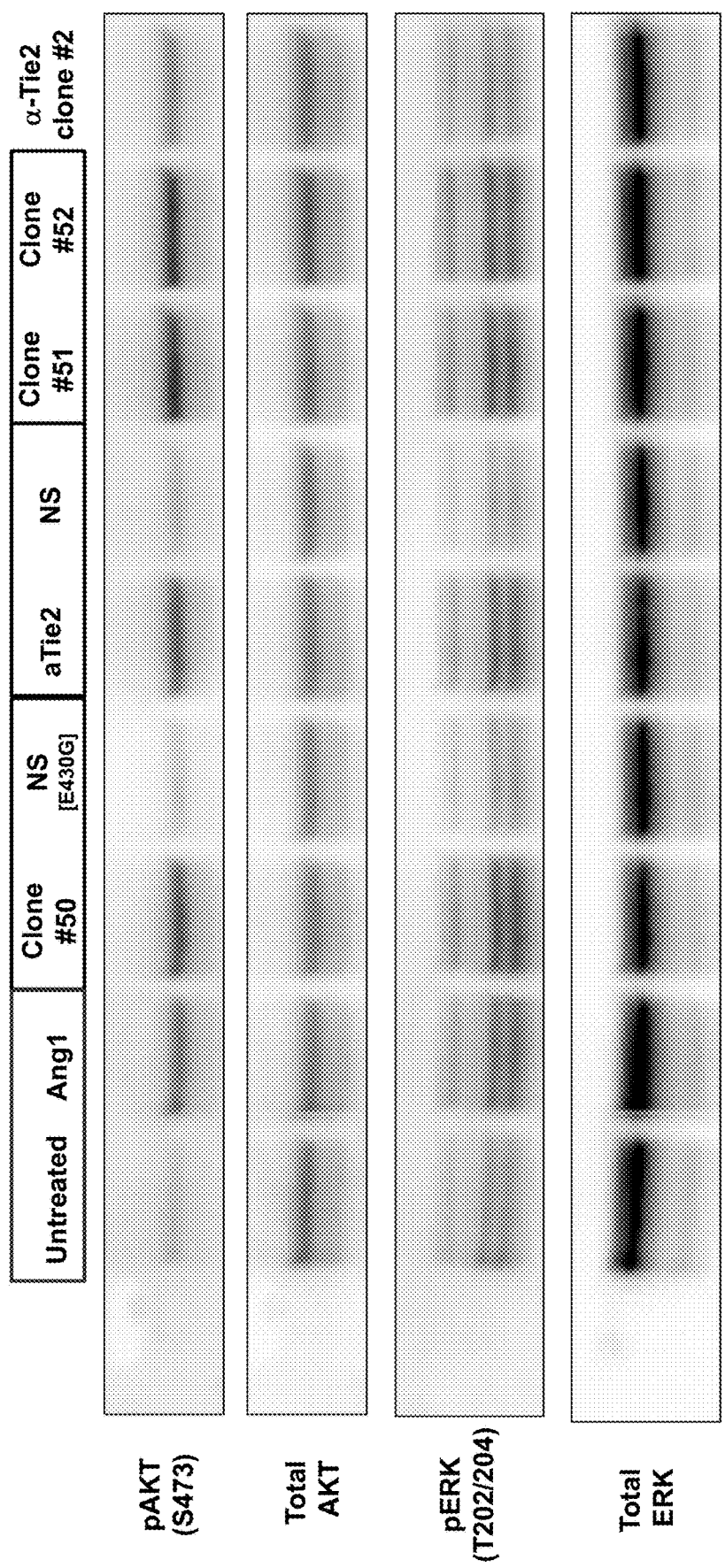
FIG. 14. Tie2 agonism of various anti-Tie2 antibody constructs of the invention were all assessed by a pAKT/pERK western blot. Controls used were untreated, an anti-Ang1 antibody (Ang1), anti-Tie2 antibody clone #3 (aTie2) or a non-specific antibody (NS). Test antibody constructs were a hexamerized anti-Tie2 antibody with the E430G Fc mutation (antibody clone #50) and its control, a non-specific hexamerized antibody (NS E430G), two tetravalent anti-Tie2 antibody constructs (antibody clones #51 and #52), and a divalent anti-Tie2 antibody clone #2. See Examples 3, 14 and 15.

Tetravalent antibody clones #51 and #52 were assessed for their capacity to induce signal transduction through the measurement of pAkt, as described in Example 3. As shown in FIG. 14, both clones #51 and #52 demonstrate an enhanced ability to activate Tie2 signaling in HUVEC cells relative to a divalent anti-Tie2 construct (aTie2) or relative to angiopoietin 1 (Ang1). Thus, anti-Tie2 variants with additional Tie2 binding moieties may provide a means to induce higher order oligomerization of Tie2 on the cell surface and potentially provide therapeutic benefit in contexts where the levels of agonism mediated by a divalent anti-Tie2 antibody or the natural agonistic ligand Ang1 is not adequate to restore vascular homeostasis in diseased tissues.

Figure 13:
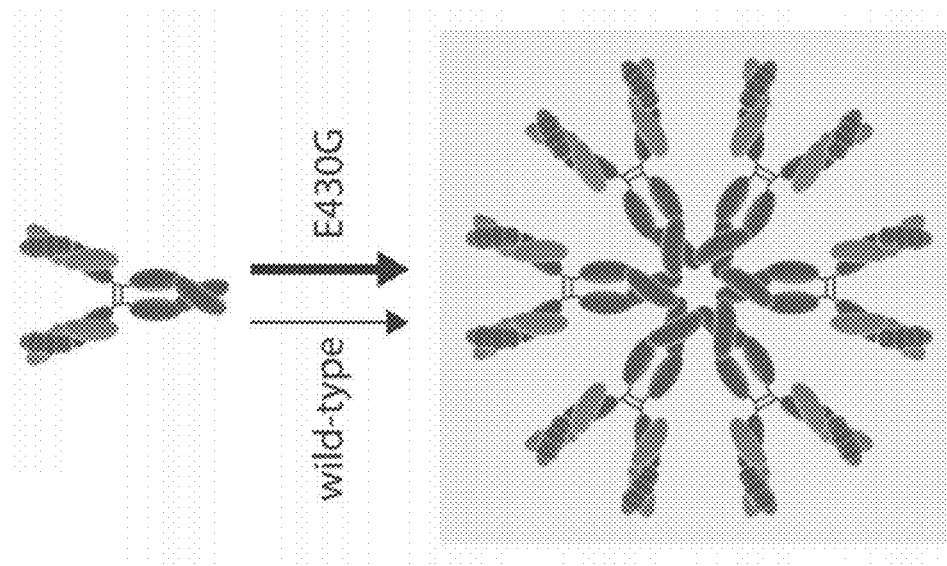
FIG. 13. Schematic of a hexamerized anti-Tie2 antibody construct of the invention to enhance oligomerization and thereby increase agonism of Tie2. An exemplary hexamerized anti-Tie2 construct having sequences of the heavy and light chains of an anti-Tie2 antibody possessing the E430G Fc mutation is shown. See Example 15.

Example 15: Anti-Tie2 Antibodies with Fc Mutations Promoting the Ability to Hexamerize on the Cell Surface Antibodies containing specific mutations in the Fc domain of the heavy chain (i.e. E430G) have been demonstrated to enhance their capacity to form hexamers on the cell surface (M. Overdijk, Mol Cancer Ther 2020; 19:2126-38). An anti-Tie2 antibody containing an Fc domain with a E430G mutation was synthesized and compared to the same anti-Tie2 antibody with a matched Fc containing the native glutamic acid (E) at position 430. See FIG. 13 for a schematic of such a hexamerized anti-Tie2 antibody.

Tie2 agonism was assessed using the pAKT/pERK western blot as described in Example 3. As shown in FIG. 14, the anti-Tie2 E430G construct (antibody clone #50) demonstrated an enhanced ability to induce Tie2 signaling relative to the E430 construct in HUVEC cells. Thus, B12 variants with mutations increasing cell surface hexamerization potential may provide a means to induce higher order oligomerization of Tie2 on the cell surface and potentially provide therapeutic benefit in contexts where the levels of agonism mediated by an anti-Tie2 antibody or the natural agonistic ligand Ang1 is not adequate to restore vascular homeostasis in diseased tissues.

Example 16: Determination of Anti-Tie2 Antibody Fab Binding Affinity by SPR

BIACORE™ (BIAcore, Inc., Piscataway, N.J.) was performed at 25° C. with immobilized human, rat or mouse Tie2 ECD antigens on carboxymethylated dextran biosensor chips (CM5) chips at about 10 response units (RU). CM5 chips were activated with N-ethyl-N'-(3-dimethylaminopropyl)-carbodiimide hydrochloride (EDC) and N-hydroxysuccinimide (NHS) according to the supplier's instructions. All Tie2 ECD antigens were diluted with 10 mM sodium acetate, pH 4.8, to 5 µg/ml (about 0.2 µM) before injection at a flow rate of 5 µl/minute to achieve approximately 10 RU of coupled protein. Following the injection of each Tie2 ECD, 1 M ethanolamine was injected to block unreacted groups. For kinetics measurements, two-fold serial dilutions of the antibody clone #3 Fab (0.78 nM to 500 nM) were injected in PBS with 0.05% polysorbate 20 (TWEEN™-20) surfactant (PBST) at 25° C. at a flow rate of approximately 25 µl/min. Association rates (kon) and dissociation rates (koff) were calculated using a simple one-to-one Langmuir binding model (BIACORE™ Evaluation Software version 3.2) by simultaneously fitting the association and dissociation sensorgrams. The equilibrium dissociation constant (KD) was calculated as the ratio koff/kon. See, for example, Chen et al., J. Mol. Biol. 293:865-881 (1999).

The table below shows the antibody clone #3 Fab binding affinity for each Tie2 ECD antigen tested.

| Antibody | Antigen | Ka $(10^5 \, M^{-1}s^{-1})$ | Kd $(10^{-3}s-1)$ | KD (M) |
|---|---|---|---|---|
| Clone #3 Fab | Human Tie2 ECD | 1.61E+05 | 3.77E-04 | 2.34E-09 |
| | Rat Tie2 ECD | 2.54E+05 | 2.54E+05 | 2.56E-09 |
| | Mouse Tie2 ECD | 2.73E+05 | 8.76E-04 | 3.21E-09 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An isolated anti-Tie2 antibody, or an antigen-binding fragment thereof, comprising three heavy chain complementarity-determining regions (CDR H1-3) of SEQ ID NOS: 1, 41, and 81, respectively, and three light chain CDR regions (CDR L1-3) of SEQ ID NOS: 121, 161, and 201, respectively.

2. The antibody of claim 1, wherein said antibody is fully human, humanized, monoclonal, or chimeric.

3. The antibody of claim 1, wherein said antibody is monospecific.

4. The antibody of claim 1, wherein said antibody is an antibody fragment that specifically binds human Tie2.

5. The antibody of claim 4, wherein the antibody fragment is a Fab, a Fab'-SH, a Fv, a scFv, or a (Fab')$_2$ fragment.

6. The antibody of claim 1, wherein the antibody possesses reduced effector function.

7. The antibody of claim 6, wherein the antibody comprises at least one substitution mutation at amino acid residue N297, L234, L235, P329, D265, and E430 according to EU numbering as in Kabat.

8. The antibody of claim 7, wherein the at least one substitution mutation is selected from the group consisting of amino acid residue N297G or A, L234A, L235A, P329G, D265A, and E430G according to EU numbering as in Kabat.

9. The antibody of claim 8, wherein the antibody comprises the substitution mutation at residue N297A or N297G.

10. The antibody of claim 9, wherein the antibody further comprises the substitution mutation at residue E430G.

11. The antibody of claim 8, wherein the antibody comprises the substitution mutation at residues L234A, L235A and P329G.

12. The antibody of claim 11, wherein the antibody further comprises the substitution mutation at residue E430G.

13. The antibody of claim 8, wherein the antibody comprises the substitution mutation at residues D265A and N297G.

14. The antibody of claim 13, wherein the antibody further comprises the substitution mutation at residue E430G.

15. The antibody of claim 1 conjugated to a cytotoxic agent, a growth inhibitory agent, a toxin or a radioactive isotope.

16. A pharmaceutical composition comprising the antibody of claim 1 and a pharmaceutically acceptable carrier.

17. The pharmaceutical composition of claim 16 further comprising an anti-VEGF antibody or a VEGF extracellular trap protein.

18. An isolated anti-Tie2 antibody, or an antigen-binding fragment thereof comprising
a heavy chain variable (VH) domain comprising SEQ ID NO: 246 and a light chain variable (VL) domain comprising SEQ ID NO: 247.

* * * * *

SEQUENCE LISTING

<160> NUMBER OF SEQ ID NOS: 289

<210> SEQ ID NO 1
<211> LENGTH: 5
<212> TYPE: PRT
<213> ORGANISM: Artificial sequence
<220> FEATURE:
<223> OTHER INFORMATION: human mAb CDR:HC1; clone: p2.3

<400> SEQUENCE: 1

Asp Ser Tyr Gly Met
1               5

<210> SEQ ID NO 2

```
-continued

<211> LENGTH: 5
<212> TYPE: PRT
<213> ORGANISM: Artificial sequence
<220> FEATURE:
<223> OTHER INFORMATION: human mAb CDR:HC1; clone: p2.8

<400> SEQUENCE: 2

Asp Ser Tyr Gly Met
1               5

<210> SEQ ID NO 3
<211> LENGTH: 5
<212> TYPE: PRT
<213> ORGANISM: Artificial sequence
<220> FEATURE:
<223> OTHER INFORMATION: human mAb CDR:HC1; clone: p2.9

<400> SEQUENCE: 3

Ser Val Tyr Gly Met
1               5

<210> SEQ ID NO 4
<211> LENGTH: 5
<212> TYPE: PRT
<213> ORGANISM: Artificial sequence
<220> FEATURE:
<223> OTHER INFORMATION: human mAb CDR:HC1; clone: p2.10

<400> SEQUENCE: 4

Ser Val Tyr Ala Met
1               5

<210> SEQ ID NO 5
<211> LENGTH: 5
<212> TYPE: PRT
<213> ORGANISM: Artificial sequence
<220> FEATURE:
<223> OTHER INFORMATION: human mAb CDR:HC1; clone: p2.4

<400> SEQUENCE: 5

Ser Asn Tyr Val Met
1               5

<210> SEQ ID NO 6
<211> LENGTH: 5
<212> TYPE: PRT
<213> ORGANISM: Artificial sequence
<220> FEATURE:
<223> OTHER INFORMATION: human mAb CDR:HC1; clone: p2.11

<400> SEQUENCE: 6

Gly Val Tyr Gly Met
1               5

<210> SEQ ID NO 7
<211> LENGTH: 5
<212> TYPE: PRT
<213> ORGANISM: Artificial sequence
<220> FEATURE:
<223> OTHER INFORMATION: human mAb CDR:HC1; clone: p2.12

<400> SEQUENCE: 7

Ser Ile Tyr Ala Met
1               5

<210> SEQ ID NO 8
<211> LENGTH: 5
```

```
<212> TYPE: PRT
<213> ORGANISM: Artificial sequence
<220> FEATURE:
<223> OTHER INFORMATION: human mAb CDR:HC1; clone: p2.13

<400> SEQUENCE: 8

Ser Val Tyr Gly Met
1               5

<210> SEQ ID NO 9
<211> LENGTH: 5
<212> TYPE: PRT
<213> ORGANISM: Artificial sequence
<220> FEATURE:
<223> OTHER INFORMATION: human mAb CDR:HC1; clone: p2.14

<400> SEQUENCE: 9

Asp Ile Tyr Gly Met
1               5

<210> SEQ ID NO 10
<211> LENGTH: 5
<212> TYPE: PRT
<213> ORGANISM: Artificial sequence
<220> FEATURE:
<223> OTHER INFORMATION: human mAb CDR:HC1; clone: p2.15

<400> SEQUENCE: 10

Asp Ile Tyr Gly Met
1               5

<210> SEQ ID NO 11
<211> LENGTH: 5
<212> TYPE: PRT
<213> ORGANISM: Artificial sequence
<220> FEATURE:
<223> OTHER INFORMATION: human mAb CDR:HC1; clone: p2.16

<400> SEQUENCE: 11

Ser Asn Tyr Val Met
1               5

<210> SEQ ID NO 12
<211> LENGTH: 5
<212> TYPE: PRT
<213> ORGANISM: Artificial sequence
<220> FEATURE:
<223> OTHER INFORMATION: human mAb CDR:HC1; clone: p2.17

<400> SEQUENCE: 12

Asn Val Tyr Ala Met
1               5

<210> SEQ ID NO 13
<211> LENGTH: 5
<212> TYPE: PRT
<213> ORGANISM: Artificial sequence
<220> FEATURE:
<223> OTHER INFORMATION: human mAb CDR:HC1; clone: p2.18

<400> SEQUENCE: 13

Asp Ile Tyr Gly Met
1               5

<210> SEQ ID NO 14
<211> LENGTH: 5
<212> TYPE: PRT
```

```
<213> ORGANISM: Artificial sequence
<220> FEATURE:
<223> OTHER INFORMATION: human mAb CDR:HC1; clone: p2.19

<400> SEQUENCE: 14

Ser Ile Tyr Ala Met
1               5

<210> SEQ ID NO 15
<211> LENGTH: 5
<212> TYPE: PRT
<213> ORGANISM: Artificial sequence
<220> FEATURE:
<223> OTHER INFORMATION: human mAb CDR:HC1; clone: p2.20

<400> SEQUENCE: 15

Asp Ile Tyr Gly Met
1               5

<210> SEQ ID NO 16
<211> LENGTH: 5
<212> TYPE: PRT
<213> ORGANISM: Artificial sequence
<220> FEATURE:
<223> OTHER INFORMATION: human mAb CDR:HC1; clone: p2.21

<400> SEQUENCE: 16

Ser Val Tyr Gly Met
1               5

<210> SEQ ID NO 17
<211> LENGTH: 5
<212> TYPE: PRT
<213> ORGANISM: Artificial sequence
<220> FEATURE:
<223> OTHER INFORMATION: human mAb CDR:HC1; clone: p1.22

<400> SEQUENCE: 17

Ile Asn Phe Ala Met
1               5

<210> SEQ ID NO 18
<211> LENGTH: 5
<212> TYPE: PRT
<213> ORGANISM: Artificial sequence
<220> FEATURE:
<223> OTHER INFORMATION: human mAb CDR:HC1; clone: p1.23

<400> SEQUENCE: 18

Ser Ser Tyr Ala Met
1               5

<210> SEQ ID NO 19
<211> LENGTH: 5
<212> TYPE: PRT
<213> ORGANISM: Artificial sequence
<220> FEATURE:
<223> OTHER INFORMATION: human mAb CDR:HC1; clone: p1.24

<400> SEQUENCE: 19

Ser Ser Tyr Ala Met
1               5

<210> SEQ ID NO 20
<211> LENGTH: 5
<212> TYPE: PRT
<213> ORGANISM: Artificial sequence
```

```
<220> FEATURE:
<223> OTHER INFORMATION: human mAb CDR:HC1; clone: p1.25

<400> SEQUENCE: 20

Arg Asn Tyr Gly Met
1               5

<210> SEQ ID NO 21
<211> LENGTH: 5
<212> TYPE: PRT
<213> ORGANISM: Artificial sequence
<220> FEATURE:
<223> OTHER INFORMATION: human mAb CDR:HC1; clone: p1.1

<400> SEQUENCE: 21

Ser Ser Tyr Ala Met
1               5

<210> SEQ ID NO 22
<211> LENGTH: 5
<212> TYPE: PRT
<213> ORGANISM: Artificial sequence
<220> FEATURE:
<223> OTHER INFORMATION: human mAb CDR:HC1; clone: p1.26

<400> SEQUENCE: 22

Ser Ser Tyr Ala Met
1               5

<210> SEQ ID NO 23
<211> LENGTH: 5
<212> TYPE: PRT
<213> ORGANISM: Artificial sequence
<220> FEATURE:
<223> OTHER INFORMATION: human mAb CDR:HC1; clone: p1.27

<400> SEQUENCE: 23

Asp Val Tyr Ala Met
1               5

<210> SEQ ID NO 24
<211> LENGTH: 5
<212> TYPE: PRT
<213> ORGANISM: Artificial sequence
<220> FEATURE:
<223> OTHER INFORMATION: human mAb CDR:HC1; clone: p1.28

<400> SEQUENCE: 24

Ser Ser Tyr Ala Met
1               5

<210> SEQ ID NO 25
<211> LENGTH: 5
<212> TYPE: PRT
<213> ORGANISM: Artificial sequence
<220> FEATURE:
<223> OTHER INFORMATION: human mAb CDR:HC1; clone: p1.29

<400> SEQUENCE: 25

Ser Ser Tyr Ala Met
1               5

<210> SEQ ID NO 26
<211> LENGTH: 5
<212> TYPE: PRT
<213> ORGANISM: Artificial sequence
<220> FEATURE:
```

```
<223> OTHER INFORMATION: human mAb CDR:HC1; clone: p1.30

<400> SEQUENCE: 26

Asp Val Tyr Ala Met
1               5

<210> SEQ ID NO 27
<211> LENGTH: 5
<212> TYPE: PRT
<213> ORGANISM: Artificial sequence
<220> FEATURE:
<223> OTHER INFORMATION: human mAb CDR:HC1; clone: p1.6

<400> SEQUENCE: 27

Asp Val Tyr Ala Met
1               5

<210> SEQ ID NO 28
<211> LENGTH: 5
<212> TYPE: PRT
<213> ORGANISM: Artificial sequence
<220> FEATURE:
<223> OTHER INFORMATION: human mAb CDR:HC1; clone: p1.2

<400> SEQUENCE: 28

Ile Asn Phe Ala Met
1               5

<210> SEQ ID NO 29
<211> LENGTH: 5
<212> TYPE: PRT
<213> ORGANISM: Artificial sequence
<220> FEATURE:
<223> OTHER INFORMATION: human mAb CDR:HC1; clone: p1.31

<400> SEQUENCE: 29

Ile Asn Phe Ala Met
1               5

<210> SEQ ID NO 30
<211> LENGTH: 5
<212> TYPE: PRT
<213> ORGANISM: Artificial sequence
<220> FEATURE:
<223> OTHER INFORMATION: human mAb CDR:HC1; clone: p1.5

<400> SEQUENCE: 30

Asp Val Tyr Ala Met
1               5

<210> SEQ ID NO 31
<211> LENGTH: 5
<212> TYPE: PRT
<213> ORGANISM: Artificial sequence
<220> FEATURE:
<223> OTHER INFORMATION: human mAb CDR:HC1; clone: p1.32

<400> SEQUENCE: 31

Asp Val Tyr Ala Met
1               5

<210> SEQ ID NO 32
<211> LENGTH: 5
<212> TYPE: PRT
<213> ORGANISM: Artificial sequence
<220> FEATURE:
<223> OTHER INFORMATION: human mAb CDR:HC1; clone: p1.33
```

```
<400> SEQUENCE: 32

Arg Asn Tyr Gly Met
1               5

<210> SEQ ID NO 33
<211> LENGTH: 5
<212> TYPE: PRT
<213> ORGANISM: Artificial sequence
<220> FEATURE:
<223> OTHER INFORMATION: human mAb CDR:HC1; clone: p1.39

<400> SEQUENCE: 33

Ile Asn Phe Ala Met
1               5

<210> SEQ ID NO 34
<211> LENGTH: 5
<212> TYPE: PRT
<213> ORGANISM: Artificial sequence
<220> FEATURE:
<223> OTHER INFORMATION: human mAb CDR:HC1; clone: p1.22

<400> SEQUENCE: 34

Ile Asn Phe Ala Met
1               5

<210> SEQ ID NO 35
<211> LENGTH: 5
<212> TYPE: PRT
<213> ORGANISM: Artificial sequence
<220> FEATURE:
<223> OTHER INFORMATION: human mAb CDR:HC1; clone: p3.1.34

<400> SEQUENCE: 35

Ser Asn Tyr Ala Met
1               5

<210> SEQ ID NO 36
<211> LENGTH: 5
<212> TYPE: PRT
<213> ORGANISM: Artificial sequence
<220> FEATURE:
<223> OTHER INFORMATION: human mAb CDR:HC1; clone: p3.1.35

<400> SEQUENCE: 36

Ser Ser Tyr Gly Met
1               5

<210> SEQ ID NO 37
<211> LENGTH: 5
<212> TYPE: PRT
<213> ORGANISM: Artificial sequence
<220> FEATURE:
<223> OTHER INFORMATION: human mAb CDR:HC1; clone: p3.1.36

<400> SEQUENCE: 37

Ser Tyr Tyr Ala Met
1               5

<210> SEQ ID NO 38
<211> LENGTH: 5
<212> TYPE: PRT
<213> ORGANISM: Artificial sequence
<220> FEATURE:
<223> OTHER INFORMATION: human mAb CDR:HC1; clone: p3.1.37
```

```
<400> SEQUENCE: 38

Arg Ser Tyr Ala Met
1               5

<210> SEQ ID NO 39
<211> LENGTH: 5
<212> TYPE: PRT
<213> ORGANISM: Artificial sequence
<220> FEATURE:
<223> OTHER INFORMATION: human mAb CDR:HC1; clone: p3.2.38

<400> SEQUENCE: 39

Ser Ser Tyr Gly Met
1               5

<210> SEQ ID NO 40
<211> LENGTH: 5
<212> TYPE: PRT
<213> ORGANISM: Artificial sequence
<220> FEATURE:
<223> OTHER INFORMATION: human mAb CDR:HC1; clone: p3.2.40

<400> SEQUENCE: 40

Ser Tyr Tyr Ala Met
1               5

<210> SEQ ID NO 41
<211> LENGTH: 15
<212> TYPE: PRT
<213> ORGANISM: Artificial sequence
<220> FEATURE:
<223> OTHER INFORMATION: human mAb CDR:HC2; clone: p2.3

<400> SEQUENCE: 41

Ser Ile Asn Val Gly Asp Asn Thr Tyr Tyr Ala Asp Ser Val Arg
1               5                   10                  15

<210> SEQ ID NO 42
<211> LENGTH: 15
<212> TYPE: PRT
<213> ORGANISM: Artificial sequence
<220> FEATURE:
<223> OTHER INFORMATION: human mAb CDR:HC2; clone: p2.8

<400> SEQUENCE: 42

Ser Ile Asn Val Gly Asp Asn Thr Tyr Tyr Ala Asp Ser Val Arg
1               5                   10                  15

<210> SEQ ID NO 43
<211> LENGTH: 16
<212> TYPE: PRT
<213> ORGANISM: Artificial sequence
<220> FEATURE:
<223> OTHER INFORMATION: human mAb CDR:HC2; clone: p2.9

<400> SEQUENCE: 43

Arg Ile Ser Gly Ser Gly Asp Ser Thr Phe Tyr Ala Asp Ser Val Lys
1               5                   10                  15

<210> SEQ ID NO 44
<211> LENGTH: 16
<212> TYPE: PRT
<213> ORGANISM: Artificial sequence
<220> FEATURE:
<223> OTHER INFORMATION: human mAb CDR:HC2; clone: p2.10

<400> SEQUENCE: 44
```

```
Arg Ile Ser Gly Asn Gly Gly Ser Thr Tyr Tyr Ala Asp Ser Val Lys
1               5                   10                  15

<210> SEQ ID NO 45
<211> LENGTH: 16
<212> TYPE: PRT
<213> ORGANISM: Artificial sequence
<220> FEATURE:
<223> OTHER INFORMATION: human mAb CDR:HC2; clone: p2.4

<400> SEQUENCE: 45

Ala Ile Ser His Ser Gly Gly Thr Thr Tyr Tyr Ala Asp Ser Val Glu
1               5                   10                  15

<210> SEQ ID NO 46
<211> LENGTH: 16
<212> TYPE: PRT
<213> ORGANISM: Artificial sequence
<220> FEATURE:
<223> OTHER INFORMATION: human mAb CDR:HC2; clone: p2.11

<400> SEQUENCE: 46

Arg Ile Ser Gly Ser Gly Asp Ser Thr Phe Tyr Ala Asp Ser Val Lys
1               5                   10                  15

<210> SEQ ID NO 47
<211> LENGTH: 16
<212> TYPE: PRT
<213> ORGANISM: Artificial sequence
<220> FEATURE:
<223> OTHER INFORMATION: human mAb CDR:HC2; clone: p2.12

<400> SEQUENCE: 47

Gly Ile Ser Gly Ser Gly Ala Leu Thr Tyr Tyr Ala Asp Ser Val Lys
1               5                   10                  15

<210> SEQ ID NO 48
<211> LENGTH: 16
<212> TYPE: PRT
<213> ORGANISM: Artificial sequence
<220> FEATURE:
<223> OTHER INFORMATION: human mAb CDR:HC2; clone: p2.13

<400> SEQUENCE: 48

Arg Ile Ser Gly Ser Gly Asp Ser Thr Phe Tyr Ala Asp Ser Val Lys
1               5                   10                  15

<210> SEQ ID NO 49
<211> LENGTH: 16
<212> TYPE: PRT
<213> ORGANISM: Artificial sequence
<220> FEATURE:
<223> OTHER INFORMATION: human mAb CDR:HC2; clone: p2.14

<400> SEQUENCE: 49

Arg Ile Ser Val Arg Gly Arg Gly Ala Glu Tyr Ala Asp Ser Val Lys
1               5                   10                  15

<210> SEQ ID NO 50
<211> LENGTH: 16
<212> TYPE: PRT
<213> ORGANISM: Artificial sequence
<220> FEATURE:
<223> OTHER INFORMATION: human mAb CDR:HC2; clone: p2.15

<400> SEQUENCE: 50
```

```
Arg Ile Ser Gly Asn Gly Gly Ser Thr Phe Tyr Ser Glu Ser Val Lys
1               5                   10                  15
```

<210> SEQ ID NO 51
<211> LENGTH: 16
<212> TYPE: PRT
<213> ORGANISM: Artificial sequence
<220> FEATURE:
<223> OTHER INFORMATION: human mAb CDR:HC2; clone: p2.16

<400> SEQUENCE: 51

```
Ala Ile Ser His Ser Gly Gly Thr Thr Tyr Tyr Ala Asp Ser Val Lys
1               5                   10                  15
```

<210> SEQ ID NO 52
<211> LENGTH: 16
<212> TYPE: PRT
<213> ORGANISM: Artificial sequence
<220> FEATURE:
<223> OTHER INFORMATION: human mAb CDR:HC2; clone: p2.17

<400> SEQUENCE: 52

```
Arg Ile Ser Gly Asn Gly Gly Ser Thr Tyr Tyr Ala Glu Ser Val Lys
1               5                   10                  15
```

<210> SEQ ID NO 53
<211> LENGTH: 16
<212> TYPE: PRT
<213> ORGANISM: Artificial sequence
<220> FEATURE:
<223> OTHER INFORMATION: human mAb CDR:HC2; clone: p2.18

<400> SEQUENCE: 53

```
Arg Ile Ser Gly Ser Gly Gly Thr Thr Phe Tyr Ala Glu Ser Val Lys
1               5                   10                  15
```

<210> SEQ ID NO 54
<211> LENGTH: 16
<212> TYPE: PRT
<213> ORGANISM: Artificial sequence
<220> FEATURE:
<223> OTHER INFORMATION: human mAb CDR:HC2; clone: p2.19

<400> SEQUENCE: 54

```
Gly Ile Ser Gly Ser Gly Ala Leu Thr Tyr Tyr Ala Asp Ser Val Lys
1               5                   10                  15
```

<210> SEQ ID NO 55
<211> LENGTH: 16
<212> TYPE: PRT
<213> ORGANISM: Artificial sequence
<220> FEATURE:
<223> OTHER INFORMATION: human mAb CDR:HC2; clone: p2.20

<400> SEQUENCE: 55

```
Arg Ile Ser Val Arg Gly Arg Gly Ala Glu Tyr Ala Asp Ser Val Lys
1               5                   10                  15
```

<210> SEQ ID NO 56
<211> LENGTH: 16
<212> TYPE: PRT
<213> ORGANISM: Artificial sequence
<220> FEATURE:
<223> OTHER INFORMATION: human mAb CDR:HC2; clone: p2.21

<400> SEQUENCE: 56

Arg Ile Ser Gly Ser Gly Asp Ser Thr Phe Tyr Ala Asp Ser Val Lys

```
                1               5                  10                  15

<210> SEQ ID NO 57
<211> LENGTH: 18
<212> TYPE: PRT
<213> ORGANISM: Artificial sequence
<220> FEATURE:
<223> OTHER INFORMATION: human mAb CDR:HC2; clone: p1.22

<400> SEQUENCE: 57

Leu Ile Ser Asp Asp Gly Arg Gly Asn Arg Pro Tyr Tyr Ala Asp Ser
1               5                  10                  15
Val Lys

<210> SEQ ID NO 58
<211> LENGTH: 14
<212> TYPE: PRT
<213> ORGANISM: Artificial sequence
<220> FEATURE:
<223> OTHER INFORMATION: human mAb CDR:HC2; clone: p1.23

<400> SEQUENCE: 58

Arg Ile Ser Asp Tyr Thr Ile Tyr Tyr Ala Asp Ser Val Lys
1               5                  10

<210> SEQ ID NO 59
<211> LENGTH: 14
<212> TYPE: PRT
<213> ORGANISM: Artificial sequence
<220> FEATURE:
<223> OTHER INFORMATION: human mAb CDR:HC2; clone: p1.24

<400> SEQUENCE: 59

Arg Ile Ser Asp Tyr Thr Ile Tyr Tyr Ala Asp Ser Val Lys
1               5                  10

<210> SEQ ID NO 60
<211> LENGTH: 16
<212> TYPE: PRT
<213> ORGANISM: Artificial sequence
<220> FEATURE:
<223> OTHER INFORMATION: human mAb CDR:HC2; clone: p1.25

<400> SEQUENCE: 60

Val Ile Ser Gly Ser Gly Gly Ser Thr Tyr Tyr Ile Asp Ser Val Lys
1               5                  10                  15

<210> SEQ ID NO 61
<211> LENGTH: 14
<212> TYPE: PRT
<213> ORGANISM: Artificial sequence
<220> FEATURE:
<223> OTHER INFORMATION: human mAb CDR:HC2; clone: p1.1

<400> SEQUENCE: 61

Arg Ile Ser Asp Tyr Thr Ile Tyr Tyr Ala Asp Ser Val Lys
1               5                  10

<210> SEQ ID NO 62
<211> LENGTH: 14
<212> TYPE: PRT
<213> ORGANISM: Artificial sequence
<220> FEATURE:
<223> OTHER INFORMATION: human mAb CDR:HC2; clone: p1.26

<400> SEQUENCE: 62
```

-continued

Arg Ile Ser Asp Tyr Thr Ile Tyr Tyr Ala Asp Ser Val Lys
1               5                   10

<210> SEQ ID NO 63
<211> LENGTH: 16
<212> TYPE: PRT
<213> ORGANISM: Artificial sequence
<220> FEATURE:
<223> OTHER INFORMATION: human mAb CDR:HC2; clone: p1.27

<400> SEQUENCE: 63

Leu Ile Ser Gly Thr Gly Arg Met Thr Tyr Tyr Ala Asp Ser Val Lys
1               5                   10                  15

<210> SEQ ID NO 64
<211> LENGTH: 14
<212> TYPE: PRT
<213> ORGANISM: Artificial sequence
<220> FEATURE:
<223> OTHER INFORMATION: human mAb CDR:HC2; clone: p1.28

<400> SEQUENCE: 64

Arg Ile Ser Asp Tyr Thr Ile Tyr Tyr Ala Asp Ser Val Lys
1               5                   10

<210> SEQ ID NO 65
<211> LENGTH: 14
<212> TYPE: PRT
<213> ORGANISM: Artificial sequence
<220> FEATURE:
<223> OTHER INFORMATION: human mAb CDR:HC2; clone: p1.29

<400> SEQUENCE: 65

Arg Ile Ser Asp Tyr Thr Ile Tyr Tyr Ala Asp Ser Val Lys
1               5                   10

<210> SEQ ID NO 66
<211> LENGTH: 16
<212> TYPE: PRT
<213> ORGANISM: Artificial sequence
<220> FEATURE:
<223> OTHER INFORMATION: human mAb CDR:HC2; clone: p1.30

<400> SEQUENCE: 66

Leu Ile Ser Gly Thr Gly Arg Met Thr Tyr Tyr Ala Asp Ser Val Lys
1               5                   10                  15

<210> SEQ ID NO 67
<211> LENGTH: 16
<212> TYPE: PRT
<213> ORGANISM: Artificial sequence
<220> FEATURE:
<223> OTHER INFORMATION: human mAb CDR:HC2; clone: p1.6

<400> SEQUENCE: 67

Leu Ile Ser Gly Thr Gly Arg Met Thr Tyr Tyr Ala Asp Ser Val Lys
1               5                   10                  15

<210> SEQ ID NO 68
<211> LENGTH: 18
<212> TYPE: PRT
<213> ORGANISM: Artificial sequence
<220> FEATURE:
<223> OTHER INFORMATION: human mAb CDR:HC2; clone: p1.2

<400> SEQUENCE: 68

Leu Ile Ser Asp Asp Gly Arg Gly Asn Arg Pro Tyr Tyr Ala Asp Ser

Val Lys

<210> SEQ ID NO 69
<211> LENGTH: 18
<212> TYPE: PRT
<213> ORGANISM: Artificial sequence
<220> FEATURE:
<223> OTHER INFORMATION: human mAb CDR:HC2; clone: p1.31

<400> SEQUENCE: 69

Leu Ile Ser Asp Asp Gly Arg Gly Asn Arg Pro Tyr Tyr Ala Asp Ser
1               5                   10                  15

Val Lys

<210> SEQ ID NO 70
<211> LENGTH: 16
<212> TYPE: PRT
<213> ORGANISM: Artificial sequence
<220> FEATURE:
<223> OTHER INFORMATION: human mAb CDR:HC2; clone: p1.5

<400> SEQUENCE: 70

Leu Ile Ser Gly Thr Gly Arg Met Thr Tyr Tyr Ala Asp Ser Val Lys
1               5                   10                  15

<210> SEQ ID NO 71
<211> LENGTH: 16
<212> TYPE: PRT
<213> ORGANISM: Artificial sequence
<220> FEATURE:
<223> OTHER INFORMATION: human mAb CDR:HC2; clone: p1.32

<400> SEQUENCE: 71

Leu Ile Ser Gly Thr Gly Arg Met Thr Tyr Tyr Ala Asp Ser Val Lys
1               5                   10                  15

<210> SEQ ID NO 72
<211> LENGTH: 16
<212> TYPE: PRT
<213> ORGANISM: Artificial sequence
<220> FEATURE:
<223> OTHER INFORMATION: human mAb CDR:HC2; clone: p1.33

<400> SEQUENCE: 72

Val Ile Ser Gly Ser Gly Gly Ser Thr Tyr Tyr Ile Asp Ser Val Lys
1               5                   10                  15

<210> SEQ ID NO 73
<211> LENGTH: 18
<212> TYPE: PRT
<213> ORGANISM: Artificial sequence
<220> FEATURE:
<223> OTHER INFORMATION: human mAb CDR:HC2; clone: p1.39

<400> SEQUENCE: 73

Leu Ile Ser Asp Asp Gly Arg Gly Asn Arg Pro Tyr Tyr Ala Asp Ser
1               5                   10                  15

Val Lys

<210> SEQ ID NO 74
<211> LENGTH: 18
<212> TYPE: PRT
<213> ORGANISM: Artificial sequence
<220> FEATURE:

```
<223> OTHER INFORMATION: human mAb CDR:HC2; clone: p1.22

<400> SEQUENCE: 74

Leu Ile Ser Asp Asp Gly Arg Gly Asn Arg Pro Tyr Tyr Ala Asp Ser
1               5                   10                  15

Val Lys

<210> SEQ ID NO 75
<211> LENGTH: 21
<212> TYPE: PRT
<213> ORGANISM: Artificial sequence
<220> FEATURE:
<223> OTHER INFORMATION: human mAb CDR:HC2; clone: p3.1.34

<400> SEQUENCE: 75

Ser Ile Ser Gly Asn Gly Ile Ser His Ser Gly Gly Ser Thr Tyr Tyr
1               5                   10                  15

Ala Asp Ser Val Lys
            20

<210> SEQ ID NO 76
<211> LENGTH: 16
<212> TYPE: PRT
<213> ORGANISM: Artificial sequence
<220> FEATURE:
<223> OTHER INFORMATION: human mAb CDR:HC2; clone: p3.1.35

<400> SEQUENCE: 76

Ile Ile Ser Gly Asp Gly Val Ile Thr Ser Tyr Ala Asp Ser Val Lys
1               5                   10                  15

<210> SEQ ID NO 77
<211> LENGTH: 16
<212> TYPE: PRT
<213> ORGANISM: Artificial sequence
<220> FEATURE:
<223> OTHER INFORMATION: human mAb CDR:HC2; clone: p3.1.36

<400> SEQUENCE: 77

Arg Ile Ser Gly Ser Gly Gly Ser Thr Phe Tyr Ala Asp Ser Val Lys
1               5                   10                  15

<210> SEQ ID NO 78
<211> LENGTH: 21
<212> TYPE: PRT
<213> ORGANISM: Artificial sequence
<220> FEATURE:
<223> OTHER INFORMATION: human mAb CDR:HC2; clone: p3.1.37

<400> SEQUENCE: 78

Ser Ile Ser Gly Asn Gly Ile Ser His Ser Gly Gly Ser Thr Tyr Tyr
1               5                   10                  15

Ala Asp Ser Val Lys
            20

<210> SEQ ID NO 79
<211> LENGTH: 16
<212> TYPE: PRT
<213> ORGANISM: Artificial sequence
<220> FEATURE:
<223> OTHER INFORMATION: human mAb CDR:HC2; clone: p3.2.38

<400> SEQUENCE: 79

Ile Ile Ser Gly Asp Gly Val Ile Thr Ser Tyr Ala Asp Ser Val Lys
1               5                   10                  15
```

```
<210> SEQ ID NO 80
<211> LENGTH: 16
<212> TYPE: PRT
<213> ORGANISM: Artificial sequence
<220> FEATURE:
<223> OTHER INFORMATION: human mAb CDR:HC2; clone: p3.2.40

<400> SEQUENCE: 80

Arg Ile Ser Gly Ser Gly Gly Ser Thr Phe Tyr Ala Asp Ser Val Lys
1               5                   10                  15

<210> SEQ ID NO 81
<211> LENGTH: 8
<212> TYPE: PRT
<213> ORGANISM: Artificial sequence
<220> FEATURE:
<223> OTHER INFORMATION: human mAb CDR:HC3; clone: p2.3

<400> SEQUENCE: 81

Trp Asn Ser Phe Phe Asp Tyr Trp
1               5

<210> SEQ ID NO 82
<211> LENGTH: 8
<212> TYPE: PRT
<213> ORGANISM: Artificial sequence
<220> FEATURE:
<223> OTHER INFORMATION: human mAb CDR:HC3; clone: p2.8

<400> SEQUENCE: 82

Trp Asn Ser Phe Phe Asp Tyr Trp
1               5

<210> SEQ ID NO 83
<211> LENGTH: 9
<212> TYPE: PRT
<213> ORGANISM: Artificial sequence
<220> FEATURE:
<223> OTHER INFORMATION: human mAb CDR:HC3; clone: p2.9

<400> SEQUENCE: 83

Thr Trp Asn Asn Phe Phe Asp Tyr Trp
1               5

<210> SEQ ID NO 84
<211> LENGTH: 9
<212> TYPE: PRT
<213> ORGANISM: Artificial sequence
<220> FEATURE:
<223> OTHER INFORMATION: human mAb CDR:HC3; clone: p2.10

<400> SEQUENCE: 84

Thr Leu Asn Asn Phe Phe Asp Tyr Trp
1               5

<210> SEQ ID NO 85
<211> LENGTH: 12
<212> TYPE: PRT
<213> ORGANISM: Artificial sequence
<220> FEATURE:
<223> OTHER INFORMATION: human mAb CDR:HC3; clone: p2.4

<400> SEQUENCE: 85

Asp Leu Gly Tyr Trp Asn Asn Phe Phe Asp Tyr Trp
1               5                   10
```

```
<210> SEQ ID NO 86
<211> LENGTH: 9
<212> TYPE: PRT
<213> ORGANISM: Artificial sequence
<220> FEATURE:
<223> OTHER INFORMATION: human mAb CDR:HC3; clone: p2.11

<400> SEQUENCE: 86

Thr Trp Asn Asn Phe Phe Asp Tyr Trp
1               5

<210> SEQ ID NO 87
<211> LENGTH: 9
<212> TYPE: PRT
<213> ORGANISM: Artificial sequence
<220> FEATURE:
<223> OTHER INFORMATION: human mAb CDR:HC3; clone: p2.12

<400> SEQUENCE: 87

Pro Leu Asn Asn Phe Phe Asp Tyr Trp
1               5

<210> SEQ ID NO 88
<211> LENGTH: 9
<212> TYPE: PRT
<213> ORGANISM: Artificial sequence
<220> FEATURE:
<223> OTHER INFORMATION: human mAb CDR:HC3; clone: p2.13

<400> SEQUENCE: 88

Thr Trp Asn Asn Phe Phe Asp Tyr Trp
1               5

<210> SEQ ID NO 89
<211> LENGTH: 11
<212> TYPE: PRT
<213> ORGANISM: Artificial sequence
<220> FEATURE:
<223> OTHER INFORMATION: human mAb CDR:HC3; clone: p2.14

<400> SEQUENCE: 89

Glu Asn Asn Trp Asn Ser Phe Phe Asp Tyr Trp
1               5                   10

<210> SEQ ID NO 90
<211> LENGTH: 9
<212> TYPE: PRT
<213> ORGANISM: Artificial sequence
<220> FEATURE:
<223> OTHER INFORMATION: human mAb CDR:HC3; clone: p2.15

<400> SEQUENCE: 90

Thr Leu Asn Asn Phe Phe Asp Tyr Trp
1               5

<210> SEQ ID NO 91
<211> LENGTH: 12
<212> TYPE: PRT
<213> ORGANISM: Artificial sequence
<220> FEATURE:
<223> OTHER INFORMATION: human mAb CDR:HC3; clone: p2.16

<400> SEQUENCE: 91

Asp Leu Gly Tyr Trp Asn Asn Phe Phe Asp Tyr Trp
1               5                   10
```

<210> SEQ ID NO 92
<211> LENGTH: 9
<212> TYPE: PRT
<213> ORGANISM: Artificial sequence
<220> FEATURE:
<223> OTHER INFORMATION: human mAb CDR:HC3; clone: p2.17

<400> SEQUENCE: 92

Thr Trp Asn Asn Phe Phe Asp Tyr Trp
1               5

<210> SEQ ID NO 93
<211> LENGTH: 9
<212> TYPE: PRT
<213> ORGANISM: Artificial sequence
<220> FEATURE:
<223> OTHER INFORMATION: human mAb CDR:HC3; clone: p2.18

<400> SEQUENCE: 93

Thr Leu Asn Asn Phe Phe Asp Tyr Trp
1               5

<210> SEQ ID NO 94
<211> LENGTH: 9
<212> TYPE: PRT
<213> ORGANISM: Artificial sequence
<220> FEATURE:
<223> OTHER INFORMATION: human mAb CDR:HC3; clone: p2.19

<400> SEQUENCE: 94

Pro Leu Asn Asn Phe Phe Asp Tyr Trp
1               5

<210> SEQ ID NO 95
<211> LENGTH: 11
<212> TYPE: PRT
<213> ORGANISM: Artificial sequence
<220> FEATURE:
<223> OTHER INFORMATION: human mAb CDR:HC3; clone: p2.20

<400> SEQUENCE: 95

Glu Asn Asn Trp Asn Ser Phe Phe Asp Tyr Trp
1               5                   10

<210> SEQ ID NO 96
<211> LENGTH: 9
<212> TYPE: PRT
<213> ORGANISM: Artificial sequence
<220> FEATURE:
<223> OTHER INFORMATION: human mAb CDR:HC3; clone: p2.21

<400> SEQUENCE: 96

Thr Trp Asn Asn Phe Phe Asp Tyr Trp
1               5

<210> SEQ ID NO 97
<211> LENGTH: 10
<212> TYPE: PRT
<213> ORGANISM: Artificial sequence
<220> FEATURE:
<223> OTHER INFORMATION: human mAb CDR:HC3; clone: p1.22

<400> SEQUENCE: 97

Val Ser Trp Asp Val Phe Phe Asp Tyr Trp
1               5                   10

<210> SEQ ID NO 98

```
<211> LENGTH: 16
<212> TYPE: PRT
<213> ORGANISM: Artificial sequence
<220> FEATURE:
<223> OTHER INFORMATION: human mAb CDR:HC3; clone: p1.23

<400> SEQUENCE: 98

Ser Gly Pro Lys Ser Gly Lys Tyr Trp Asn Asn Phe Phe Asp Ser Trp
1               5                   10                  15

<210> SEQ ID NO 99
<211> LENGTH: 16
<212> TYPE: PRT
<213> ORGANISM: Artificial sequence
<220> FEATURE:
<223> OTHER INFORMATION: human mAb CDR:HC3; clone: p1.24

<400> SEQUENCE: 99

Ser Gly Pro Lys Ser Gly Lys Tyr Trp Asn Asn Phe Phe Asp Ser Trp
1               5                   10                  15

<210> SEQ ID NO 100
<211> LENGTH: 12
<212> TYPE: PRT
<213> ORGANISM: Artificial sequence
<220> FEATURE:
<223> OTHER INFORMATION: human mAb CDR:HC3; clone: p1.25

<400> SEQUENCE: 100

Asp Arg Gly Asn Ser Tyr Gly Phe Tyr Asp Tyr Trp
1               5                   10

<210> SEQ ID NO 101
<211> LENGTH: 16
<212> TYPE: PRT
<213> ORGANISM: Artificial sequence
<220> FEATURE:
<223> OTHER INFORMATION: human mAb CDR:HC3; clone: p1.1

<400> SEQUENCE: 101

Ser Gly Pro Lys Ser Gly Lys Tyr Trp Asn Asn Phe Phe Asp Ser Trp
1               5                   10                  15

<210> SEQ ID NO 102
<211> LENGTH: 16
<212> TYPE: PRT
<213> ORGANISM: Artificial sequence
<220> FEATURE:
<223> OTHER INFORMATION: human mAb CDR:HC3; clone: p1.26

<400> SEQUENCE: 102

Ser Gly Pro Lys Ser Gly Lys Tyr Trp Asn Asn Phe Phe Asp Ser Trp
1               5                   10                  15

<210> SEQ ID NO 103
<211> LENGTH: 11
<212> TYPE: PRT
<213> ORGANISM: Artificial sequence
<220> FEATURE:
<223> OTHER INFORMATION: human mAb CDR:HC3; clone: p1.27

<400> SEQUENCE: 103

Asp Pro Phe Gly His Gly Phe Phe Asp Tyr Trp
1               5                   10

<210> SEQ ID NO 104
<211> LENGTH: 16
```

```
<212> TYPE: PRT
<213> ORGANISM: Artificial sequence
<220> FEATURE:
<223> OTHER INFORMATION: human mAb CDR:HC3; clone: p1.28

<400> SEQUENCE: 104

Ser Gly Pro Lys Ser Gly Lys Tyr Trp Asn Asn Phe Phe Asp Ser Trp
1               5                   10                  15

<210> SEQ ID NO 105
<211> LENGTH: 16
<212> TYPE: PRT
<213> ORGANISM: Artificial sequence
<220> FEATURE:
<223> OTHER INFORMATION: human mAb CDR:HC3; clone: p1.29

<400> SEQUENCE: 105

Ser Gly Pro Lys Ser Gly Lys Tyr Trp Asn Asn Phe Phe Asp Ser Trp
1               5                   10                  15

<210> SEQ ID NO 106
<211> LENGTH: 11
<212> TYPE: PRT
<213> ORGANISM: Artificial sequence
<220> FEATURE:
<223> OTHER INFORMATION: human mAb CDR:HC3; clone: p1.30

<400> SEQUENCE: 106

Asp Pro Phe Gly His Gly Phe Phe Asp Tyr Trp
1               5                   10

<210> SEQ ID NO 107
<211> LENGTH: 11
<212> TYPE: PRT
<213> ORGANISM: Artificial sequence
<220> FEATURE:
<223> OTHER INFORMATION: human mAb CDR:HC3; clone: p1.6

<400> SEQUENCE: 107

Asp Pro Phe Gly His Gly Phe Phe Asp Tyr Trp
1               5                   10

<210> SEQ ID NO 108
<211> LENGTH: 10
<212> TYPE: PRT
<213> ORGANISM: Artificial sequence
<220> FEATURE:
<223> OTHER INFORMATION: human mAb CDR:HC3; clone: p1.2

<400> SEQUENCE: 108

Val Ser Trp Asp Val Phe Phe Asp Tyr Trp
1               5                   10

<210> SEQ ID NO 109
<211> LENGTH: 10
<212> TYPE: PRT
<213> ORGANISM: Artificial sequence
<220> FEATURE:
<223> OTHER INFORMATION: human mAb CDR:HC3; clone: p1.31

<400> SEQUENCE: 109

Val Ser Trp Asp Val Phe Phe Asp Tyr Trp
1               5                   10

<210> SEQ ID NO 110
<211> LENGTH: 11
<212> TYPE: PRT
```

<213> ORGANISM: Artificial sequence
<220> FEATURE:
<223> OTHER INFORMATION: human mAb CDR:HC3; clone: p1.5

<400> SEQUENCE: 110

Asp Pro Phe Gly His Gly Phe Phe Asp Tyr Trp
1               5                   10

<210> SEQ ID NO 111
<211> LENGTH: 11
<212> TYPE: PRT
<213> ORGANISM: Artificial sequence
<220> FEATURE:
<223> OTHER INFORMATION: human mAb CDR:HC3; clone: p1.32

<400> SEQUENCE: 111

Asp Pro Phe Gly His Gly Phe Phe Asp Tyr Trp
1               5                   10

<210> SEQ ID NO 112
<211> LENGTH: 12
<212> TYPE: PRT
<213> ORGANISM: Artificial sequence
<220> FEATURE:
<223> OTHER INFORMATION: human mAb CDR:HC3; clone: p1.33

<400> SEQUENCE: 112

Asp Arg Gly Asn Ser Tyr Gly Phe Tyr Asp Tyr Trp
1               5                   10

<210> SEQ ID NO 113
<211> LENGTH: 10
<212> TYPE: PRT
<213> ORGANISM: Artificial sequence
<220> FEATURE:
<223> OTHER INFORMATION: human mAb CDR:HC3; clone: p1.39

<400> SEQUENCE: 113

Val Ser Trp Asp Val Phe Phe Asp Tyr Trp
1               5                   10

<210> SEQ ID NO 114
<211> LENGTH: 10
<212> TYPE: PRT
<213> ORGANISM: Artificial sequence
<220> FEATURE:
<223> OTHER INFORMATION: human mAb CDR:HC3; clone: p1.22

<400> SEQUENCE: 114

Val Ser Trp Asp Val Phe Phe Asp Tyr Trp
1               5                   10

<210> SEQ ID NO 115
<211> LENGTH: 13
<212> TYPE: PRT
<213> ORGANISM: Artificial sequence
<220> FEATURE:
<223> OTHER INFORMATION: human mAb CDR:HC3; clone: p3.1.34

<400> SEQUENCE: 115

Asp Leu Gly Thr Trp Asn Ser Tyr Gly Phe Asp Tyr Trp
1               5                   10

<210> SEQ ID NO 116
<211> LENGTH: 11
<212> TYPE: PRT
<213> ORGANISM: Artificial sequence

```
<220> FEATURE:
<223> OTHER INFORMATION: human mAb CDR:HC3; clone: p3.1.35

<400> SEQUENCE: 116

Arg Asp His Arg Ser Thr Phe Phe Asp Tyr Trp
1               5                   10

<210> SEQ ID NO 117
<211> LENGTH: 9
<212> TYPE: PRT
<213> ORGANISM: Artificial sequence
<220> FEATURE:
<223> OTHER INFORMATION: human mAb CDR:HC3; clone: p3.1.36

<400> SEQUENCE: 117

Thr Leu Asn Asn Phe Phe Asp Tyr Trp
1               5

<210> SEQ ID NO 118
<211> LENGTH: 13
<212> TYPE: PRT
<213> ORGANISM: Artificial sequence
<220> FEATURE:
<223> OTHER INFORMATION: human mAb CDR:HC3; clone: p3.1.37

<400> SEQUENCE: 118

Asp Leu Gly Thr Trp Asn Ser Tyr Gly Phe Asp Tyr Trp
1               5                   10

<210> SEQ ID NO 119
<211> LENGTH: 11
<212> TYPE: PRT
<213> ORGANISM: Artificial sequence
<220> FEATURE:
<223> OTHER INFORMATION: human mAb CDR:HC3; clone: p3.2.38

<400> SEQUENCE: 119

Arg Asp His Arg Ser Thr Phe Phe Asp Tyr Trp
1               5                   10

<210> SEQ ID NO 120
<211> LENGTH: 9
<212> TYPE: PRT
<213> ORGANISM: Artificial sequence
<220> FEATURE:
<223> OTHER INFORMATION: human mAb CDR:HC3; clone: p3.2.40

<400> SEQUENCE: 120

Thr Leu Asn Asn Phe Phe Asp Tyr Trp
1               5

<210> SEQ ID NO 121
<211> LENGTH: 9
<212> TYPE: PRT
<213> ORGANISM: Artificial sequence
<220> FEATURE:
<223> OTHER INFORMATION: human mAb CDR:LC1; clone: p2.3

<400> SEQUENCE: 121

Ser Gln Asn Val Arg Ser Asp Leu Ala
1               5

<210> SEQ ID NO 122
<211> LENGTH: 9
<212> TYPE: PRT
<213> ORGANISM: Artificial sequence
<220> FEATURE:
```

<223> OTHER INFORMATION: human mAb CDR:LC1; clone: p2.8

<400> SEQUENCE: 122

Ser Gln Ser Val Asn Ser Lys Leu Ala
1               5

<210> SEQ ID NO 123
<211> LENGTH: 9
<212> TYPE: PRT
<213> ORGANISM: Artificial sequence
<220> FEATURE:
<223> OTHER INFORMATION: human mAb CDR:LC1; clone: p2.9

<400> SEQUENCE: 123

Ser Gln Thr Val Lys Thr Tyr Leu Ala
1               5

<210> SEQ ID NO 124
<211> LENGTH: 9
<212> TYPE: PRT
<213> ORGANISM: Artificial sequence
<220> FEATURE:
<223> OTHER INFORMATION: human mAb CDR:LC1; clone: p2.10

<400> SEQUENCE: 124

Ser Gln Gly Ile Val Gly Asn Leu Ala
1               5

<210> SEQ ID NO 125
<211> LENGTH: 9
<212> TYPE: PRT
<213> ORGANISM: Artificial sequence
<220> FEATURE:
<223> OTHER INFORMATION: human mAb CDR:LC1; clone: p2.4

<400> SEQUENCE: 125

Ser Gln Asn Val Arg Ser Asp Leu Ala
1               5

<210> SEQ ID NO 126
<211> LENGTH: 9
<212> TYPE: PRT
<213> ORGANISM: Artificial sequence
<220> FEATURE:
<223> OTHER INFORMATION: human mAb CDR:LC1; clone: p2.11

<400> SEQUENCE: 126

Ser Gln Thr Val Lys Thr Tyr Leu Ala
1               5

<210> SEQ ID NO 127
<211> LENGTH: 9
<212> TYPE: PRT
<213> ORGANISM: Artificial sequence
<220> FEATURE:
<223> OTHER INFORMATION: human mAb CDR:LC1; clone: p2.12

<400> SEQUENCE: 127

Ser Gln Ser Val Asn Ser Asn Leu Ala
1               5

<210> SEQ ID NO 128
<211> LENGTH: 9
<212> TYPE: PRT
<213> ORGANISM: Artificial sequence
<220> FEATURE:
<223> OTHER INFORMATION: human mAb CDR:LC1; clone: p2.13

```
<400> SEQUENCE: 128

Ser Gln Thr Val Lys Thr Tyr Leu Ala
1               5

<210> SEQ ID NO 129
<211> LENGTH: 9
<212> TYPE: PRT
<213> ORGANISM: Artificial sequence
<220> FEATURE:
<223> OTHER INFORMATION: human mAb CDR:LC1; clone: p2.14

<400> SEQUENCE: 129

Ser Gln Ser Val Ser Ser Tyr Leu Ala
1               5

<210> SEQ ID NO 130
<211> LENGTH: 9
<212> TYPE: PRT
<213> ORGANISM: Artificial sequence
<220> FEATURE:
<223> OTHER INFORMATION: human mAb CDR:LC1; clone: p2.15

<400> SEQUENCE: 130

Ser Gln Thr Val Gly Ser Lys Leu Ala
1               5

<210> SEQ ID NO 131
<211> LENGTH: 9
<212> TYPE: PRT
<213> ORGANISM: Artificial sequence
<220> FEATURE:
<223> OTHER INFORMATION: human mAb CDR:LC1; clone: p2.16

<400> SEQUENCE: 131

Ser Gln Ser Val His Ser Tyr Leu Ala
1               5

<210> SEQ ID NO 132
<211> LENGTH: 9
<212> TYPE: PRT
<213> ORGANISM: Artificial sequence
<220> FEATURE:
<223> OTHER INFORMATION: human mAb CDR:LC1; clone: p2.17

<400> SEQUENCE: 132

Ser Gln Ser Val Lys Thr Tyr Leu Ala
1               5

<210> SEQ ID NO 133
<211> LENGTH: 10
<212> TYPE: PRT
<213> ORGANISM: Artificial sequence
<220> FEATURE:
<223> OTHER INFORMATION: human mAb CDR:LC1; clone: p2.18

<400> SEQUENCE: 133

Ser His Ser Val Ser Ser Thr Tyr Leu Ala
1               5                   10

<210> SEQ ID NO 134
<211> LENGTH: 9
<212> TYPE: PRT
<213> ORGANISM: Artificial sequence
<220> FEATURE:
<223> OTHER INFORMATION: human mAb CDR:LC1; clone: p2.19
```

```
<400> SEQUENCE: 134

Ser Gln Asn Val Arg Ser Asp Leu Ala
1               5

<210> SEQ ID NO 135
<211> LENGTH: 9
<212> TYPE: PRT
<213> ORGANISM: Artificial sequence
<220> FEATURE:
<223> OTHER INFORMATION: human mAb CDR:LC1; clone: p2.20

<400> SEQUENCE: 135

Ser Gln Ser Val Gly Ser Asn Leu Ala
1               5

<210> SEQ ID NO 136
<211> LENGTH: 9
<212> TYPE: PRT
<213> ORGANISM: Artificial sequence
<220> FEATURE:
<223> OTHER INFORMATION: human mAb CDR:LC1; clone: p2.21

<400> SEQUENCE: 136

Ser Gln Thr Val Lys Thr Tyr Leu Ala
1               5

<210> SEQ ID NO 137
<211> LENGTH: 9
<212> TYPE: PRT
<213> ORGANISM: Artificial sequence
<220> FEATURE:
<223> OTHER INFORMATION: human mAb CDR:LC1; clone: p1.22

<400> SEQUENCE: 137

Ser Gln Pro Ile Asp Val Tyr Leu Ala
1               5

<210> SEQ ID NO 138
<211> LENGTH: 9
<212> TYPE: PRT
<213> ORGANISM: Artificial sequence
<220> FEATURE:
<223> OTHER INFORMATION: human mAb CDR:LC1; clone: p1.23

<400> SEQUENCE: 138

Ser Gln Thr Val Gly Ser Lys Leu Ala
1               5

<210> SEQ ID NO 139
<211> LENGTH: 10
<212> TYPE: PRT
<213> ORGANISM: Artificial sequence
<220> FEATURE:
<223> OTHER INFORMATION: human mAb CDR:LC1; clone: p1.24

<400> SEQUENCE: 139

Ser Gln Ser Val Gly Ser Tyr Tyr Leu Ala
1               5                   10

<210> SEQ ID NO 140
<211> LENGTH: 10
<212> TYPE: PRT
<213> ORGANISM: Artificial sequence
<220> FEATURE:
<223> OTHER INFORMATION: human mAb CDR:LC1; clone: p1.25

<400> SEQUENCE: 140
```

Ser Gln Ser Val Ser Ala Ser Gln Leu Ala
1               5                   10

<210> SEQ ID NO 141
<211> LENGTH: 9
<212> TYPE: PRT
<213> ORGANISM: Artificial sequence
<220> FEATURE:
<223> OTHER INFORMATION: human mAb CDR:LC1; clone: p1.1

<400> SEQUENCE: 141

Ser Gln Ser Val Lys Thr Asp Leu Ala
1               5

<210> SEQ ID NO 142
<211> LENGTH: 9
<212> TYPE: PRT
<213> ORGANISM: Artificial sequence
<220> FEATURE:
<223> OTHER INFORMATION: human mAb CDR:LC1; clone: p1.26

<400> SEQUENCE: 142

Ser Gln Ser Val Lys Thr Asp Leu Ala
1               5

<210> SEQ ID NO 143
<211> LENGTH: 9
<212> TYPE: PRT
<213> ORGANISM: Artificial sequence
<220> FEATURE:
<223> OTHER INFORMATION: human mAb CDR:LC1; clone: p1.27

<400> SEQUENCE: 143

Ser Gln Ser Val Asn Arg Asn Leu Ala
1               5

<210> SEQ ID NO 144
<211> LENGTH: 9
<212> TYPE: PRT
<213> ORGANISM: Artificial sequence
<220> FEATURE:
<223> OTHER INFORMATION: human mAb CDR:LC1; clone: p1.28

<400> SEQUENCE: 144

Ser Gln Pro Ile Asn Thr Tyr Leu Ala
1               5

<210> SEQ ID NO 145
<211> LENGTH: 9
<212> TYPE: PRT
<213> ORGANISM: Artificial sequence
<220> FEATURE:
<223> OTHER INFORMATION: human mAb CDR:LC1; clone: p1.29

<400> SEQUENCE: 145

Ser Gln Thr Val Gly Ser Lys Leu Ala
1               5

<210> SEQ ID NO 146
<211> LENGTH: 9
<212> TYPE: PRT
<213> ORGANISM: Artificial sequence
<220> FEATURE:
<223> OTHER INFORMATION: human mAb CDR:LC1; clone: p1.30

<400> SEQUENCE: 146

Ser Gln Ser Val Asn Arg Asn Leu Ala
1               5

<210> SEQ ID NO 147
<211> LENGTH: 9
<212> TYPE: PRT
<213> ORGANISM: Artificial sequence
<220> FEATURE:
<223> OTHER INFORMATION: human mAb CDR:LC1; clone: p1.6

<400> SEQUENCE: 147

Ser Gln Ser Val Asn Arg Asn Leu Ala
1               5

<210> SEQ ID NO 148
<211> LENGTH: 9
<212> TYPE: PRT
<213> ORGANISM: Artificial sequence
<220> FEATURE:
<223> OTHER INFORMATION: human mAb CDR:LC1; clone: p1.2

<400> SEQUENCE: 148

Ser Gln Pro Ile Asp Val Tyr Leu Ala
1               5

<210> SEQ ID NO 149
<211> LENGTH: 9
<212> TYPE: PRT
<213> ORGANISM: Artificial sequence
<220> FEATURE:
<223> OTHER INFORMATION: human mAb CDR:LC1; clone: p1.31

<400> SEQUENCE: 149

Ser Gln Pro Ile Asp Val Tyr Leu Ala
1               5

<210> SEQ ID NO 150
<211> LENGTH: 9
<212> TYPE: PRT
<213> ORGANISM: Artificial sequence
<220> FEATURE:
<223> OTHER INFORMATION: human mAb CDR:LC1; clone: p1.5

<400> SEQUENCE: 150

Ser Gln Thr Val Gly Ser Lys Leu Ala
1               5

<210> SEQ ID NO 151
<211> LENGTH: 9
<212> TYPE: PRT
<213> ORGANISM: Artificial sequence
<220> FEATURE:
<223> OTHER INFORMATION: human mAb CDR:LC1; clone: p1.32

<400> SEQUENCE: 151

Ser Gln Ser Val Asn His Asn Leu Ala
1               5

<210> SEQ ID NO 152
<211> LENGTH: 9
<212> TYPE: PRT
<213> ORGANISM: Artificial sequence
<220> FEATURE:
<223> OTHER INFORMATION: human mAb CDR:LC1; clone: p1.33

<400> SEQUENCE: 152

Asn Arg Ser Ile Leu Thr Ser Leu Ala

```
1               5
```

<210> SEQ ID NO 153
<211> LENGTH: 9
<212> TYPE: PRT
<213> ORGANISM: Artificial sequence
<220> FEATURE:
<223> OTHER INFORMATION: human mAb CDR:LC1; clone: p1.39

<400> SEQUENCE: 153

```
Ser Gln Pro Ile Asp Val Tyr Leu Ala
1               5
```

<210> SEQ ID NO 154
<211> LENGTH: 9
<212> TYPE: PRT
<213> ORGANISM: Artificial sequence
<220> FEATURE:
<223> OTHER INFORMATION: human mAb CDR:LC1; clone: p1.22

<400> SEQUENCE: 154

```
Ser Gln Pro Ile Asp Val Tyr Leu Ala
1               5
```

<210> SEQ ID NO 155
<211> LENGTH: 9
<212> TYPE: PRT
<213> ORGANISM: Artificial sequence
<220> FEATURE:
<223> OTHER INFORMATION: human mAb CDR:LC1; clone: p3.1.34

<400> SEQUENCE: 155

```
Ser Gln Thr Val Asn Thr Lys Leu Ala
1               5
```

<210> SEQ ID NO 156
<211> LENGTH: 9
<212> TYPE: PRT
<213> ORGANISM: Artificial sequence
<220> FEATURE:
<223> OTHER INFORMATION: human mAb CDR:LC1; clone: p3.1.35

<400> SEQUENCE: 156

```
Ser Gln Ser Val Ser Ser Asn Leu Ala
1               5
```

<210> SEQ ID NO 157
<211> LENGTH: 10
<212> TYPE: PRT
<213> ORGANISM: Artificial sequence
<220> FEATURE:
<223> OTHER INFORMATION: human mAb CDR:LC1; clone: p3.1.36

<400> SEQUENCE: 157

```
Ser Gln Ser Val Ser Asp Thr Tyr Leu Ala
1               5                   10
```

<210> SEQ ID NO 158
<211> LENGTH: 9
<212> TYPE: PRT
<213> ORGANISM: Artificial sequence
<220> FEATURE:
<223> OTHER INFORMATION: human mAb CDR:LC1; clone: p3.1.37

<400> SEQUENCE: 158

```
Ser Gln Thr Val Thr Thr Lys Leu Ala
1               5
```

<210> SEQ ID NO 159
<211> LENGTH: 9
<212> TYPE: PRT
<213> ORGANISM: Artificial sequence
<220> FEATURE:
<223> OTHER INFORMATION: human mAb CDR:LC1; clone: p3.2.38

<400> SEQUENCE: 159

Ser Gln Ser Val Ser Ser Asn Leu Ala
1               5

<210> SEQ ID NO 160
<211> LENGTH: 10
<212> TYPE: PRT
<213> ORGANISM: Artificial sequence
<220> FEATURE:
<223> OTHER INFORMATION: human mAb CDR:LC1; clone: p3.2.40

<400> SEQUENCE: 160

Ser Gln Ser Val Ser Asp Thr Tyr Leu Ala
1               5                   10

<210> SEQ ID NO 161
<211> LENGTH: 7
<212> TYPE: PRT
<213> ORGANISM: Artificial sequence
<220> FEATURE:
<223> OTHER INFORMATION: human mAb CDR:LC2; clone: p2.3

<400> SEQUENCE: 161

Asp Ala Ser Asn Arg Ala Thr
1               5

<210> SEQ ID NO 162
<211> LENGTH: 7
<212> TYPE: PRT
<213> ORGANISM: Artificial sequence
<220> FEATURE:
<223> OTHER INFORMATION: human mAb CDR:LC2; clone: p2.8

<400> SEQUENCE: 162

Asp Ala Ser Ser Arg Ala Thr
1               5

<210> SEQ ID NO 163
<211> LENGTH: 7
<212> TYPE: PRT
<213> ORGANISM: Artificial sequence
<220> FEATURE:
<223> OTHER INFORMATION: human mAb CDR:LC2; clone: p2.9

<400> SEQUENCE: 163

Ala Ala Ser Ser Arg Ala Ala
1               5

<210> SEQ ID NO 164
<211> LENGTH: 7
<212> TYPE: PRT
<213> ORGANISM: Artificial sequence
<220> FEATURE:
<223> OTHER INFORMATION: human mAb CDR:LC2; clone: p2.10

<400> SEQUENCE: 164

Asp Ala Ser Ser Arg Ala Thr
1               5

```
<210> SEQ ID NO 165
<211> LENGTH: 7
<212> TYPE: PRT
<213> ORGANISM: Artificial sequence
<220> FEATURE:
<223> OTHER INFORMATION: human mAb CDR:LC2; clone: p2.4

<400> SEQUENCE: 165

Gly Ala Ser Thr Arg Ala Thr
1               5

<210> SEQ ID NO 166
<211> LENGTH: 7
<212> TYPE: PRT
<213> ORGANISM: Artificial sequence
<220> FEATURE:
<223> OTHER INFORMATION: human mAb CDR:LC2; clone: p2.11

<400> SEQUENCE: 166

Asp Ala Ser Thr Arg Ala Thr
1               5

<210> SEQ ID NO 167
<211> LENGTH: 7
<212> TYPE: PRT
<213> ORGANISM: Artificial sequence
<220> FEATURE:
<223> OTHER INFORMATION: human mAb CDR:LC2; clone: p2.12

<400> SEQUENCE: 167

Asp Ala Ser Ser Arg Ala Thr
1               5

<210> SEQ ID NO 168
<211> LENGTH: 7
<212> TYPE: PRT
<213> ORGANISM: Artificial sequence
<220> FEATURE:
<223> OTHER INFORMATION: human mAb CDR:LC2; clone: p2.13

<400> SEQUENCE: 168

Asp Ala Ser Thr Arg Ala Thr
1               5

<210> SEQ ID NO 169
<211> LENGTH: 7
<212> TYPE: PRT
<213> ORGANISM: Artificial sequence
<220> FEATURE:
<223> OTHER INFORMATION: human mAb CDR:LC2; clone: p2.14

<400> SEQUENCE: 169

Gly Ala Ser Thr Arg Ala Thr
1               5

<210> SEQ ID NO 170
<211> LENGTH: 7
<212> TYPE: PRT
<213> ORGANISM: Artificial sequence
<220> FEATURE:
<223> OTHER INFORMATION: human mAb CDR:LC2; clone: p2.15

<400> SEQUENCE: 170

Asp Ala Ser Thr Arg Ala Thr
1               5
```

```
<210> SEQ ID NO 171
<211> LENGTH: 7
<212> TYPE: PRT
<213> ORGANISM: Artificial sequence
<220> FEATURE:
<223> OTHER INFORMATION: human mAb CDR:LC2; clone: p2.16

<400> SEQUENCE: 171

Asp Ala Ser Ser Arg Ala Thr
1               5

<210> SEQ ID NO 172
<211> LENGTH: 7
<212> TYPE: PRT
<213> ORGANISM: Artificial sequence
<220> FEATURE:
<223> OTHER INFORMATION: human mAb CDR:LC2; clone: p2.17

<400> SEQUENCE: 172

Asp Ala Ser Asp Arg Ala Thr
1               5

<210> SEQ ID NO 173
<211> LENGTH: 7
<212> TYPE: PRT
<213> ORGANISM: Artificial sequence
<220> FEATURE:
<223> OTHER INFORMATION: human mAb CDR:LC2; clone: p2.18

<400> SEQUENCE: 173

Asp Ala Ser Thr Arg Ala Thr
1               5

<210> SEQ ID NO 174
<211> LENGTH: 7
<212> TYPE: PRT
<213> ORGANISM: Artificial sequence
<220> FEATURE:
<223> OTHER INFORMATION: human mAb CDR:LC2; clone: p2.19

<400> SEQUENCE: 174

Gly Ala Ser Ser Arg Ala Thr
1               5

<210> SEQ ID NO 175
<211> LENGTH: 7
<212> TYPE: PRT
<213> ORGANISM: Artificial sequence
<220> FEATURE:
<223> OTHER INFORMATION: human mAb CDR:LC2; clone: p2.20

<400> SEQUENCE: 175

Ala Ala Ser Ser Arg Ala Thr
1               5

<210> SEQ ID NO 176
<211> LENGTH: 7
<212> TYPE: PRT
<213> ORGANISM: Artificial sequence
<220> FEATURE:
<223> OTHER INFORMATION: human mAb CDR:LC2; clone: p2.21

<400> SEQUENCE: 176

Asp Ala Ser Thr Lys Ala Thr
1               5

<210> SEQ ID NO 177
```

```
<211> LENGTH: 7
<212> TYPE: PRT
<213> ORGANISM: Artificial sequence
<220> FEATURE:
<223> OTHER INFORMATION: human mAb CDR:LC2; clone: p1.22

<400> SEQUENCE: 177

Gly Ala Ser Arg Arg Ala Thr
1               5

<210> SEQ ID NO 178
<211> LENGTH: 7
<212> TYPE: PRT
<213> ORGANISM: Artificial sequence
<220> FEATURE:
<223> OTHER INFORMATION: human mAb CDR:LC2; clone: p1.23

<400> SEQUENCE: 178

Ala Ala Ser Ser Arg Asp Thr
1               5

<210> SEQ ID NO 179
<211> LENGTH: 7
<212> TYPE: PRT
<213> ORGANISM: Artificial sequence
<220> FEATURE:
<223> OTHER INFORMATION: human mAb CDR:LC2; clone: p1.24

<400> SEQUENCE: 179

Gly Ala Ser Arg Arg Ala Thr
1               5

<210> SEQ ID NO 180
<211> LENGTH: 7
<212> TYPE: PRT
<213> ORGANISM: Artificial sequence
<220> FEATURE:
<223> OTHER INFORMATION: human mAb CDR:LC2; clone: p1.25

<400> SEQUENCE: 180

Asp Ala Thr Thr Arg Ala Thr
1               5

<210> SEQ ID NO 181
<211> LENGTH: 7
<212> TYPE: PRT
<213> ORGANISM: Artificial sequence
<220> FEATURE:
<223> OTHER INFORMATION: human mAb CDR:LC2; clone: p1.1

<400> SEQUENCE: 181

Gly Ala Thr Thr Arg Ala Thr
1               5

<210> SEQ ID NO 182
<211> LENGTH: 7
<212> TYPE: PRT
<213> ORGANISM: Artificial sequence
<220> FEATURE:
<223> OTHER INFORMATION: human mAb CDR:LC2; clone: p1.26

<400> SEQUENCE: 182

Gly Ala Thr Thr Arg Ala Thr
1               5

<210> SEQ ID NO 183
<211> LENGTH: 7
```

```
<212> TYPE: PRT
<213> ORGANISM: Artificial sequence
<220> FEATURE:
<223> OTHER INFORMATION: human mAb CDR:LC2; clone: p1.27

<400> SEQUENCE: 183

Asp Ala Arg Thr Arg Ala Thr
1               5

<210> SEQ ID NO 184
<211> LENGTH: 7
<212> TYPE: PRT
<213> ORGANISM: Artificial sequence
<220> FEATURE:
<223> OTHER INFORMATION: human mAb CDR:LC2; clone: p1.28

<400> SEQUENCE: 184

Asp Ala Ser Thr Arg Ala Thr
1               5

<210> SEQ ID NO 185
<211> LENGTH: 7
<212> TYPE: PRT
<213> ORGANISM: Artificial sequence
<220> FEATURE:
<223> OTHER INFORMATION: human mAb CDR:LC2; clone: p1.29

<400> SEQUENCE: 185

Ser Ala Ser Ser Arg Ala Thr
1               5

<210> SEQ ID NO 186
<211> LENGTH: 7
<212> TYPE: PRT
<213> ORGANISM: Artificial sequence
<220> FEATURE:
<223> OTHER INFORMATION: human mAb CDR:LC2; clone: p1.30

<400> SEQUENCE: 186

Asp Ala Arg Thr Arg Ala Thr
1               5

<210> SEQ ID NO 187
<211> LENGTH: 7
<212> TYPE: PRT
<213> ORGANISM: Artificial sequence
<220> FEATURE:
<223> OTHER INFORMATION: human mAb CDR:LC2; clone: p1.6

<400> SEQUENCE: 187

Asp Ala Arg Thr Arg Ala Thr
1               5

<210> SEQ ID NO 188
<211> LENGTH: 7
<212> TYPE: PRT
<213> ORGANISM: Artificial sequence
<220> FEATURE:
<223> OTHER INFORMATION: human mAb CDR:LC2; clone: p1.2

<400> SEQUENCE: 188

Gly Ala Asn Arg Arg Ala Ile
1               5

<210> SEQ ID NO 189
<211> LENGTH: 7
<212> TYPE: PRT
```

```
<213> ORGANISM: Artificial sequence
<220> FEATURE:
<223> OTHER INFORMATION: human mAb CDR:LC2; clone: p1.31

<400> SEQUENCE: 189

Gly Ala Asn Arg Arg Ala Ile
1               5

<210> SEQ ID NO 190
<211> LENGTH: 7
<212> TYPE: PRT
<213> ORGANISM: Artificial sequence
<220> FEATURE:
<223> OTHER INFORMATION: human mAb CDR:LC2; clone: p1.5

<400> SEQUENCE: 190

Asp Ala Ser Thr Arg Ala Thr
1               5

<210> SEQ ID NO 191
<211> LENGTH: 7
<212> TYPE: PRT
<213> ORGANISM: Artificial sequence
<220> FEATURE:
<223> OTHER INFORMATION: human mAb CDR:LC2; clone: p1.32

<400> SEQUENCE: 191

Asp Ala Arg Thr Arg Ala Thr
1               5

<210> SEQ ID NO 192
<211> LENGTH: 7
<212> TYPE: PRT
<213> ORGANISM: Artificial sequence
<220> FEATURE:
<223> OTHER INFORMATION: human mAb CDR:LC2; clone: p1.33

<400> SEQUENCE: 192

Asp Ala Ser Thr Arg Ala Thr
1               5

<210> SEQ ID NO 193
<211> LENGTH: 7
<212> TYPE: PRT
<213> ORGANISM: Artificial sequence
<220> FEATURE:
<223> OTHER INFORMATION: human mAb CDR:LC2; clone: p1.39

<400> SEQUENCE: 193

Gly Ala Asn Arg Arg Ala Ile
1               5

<210> SEQ ID NO 194
<211> LENGTH: 7
<212> TYPE: PRT
<213> ORGANISM: Artificial sequence
<220> FEATURE:
<223> OTHER INFORMATION: human mAb CDR:LC2; clone: p1.22

<400> SEQUENCE: 194

Gly Ala Ser Arg Arg Ala Thr
1               5

<210> SEQ ID NO 195
<211> LENGTH: 7
<212> TYPE: PRT
<213> ORGANISM: Artificial sequence
```

```
<220> FEATURE:
<223> OTHER INFORMATION: human mAb CDR:LC2; clone: p3.1.34

<400> SEQUENCE: 195

Asp Ala Ser Thr Arg Ala Thr
1               5

<210> SEQ ID NO 196
<211> LENGTH: 7
<212> TYPE: PRT
<213> ORGANISM: Artificial sequence
<220> FEATURE:
<223> OTHER INFORMATION: human mAb CDR:LC2; clone: p3.1.35

<400> SEQUENCE: 196

Gly Ala Asn Thr Arg Ala Thr
1               5

<210> SEQ ID NO 197
<211> LENGTH: 7
<212> TYPE: PRT
<213> ORGANISM: Artificial sequence
<220> FEATURE:
<223> OTHER INFORMATION: human mAb CDR:LC2; clone: p3.1.36

<400> SEQUENCE: 197

Asp Thr Ser Thr Arg Ala Thr
1               5

<210> SEQ ID NO 198
<211> LENGTH: 7
<212> TYPE: PRT
<213> ORGANISM: Artificial sequence
<220> FEATURE:
<223> OTHER INFORMATION: human mAb CDR:LC2; clone: p3.1.37

<400> SEQUENCE: 198

Asp Ala Ser Thr Arg Ala Thr
1               5

<210> SEQ ID NO 199
<211> LENGTH: 7
<212> TYPE: PRT
<213> ORGANISM: Artificial sequence
<220> FEATURE:
<223> OTHER INFORMATION: human mAb CDR:LC2; clone: p3.2.38

<400> SEQUENCE: 199

Gly Ala Asn Thr Arg Ala Thr
1               5

<210> SEQ ID NO 200
<211> LENGTH: 7
<212> TYPE: PRT
<213> ORGANISM: Artificial sequence
<220> FEATURE:
<223> OTHER INFORMATION: human mAb CDR:LC2; clone: p3.2.40

<400> SEQUENCE: 200

Asp Thr Ser Thr Arg Ala Thr
1               5

<210> SEQ ID NO 201
<211> LENGTH: 8
<212> TYPE: PRT
<213> ORGANISM: Artificial sequence
<220> FEATURE:
```

```
<223> OTHER INFORMATION: human mAb CDR:LC3; clone: p2.3

<400> SEQUENCE: 201

Gln Gln Tyr Ser Asn Trp Pro Pro
1               5

<210> SEQ ID NO 202
<211> LENGTH: 8
<212> TYPE: PRT
<213> ORGANISM: Artificial sequence
<220> FEATURE:
<223> OTHER INFORMATION: human mAb CDR:LC3; clone: p2.8

<400> SEQUENCE: 202

Gln Gln Tyr Asn Thr Trp Pro Pro
1               5

<210> SEQ ID NO 203
<211> LENGTH: 8
<212> TYPE: PRT
<213> ORGANISM: Artificial sequence
<220> FEATURE:
<223> OTHER INFORMATION: human mAb CDR:LC3; clone: p2.9

<400> SEQUENCE: 203

Gln Gln Tyr Tyr Asp Trp Pro Pro
1               5

<210> SEQ ID NO 204
<211> LENGTH: 8
<212> TYPE: PRT
<213> ORGANISM: Artificial sequence
<220> FEATURE:
<223> OTHER INFORMATION: human mAb CDR:LC3; clone: p2.10

<400> SEQUENCE: 204

Gln Gln Tyr Tyr Asp Trp Pro Pro
1               5

<210> SEQ ID NO 205
<211> LENGTH: 8
<212> TYPE: PRT
<213> ORGANISM: Artificial sequence
<220> FEATURE:
<223> OTHER INFORMATION: human mAb CDR:LC3; clone: p2.4

<400> SEQUENCE: 205

Gln Gln Tyr Tyr Asp Trp Pro Pro
1               5

<210> SEQ ID NO 206
<211> LENGTH: 8
<212> TYPE: PRT
<213> ORGANISM: Artificial sequence
<220> FEATURE:
<223> OTHER INFORMATION: human mAb CDR:LC3; clone: p2.11

<400> SEQUENCE: 206

Gln Gln Ser Tyr Asp Trp Pro Pro
1               5

<210> SEQ ID NO 207
<211> LENGTH: 8
<212> TYPE: PRT
<213> ORGANISM: Artificial sequence
<220> FEATURE:
<223> OTHER INFORMATION: human mAb CDR:LC3; clone: p2.12
```

```
<400> SEQUENCE: 207

Gln Gln Tyr Asn Asn Trp Pro Pro
1               5

<210> SEQ ID NO 208
<211> LENGTH: 8
<212> TYPE: PRT
<213> ORGANISM: Artificial sequence
<220> FEATURE:
<223> OTHER INFORMATION: human mAb CDR:LC3; clone: p2.13

<400> SEQUENCE: 208

Gln Gln Ser Tyr Asp Trp Pro Pro
1               5

<210> SEQ ID NO 209
<211> LENGTH: 8
<212> TYPE: PRT
<213> ORGANISM: Artificial sequence
<220> FEATURE:
<223> OTHER INFORMATION: human mAb CDR:LC3; clone: p2.14

<400> SEQUENCE: 209

Gln Gln Tyr Asn Asn Trp Pro Pro
1               5

<210> SEQ ID NO 210
<211> LENGTH: 8
<212> TYPE: PRT
<213> ORGANISM: Artificial sequence
<220> FEATURE:
<223> OTHER INFORMATION: human mAb CDR:LC3; clone: p2.15

<400> SEQUENCE: 210

Gln Gln Tyr Tyr Asp Trp Pro Pro
1               5

<210> SEQ ID NO 211
<211> LENGTH: 8
<212> TYPE: PRT
<213> ORGANISM: Artificial sequence
<220> FEATURE:
<223> OTHER INFORMATION: human mAb CDR:LC3; clone: p2.16

<400> SEQUENCE: 211

Gln Gln Tyr Ser Asn Trp Pro Pro
1               5

<210> SEQ ID NO 212
<211> LENGTH: 8
<212> TYPE: PRT
<213> ORGANISM: Artificial sequence
<220> FEATURE:
<223> OTHER INFORMATION: human mAb CDR:LC3; clone: p2.17

<400> SEQUENCE: 212

Gln Gln Tyr Tyr Asp Trp Pro Pro
1               5

<210> SEQ ID NO 213
<211> LENGTH: 8
<212> TYPE: PRT
<213> ORGANISM: Artificial sequence
<220> FEATURE:
<223> OTHER INFORMATION: human mAb CDR:LC3; clone: p2.18
```

```
<400> SEQUENCE: 213

Gln Gln Tyr Tyr Asp Trp Pro Pro
1               5

<210> SEQ ID NO 214
<211> LENGTH: 8
<212> TYPE: PRT
<213> ORGANISM: Artificial sequence
<220> FEATURE:
<223> OTHER INFORMATION: human mAb CDR:LC3; clone: p2.19

<400> SEQUENCE: 214

Gln Gln Tyr Asn Asn Trp Pro Pro
1               5

<210> SEQ ID NO 215
<211> LENGTH: 8
<212> TYPE: PRT
<213> ORGANISM: Artificial sequence
<220> FEATURE:
<223> OTHER INFORMATION: human mAb CDR:LC3; clone: p2.20

<400> SEQUENCE: 215

Gln Gln Tyr Asn Asn Trp Pro Pro
1               5

<210> SEQ ID NO 216
<211> LENGTH: 8
<212> TYPE: PRT
<213> ORGANISM: Artificial sequence
<220> FEATURE:
<223> OTHER INFORMATION: human mAb CDR:LC3; clone: p2.21

<400> SEQUENCE: 216

Gln Gln Ser Tyr Asp Trp Pro Pro
1               5

<210> SEQ ID NO 217
<211> LENGTH: 8
<212> TYPE: PRT
<213> ORGANISM: Artificial sequence
<220> FEATURE:
<223> OTHER INFORMATION: human mAb CDR:LC3; clone: p1.22

<400> SEQUENCE: 217

Gln Gln Tyr Tyr Asp Trp Pro Pro
1               5

<210> SEQ ID NO 218
<211> LENGTH: 8
<212> TYPE: PRT
<213> ORGANISM: Artificial sequence
<220> FEATURE:
<223> OTHER INFORMATION: human mAb CDR:LC3; clone: p1.23

<400> SEQUENCE: 218

Gln Gln Tyr Tyr Asp Trp Pro Pro
1               5

<210> SEQ ID NO 219
<211> LENGTH: 8
<212> TYPE: PRT
<213> ORGANISM: Artificial sequence
<220> FEATURE:
<223> OTHER INFORMATION: human mAb CDR:LC3; clone: p1.24

<400> SEQUENCE: 219
```

Gln Gln Tyr Tyr Asp Trp Pro Pro
1               5

<210> SEQ ID NO 220
<211> LENGTH: 8
<212> TYPE: PRT
<213> ORGANISM: Artificial sequence
<220> FEATURE:
<223> OTHER INFORMATION: human mAb CDR:LC3; clone: p1.25

<400> SEQUENCE: 220

Gln Gln Tyr Tyr Asp Trp Arg Pro
1               5

<210> SEQ ID NO 221
<211> LENGTH: 8
<212> TYPE: PRT
<213> ORGANISM: Artificial sequence
<220> FEATURE:
<223> OTHER INFORMATION: human mAb CDR:LC3; clone: p1.1

<400> SEQUENCE: 221

Gln Gln Tyr Tyr Val Trp Pro Pro
1               5

<210> SEQ ID NO 222
<211> LENGTH: 8
<212> TYPE: PRT
<213> ORGANISM: Artificial sequence
<220> FEATURE:
<223> OTHER INFORMATION: human mAb CDR:LC3; clone: p1.26

<400> SEQUENCE: 222

Gln Gln Tyr Tyr Val Trp Pro Pro
1               5

<210> SEQ ID NO 223
<211> LENGTH: 8
<212> TYPE: PRT
<213> ORGANISM: Artificial sequence
<220> FEATURE:
<223> OTHER INFORMATION: human mAb CDR:LC3; clone: p1.27

<400> SEQUENCE: 223

Gln Gln Tyr Tyr Asp Trp Pro Pro
1               5

<210> SEQ ID NO 224
<211> LENGTH: 8
<212> TYPE: PRT
<213> ORGANISM: Artificial sequence
<220> FEATURE:
<223> OTHER INFORMATION: human mAb CDR:LC3; clone: p1.28

<400> SEQUENCE: 224

Gln Gln Tyr Tyr Asp Trp Pro Pro
1               5

<210> SEQ ID NO 225
<211> LENGTH: 8
<212> TYPE: PRT
<213> ORGANISM: Artificial sequence
<220> FEATURE:
<223> OTHER INFORMATION: human mAb CDR:LC3; clone: p1.29

<400> SEQUENCE: 225

Gln Gln Tyr Asn Asn Trp Pro Pro
1               5

<210> SEQ ID NO 226
<211> LENGTH: 8
<212> TYPE: PRT
<213> ORGANISM: Artificial sequence
<220> FEATURE:
<223> OTHER INFORMATION: human mAb CDR:LC3; clone: p1.30

<400> SEQUENCE: 226

Gln Gln Tyr Tyr Asp Trp Pro Pro
1               5

<210> SEQ ID NO 227
<211> LENGTH: 8
<212> TYPE: PRT
<213> ORGANISM: Artificial sequence
<220> FEATURE:
<223> OTHER INFORMATION: human mAb CDR:LC3; clone: p1.6

<400> SEQUENCE: 227

Gln Gln Tyr Tyr Asp Trp Pro Pro
1               5

<210> SEQ ID NO 228
<211> LENGTH: 8
<212> TYPE: PRT
<213> ORGANISM: Artificial sequence
<220> FEATURE:
<223> OTHER INFORMATION: human mAb CDR:LC3; clone: p1.2

<400> SEQUENCE: 228

Gln Gln Tyr Met Thr Trp Pro Pro
1               5

<210> SEQ ID NO 229
<211> LENGTH: 8
<212> TYPE: PRT
<213> ORGANISM: Artificial sequence
<220> FEATURE:
<223> OTHER INFORMATION: human mAb CDR:LC3; clone: p1.31

<400> SEQUENCE: 229

Gln Gln Tyr Met Thr Trp Pro Pro
1               5

<210> SEQ ID NO 230
<211> LENGTH: 8
<212> TYPE: PRT
<213> ORGANISM: Artificial sequence
<220> FEATURE:
<223> OTHER INFORMATION: human mAb CDR:LC3; clone: p1.5

<400> SEQUENCE: 230

Gln Gln Tyr Asn Asn Trp Pro Pro
1               5

<210> SEQ ID NO 231
<211> LENGTH: 8
<212> TYPE: PRT
<213> ORGANISM: Artificial sequence
<220> FEATURE:
<223> OTHER INFORMATION: human mAb CDR:LC3; clone: p1.32

<400> SEQUENCE: 231

Gln Gln Tyr Tyr Asp Trp Pro Pro

```
<210> SEQ ID NO 232
<211> LENGTH: 8
<212> TYPE: PRT
<213> ORGANISM: Artificial sequence
<220> FEATURE:
<223> OTHER INFORMATION: human mAb CDR:LC3; clone: p1.33

<400> SEQUENCE: 232

Gln Gln Tyr Tyr Asp Trp Arg Pro
1               5

<210> SEQ ID NO 233
<211> LENGTH: 8
<212> TYPE: PRT
<213> ORGANISM: Artificial sequence
<220> FEATURE:
<223> OTHER INFORMATION: human mAb CDR:LC3; clone: p1.39

<400> SEQUENCE: 233

Gln Gln Tyr Met Thr Trp Pro Pro
1               5

<210> SEQ ID NO 234
<211> LENGTH: 8
<212> TYPE: PRT
<213> ORGANISM: Artificial sequence
<220> FEATURE:
<223> OTHER INFORMATION: human mAb CDR:LC3; clone: p1.22

<400> SEQUENCE: 234

Gln Gln Tyr Tyr Asp Trp Pro Pro
1               5

<210> SEQ ID NO 235
<211> LENGTH: 8
<212> TYPE: PRT
<213> ORGANISM: Artificial sequence
<220> FEATURE:
<223> OTHER INFORMATION: human mAb CDR:LC3; clone: p3.1.34

<400> SEQUENCE: 235

Gln Gln Tyr Tyr Asp Trp Pro Pro
1               5

<210> SEQ ID NO 236
<211> LENGTH: 8
<212> TYPE: PRT
<213> ORGANISM: Artificial sequence
<220> FEATURE:
<223> OTHER INFORMATION: human mAb CDR:LC3; clone: p3.1.35

<400> SEQUENCE: 236

Gln Gln Tyr Tyr Asp Trp Pro Pro
1               5

<210> SEQ ID NO 237
<211> LENGTH: 8
<212> TYPE: PRT
<213> ORGANISM: Artificial sequence
<220> FEATURE:
<223> OTHER INFORMATION: human mAb CDR:LC3; clone: p3.1.36

<400> SEQUENCE: 237

Gln Gln Tyr Tyr Asp Trp Pro Pro
1               5
```

<210> SEQ ID NO 238
<211> LENGTH: 8
<212> TYPE: PRT
<213> ORGANISM: Artificial sequence
<220> FEATURE:
<223> OTHER INFORMATION: human mAb CDR:LC3; clone: p3.1.37

<400> SEQUENCE: 238

Gln Gln Tyr Tyr Asp Trp Pro Pro
1               5

<210> SEQ ID NO 239
<211> LENGTH: 8
<212> TYPE: PRT
<213> ORGANISM: Artificial sequence
<220> FEATURE:
<223> OTHER INFORMATION: human mAb CDR:LC3; clone: p3.2.38

<400> SEQUENCE: 239

Gln Gln Tyr Tyr Asp Trp Pro Pro
1               5

<210> SEQ ID NO 240
<211> LENGTH: 8
<212> TYPE: PRT
<213> ORGANISM: Artificial sequence
<220> FEATURE:
<223> OTHER INFORMATION: human mAb CDR:LC3; clone: p3.2.40

<400> SEQUENCE: 240

Gln Gln Tyr Tyr Asp Trp Pro Pro
1               5

<210> SEQ ID NO 241
<211> LENGTH: 1124
<212> TYPE: PRT
<213> ORGANISM: Homo sapiens

<400> SEQUENCE: 241

Met Asp Ser Leu Ala Ser Leu Val Leu Cys Gly Val Ser Leu Leu
1               5                   10                  15

Ser Gly Thr Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
        50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val

```
                165                 170                 175
His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
            195                 200                 205

Arg Arg Cys Glu Ala Gln Lys Trp Gly Pro Glu Cys Asn His Leu Cys
            210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
            275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Gln Arg Met Thr Pro Lys Ile
            340                 345                 350

Val Asp Leu Pro Asp His Ile Glu Val Asn Ser Gly Lys Phe Asn Pro
            355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
            435                 440                 445

Asn Ala Pro Asn Val Ile Asp Thr Gly His Asn Phe Ala Val Ile Asn
450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
            515                 520                 525

His Pro Gly Pro Val Arg Arg Phe Thr Thr Ala Ser Ile Gly Leu Pro
            530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590
```

```
Val Pro Gly Asn Leu Thr Ser Val Leu Asn Asn Leu His Pro Arg
        595                 600                 605

Glu Gln Tyr Val Val Arg Ala Arg Val Asn Thr Lys Ala Gln Gly Glu
610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
                660                 665                 670

Arg Tyr Lys Val Gln Gly Lys Asn Glu Asp Gln His Val Asp Val Lys
                675                 680                 685

Ile Lys Asn Ala Thr Ile Thr Gln Tyr Gln Leu Lys Gly Leu Glu Pro
                690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Lys Met Leu Leu Ile Ala Ile Leu
                740                 745                 750

Gly Ser Ala Gly Met Thr Cys Leu Thr Val Leu Leu Ala Phe Leu Ile
                755                 760                 765

Ile Leu Gln Leu Lys Arg Ala Asn Val Gln Arg Arg Met Ala Gln Ala
                770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
                805                 810                 815

Pro Val Leu Asp Trp Asn Asp Ile Lys Phe Gln Asp Val Ile Gly Glu
                820                 825                 830

Gly Asn Phe Gly Gln Val Leu Lys Ala Arg Ile Lys Lys Asp Gly Leu
                835                 840                 845

Arg Met Asp Ala Ala Ile Lys Arg Met Lys Glu Tyr Ala Ser Lys Asp
                850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
                900                 905                 910

Phe Leu Arg Lys Ser Arg Val Leu Glu Thr Asp Pro Ala Phe Ala Ile
                915                 920                 925

Ala Asn Ser Thr Ala Ser Thr Leu Ser Ser Gln Gln Leu Leu His Phe
                930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
                980                 985                 990

Val Lys Lys Thr Met Gly Arg Leu Pro Val Arg Trp Met Ala Ile Glu
                995                 1000                1005
```

```
Ser Leu Asn Tyr Ser Val Tyr Thr Thr Asn Ser Asp Val Trp Ser
    1010                1015                1020

Tyr Gly Val Leu Leu Trp Glu Ile Val Ser Leu Gly Gly Thr Pro
    1025                1030                1035

Tyr Cys Gly Met Thr Cys Ala Glu Leu Tyr Glu Lys Leu Pro Gln
    1040                1045                1050

Gly Tyr Arg Leu Glu Lys Pro Leu Asn Cys Asp Asp Glu Val Tyr
    1055                1060                1065

Asp Leu Met Arg Gln Cys Trp Arg Glu Lys Pro Tyr Glu Arg Pro
    1070                1075                1080

Ser Phe Ala Gln Ile Leu Val Ser Leu Asn Arg Met Leu Glu Glu
    1085                1090                1095

Arg Lys Thr Tyr Val Asn Thr Leu Tyr Glu Lys Phe Thr Tyr
    1100                1105                1110

Ala Gly Ile Asp Cys Ser Ala Glu Glu Ala Ala
    1115                1120
```

<210> SEQ ID NO 242
<211> LENGTH: 122
<212> TYPE: PRT
<213> ORGANISM: Artificial sequence
<220> FEATURE:
<223> OTHER INFORMATION: human mab p1.1- VH

<400> SEQUENCE: 242

```
Asp Val Gln Leu Val Glu Ser Gly Gly Val Val Arg Pro Gly Glu
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Glu Gly Leu Glu Trp Val
            35                  40                  45

Ala Arg Ile Ser Asp Tyr Thr Ile Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Ser Gly Pro Lys Ser Gly Lys Tyr Trp Asn Asn Phe Phe Asp Ser Trp
                100                 105                 110

Gly Leu Gly Thr Leu Val Thr Val Ser Ser
            115                 120
```

<210> SEQ ID NO 243
<211> LENGTH: 108
<212> TYPE: PRT
<213> ORGANISM: Artificial sequence
<220> FEATURE:
<223> OTHER INFORMATION: human mab p1.1 - VL

<400> SEQUENCE: 243

```
Glu Ile Val Leu Thr Gln Ser Pro Gly Thr Leu Ser Val Ser Pro Gly
1               5                   10                  15

Glu Arg Ala Thr Leu Thr Cys Arg Ala Ser Gln Ser Val Lys Thr Asp
                20                  25                  30

Leu Ala Trp Tyr Gln Gln Lys Pro Gly Gln Ala Pro Arg Leu Leu Ile
            35                  40                  45

Tyr Gly Ala Thr Thr Arg Ala Thr Gly Ile Pro Ala Arg Phe Ser Gly
        50                  55                  60
```

```
Ser Gly Ser Gly Thr Glu Phe Thr Leu Thr Ile Thr Asn Leu Gln Ser
 65                  70                  75                  80

Glu Asp Phe Ala Val Tyr Tyr Cys Gln Gln Tyr Tyr Val Trp Pro Pro
                 85                  90                  95

Leu Thr Phe Gly Gly Gly Thr Lys Val Glu Ile Lys
            100                 105

<210> SEQ ID NO 244
<211> LENGTH: 120
<212> TYPE: PRT
<213> ORGANISM: Artificial sequence
<220> FEATURE:
<223> OTHER INFORMATION: human Mab p1.2 - VH

<400> SEQUENCE: 244

Asp Val Gln Leu Val Glu Ser Gly Gly Gly Val Val Arg Pro Gly Glu
 1               5                  10                  15

Ser Leu Arg Leu Ser Cys Ala Ala Ser Gly Phe Ser Phe Ile Asn Phe
                20                  25                  30

Ala Met Thr Trp Val Arg Gln Ala Pro Gly Glu Gly Pro Glu Trp Val
            35                  40                  45

Ser Leu Ile Ser Asp Asp Gly Arg Gly Asn Arg Pro Tyr Tyr Ala Asp
 50                  55                  60

Ser Val Lys Gly Arg Phe Thr Ile Ser Arg Asp Asn Ser Lys Asn Ile
 65                  70                  75                  80

Leu Tyr Leu Gln Met Asn Ser Leu Arg Val Glu Asp Thr Ala Thr Tyr
                 85                  90                  95

Tyr Cys Ala Lys Val Ser Trp Asp Val Phe Phe Asp Tyr Trp Gly Leu
            100                 105                 110

Gly Thr Val Val Thr Val Ser Ser
            115                 120

<210> SEQ ID NO 245
<211> LENGTH: 108
<212> TYPE: PRT
<213> ORGANISM: Artificial sequence
<220> FEATURE:
<223> OTHER INFORMATION: human Mab p1.2 VL

<400> SEQUENCE: 245

Glu Ile Val Leu Thr Gln Ser Pro Gly Thr Val Ser Leu Ser Pro Gly
 1               5                  10                  15

Glu Arg Val Thr Leu Ser Cys Arg Ala Ser Gln Pro Ile Asp Val Tyr
                20                  25                  30

Leu Ala Trp Tyr Gln Gln Lys Pro Gly Gln Ala Pro Arg Leu Leu Ile
            35                  40                  45

Tyr Gly Ala Asn Arg Arg Ala Ile Asp Ile Pro Asp Arg Phe Ser Gly
 50                  55                  60

Ser Gly Ser Gly Thr Glu Phe Thr Leu Thr Ile Asn Ser Leu Gln Asn
 65                  70                  75                  80

Glu Asp Phe Ala Val Tyr Phe Cys Gln Gln Tyr Met Thr Trp Pro Pro
                 85                  90                  95

Val Thr Phe Gly Gly Gly Thr Lys Val Glu Ile Lys
            100                 105

<210> SEQ ID NO 246
<211> LENGTH: 115
<212> TYPE: PRT
```

```
<213> ORGANISM: Artificial sequence
<220> FEATURE:
<223> OTHER INFORMATION: human Mab p2.3 - VH

<400> SEQUENCE: 246
```

Asp Val Gln Leu Val Glu Ser Gly Gly Val Val Arg Pro Gly Glu
1               5                   10                  15

Ser Leu Arg Leu Ser Cys Thr Ala Ser Gly Phe Thr Phe Asp Ser Tyr
            20                  25                  30

Gly Met Ser Trp Val Arg Gln Ala Pro Gly Lys Gly Leu Glu Trp Val
        35                  40                  45

Ser Ser Ile Asn Val Gly Asp Asn Thr Tyr Tyr Ala Asp Ser Val Arg
50                  55                  60

Gly Arg Phe Ile Ile Ser Arg Asp Ser Ser Arg Asn Thr Leu Tyr Leu
65                  70                  75                  80

Gln Met Asn Ser Leu Thr Ala Glu Asp Thr Ala Val Tyr Tyr Cys Ala
                85                  90                  95

Asn Trp Asn Ser Phe Phe Asp Tyr Trp Gly Leu Gly Thr Leu Val Thr
            100                 105                 110

Val Ser Ser
    115

```
<210> SEQ ID NO 247
<211> LENGTH: 108
<212> TYPE: PRT
<213> ORGANISM: Artificial sequence
<220> FEATURE:
<223> OTHER INFORMATION: human Mab p2.3 - VL

<400> SEQUENCE: 247
```

Glu Ile Val Leu Thr Gln Ser Pro Gly Thr Leu Ser Leu Ser Pro Gly
1               5                   10                  15

Glu Ile Ala Thr Leu Ser Cys Arg Ala Ser Gln Asn Val Arg Ser Asp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Pro
                85                  90                  95

Leu Thr Phe Gly Gly Gly Thr Lys Val Glu Ile Lys
            100                 105

```
<210> SEQ ID NO 248
<211> LENGTH: 115
<212> TYPE: PRT
<213> ORGANISM: Artificial sequence
<220> FEATURE:
<223> OTHER INFORMATION: human mAb p4.1.7 - VH

<400> SEQUENCE: 248
```

Asp Val Gln Leu Val Glu Ser Gly Gly Val Val Arg Pro Gly Glu
1               5                   10                  15

Ser Leu Arg Leu Ser Cys Thr Ala Ser Gly Phe Thr Phe Asp Ser Tyr
            20                  25                  30

Gly Met Ser Trp Val Arg Gln Ala Pro Gly Lys Gly Leu Glu Trp Val
        35                  40                  45

```
Ser Ser Ile Asn Val Gly Asp Asn Thr Tyr Tyr Ala Asp Ser Val Arg
 50                  55                  60

Gly Arg Phe Ile Ile Ser Arg Asp Ser Ser Arg Asn Thr Leu Tyr Leu
 65                  70                  75                  80

Gln Met Asn Ser Leu Thr Ala Glu Asp Thr Ala Val Tyr Tyr Cys Ala
                 85                  90                  95

Asn Trp Asn Ser Phe Phe Asp Tyr Trp Gly Leu Gly Thr Leu Val Thr
                100                 105                 110

Val Ser Ser
        115

<210> SEQ ID NO 249
<211> LENGTH: 108
<212> TYPE: PRT
<213> ORGANISM: Artificial sequence
<220> FEATURE:
<223> OTHER INFORMATION: human mAb p4.1.7 - VL

<400> SEQUENCE: 249

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Asp Ala Ser Ser Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Leu Tyr Tyr Cys Gln Gln Tyr Asn Asn Trp Pro Pro
                 85                 90                   95

Leu Thr Phe Gly Gly Gly Thr Lys Val Glu Ile Lys
                100                 105

<210> SEQ ID NO 250
<211> LENGTH: 117
<212> TYPE: PRT
<213> ORGANISM: Artificial sequence
<220> FEATURE:
<223> OTHER INFORMATION: human mAb p4.3.41 - VH

<400> SEQUENCE: 250

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ile Tyr
                20                  25                  30

Ala Met Asn Trp Val Arg Gln Ala Pro Gly Glu Gly Leu Glu Trp Ile
            35                  40                  45

Ser Gly Ile Ser Gly Ser Gly Ala Leu Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                 95

Ala Lys Pro Leu Asn Asn Phe Phe Asp Tyr Trp Gly Leu Gly Thr Leu
                100                 105                 110

Val Thr Val Ser Ser
```

```
               115

<210> SEQ ID NO 251
<211> LENGTH: 108
<212> TYPE: PRT
<213> ORGANISM: Artificial sequence
<220> FEATURE:
<223> OTHER INFORMATION: human mAb p4.3.41 - VL

<400> SEQUENCE: 251

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Lys
            20                  25                  30

Leu Ala Trp Tyr Gln Gln Lys Pro Gly Gln Ala Pro Arg Leu Leu Ile
        35                  40                  45

Phe Tyr Ala Ser Ser Arg Ala Thr Gly Ile Pro Asp Arg Phe Ser Gly
    50                  55                  60

Ser Gly Ser Gly Thr Asp Phe Thr Leu Thr Ile Arg Ser Leu Gln Ser
65                  70                  75                  80

Glu Asp Phe Ala Val Tyr Tyr Cys Gln Gln Tyr His Asp Trp Pro Pro
                85                  90                  95

Leu Thr Phe Gly Gly Gly Thr Lys Val Glu Ile Lys
            100                 105

<210> SEQ ID NO 252
<211> LENGTH: 115
<212> TYPE: PRT
<213> ORGANISM: Artificial sequence
<220> FEATURE:
<223> OTHER INFORMATION: human mAb p4.3.42 - VH

<400> SEQUENCE: 252

Asp Val Gln Leu Val Glu Ser Gly Gly Gly Val Val Arg Pro Gly Glu
1               5                   10                  15

Ser Leu Arg Leu Ser Cys Thr Ala Ser Gly Phe Thr Phe Asp Ser Tyr
            20                  25                  30

Gly Met Ser Trp Val Arg Gln Ala Pro Gly Lys Gly Leu Glu Trp Val
        35                  40                  45

Ser Ser Ile Asn Val Gly Asp Asn Thr Tyr Tyr Ala Asp Ser Val Arg
    50                  55                  60

Gly Arg Phe Ile Ile Ser Arg Asp Ser Ser Arg Asn Thr Leu Tyr Leu
65                  70                  75                  80

Gln Met Asn Ser Leu Thr Ala Glu Asp Thr Ala Val Tyr Tyr Cys Ala
                85                  90                  95

Asn Trp Asn Ser Phe Phe Asp Tyr Trp Gly Leu Gly Thr Leu Val Thr
            100                 105                 110

Val Ser Ser
        115

<210> SEQ ID NO 253
<211> LENGTH: 108
<212> TYPE: PRT
<213> ORGANISM: Artificial sequence
<220> FEATURE:
<223> OTHER INFORMATION: human mAb p4.3.42 - VL

<400> SEQUENCE: 253

Glu Ile Val Leu Thr Gln Ser Pro Gly Thr Leu Ser Ser Ser Pro Gly
1               5                   10                  15
```

```
Glu Arg Ala Thr Leu Ser Cys Arg Ala Ser Gln Thr Val Gly Ser Tyr
            20                  25                  30

Leu Ala Trp Tyr Gln Gln Lys Pro Gly Gln Ala Pro Arg Leu Leu Ile
        35                  40                  45

Tyr Ala Ala Ser Ser Arg Ala Thr Gly Ile Pro Asp Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Asp Trp Pro Pro
                85                  90                  95

Leu Thr Phe Gly Gly Gly Thr Lys Val Glu Ile Lys
            100                 105
```

<210> SEQ ID NO 254
<211> LENGTH: 118
<212> TYPE: PRT
<213> ORGANISM: Artificial sequence
<220> FEATURE:
<223> OTHER INFORMATION: human mAb p5.43 - VH

<400> SEQUENCE: 254

```
Asp Val Gln Leu Val Glu Ser Gly Gly Gly Leu Val Gln Pro Gly Glu
1               5                   10                  15

Ser Leu Arg Leu Ser Cys Thr Ala Ser Gly Phe Thr Phe Pro Thr Tyr
            20                  25                  30

Ala Leu Ser Trp Val Arg Gln Ala Pro Gly Glu Gly Leu Glu Trp Val
        35                  40                  45

Ser Ser Thr Ile Trp Gly Gly Asp Thr Thr Tyr Tyr Ala Glu Ser Val
50                  55                  60

Lys Gly Arg Phe Ile Ile Ser Arg Asp Ser Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Gln Gly Thr Trp Asn Ile Phe Phe Asp Tyr Trp Gly Leu Gly Val
            100                 105                 110

Leu Val Thr Val Ser Ser
        115
```

<210> SEQ ID NO 255
<211> LENGTH: 108
<212> TYPE: PRT
<213> ORGANISM: Artificial sequence
<220> FEATURE:
<223> OTHER INFORMATION: human mAb p5.43 - VL

<400> SEQUENCE: 255

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ala Gly Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
```

```
                    85                  90                  95

Leu Thr Phe Gly Gly Gly Thr Lys Val Glu Ile Lys
                100                 105

<210> SEQ ID NO 256
<211> LENGTH: 117
<212> TYPE: PRT
<213> ORGANISM: Artificial sequence
<220> FEATURE:
<223> OTHER INFORMATION: human mAb p4.2.44 - VH

<400> SEQUENCE: 256

Asp Val Gln Leu Val Glu Ser Gly Gly Val Val Arg Pro Gly Glu
1               5                   10                  15

Ser Leu Arg Leu Ser Cys Ala Ala Ser Gly Phe Ser Phe Ser Leu Tyr
            20                  25                  30

Ala Met Asn Trp Val Arg Gln Ala Pro Gly Glu Gly Leu Glu Trp Val
        35                  40                  45

Ser Arg Ile Ser Gly Arg Asp Gly Tyr Thr Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Lys Thr Leu Asn Asn Phe Phe Asp Tyr Trp Gly Leu Gly Thr Leu
                100                 105                 110

Val Thr Val Ser Leu
            115

<210> SEQ ID NO 257
<211> LENGTH: 109
<212> TYPE: PRT
<213> ORGANISM: Artificial sequence
<220> FEATURE:
<223> OTHER INFORMATION: human mAb p4.2.44 - VL

<400> SEQUENCE: 257

Glu Ile Val Leu Thr Gln Ser Pro Gly Thr Leu Ile Leu Ser Pro Gly
1               5                   10                  15

Glu Arg Ala Thr Leu Ser Cys Arg Ala Ser Gln Ser Ile Ser Asn Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Asn Arg Ala Ala Asp Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Tyr Asp Trp Pro
                85                  90                  95

Pro Leu Thr Phe Gly Gly Gly Thr Lys Val Glu Ile Lys
                100                 105

<210> SEQ ID NO 258
<211> LENGTH: 114
<212> TYPE: PRT
<213> ORGANISM: Artificial sequence
<220> FEATURE:
<223> OTHER INFORMATION: human mAb p5.45  VH

<400> SEQUENCE: 258
```

```
Asp Val Gln Leu Val Glu Ser Gly Gly Gly Val Val Arg Pro Gly Glu
1               5                   10                  15

Ser Leu Thr Leu Ser Cys Ala Ala Ser Gly Phe Thr Phe Ser Ser Tyr
            20                  25                  30

Gly Met Ser Trp Val Arg Gln Ala Pro Gly Glu Gly Leu Glu Trp Val
        35                  40                  45

Ser Ala Ile Asn Gly Gly Ser Thr Phe Tyr Ala Asp Ser Val Lys Gly
    50                  55                  60

Arg Phe Thr Ile Ser Arg Asp Asn Ser Lys Asn Ile Leu Tyr Leu Gln
65                  70                  75                  80

Met Asn Ser Leu Arg Ala Glu Asp Thr Ala Ile Tyr Tyr Cys Ala Asn
                85                  90                  95

Trp Asn Ser Phe Phe Asp Tyr Trp Gly Leu Gly Thr Leu Val Thr Val
            100                 105                 110

Ser Ser
```

<210> SEQ ID NO 259
<211> LENGTH: 108
<212> TYPE: PRT
<213> ORGANISM: Artificial sequence
<220> FEATURE:
<223> OTHER INFORMATION: human mAb p5.45  VL

<400> SEQUENCE: 259

```
Glu Ile Val Leu Thr Gln Ser Pro Gly Thr Leu Ser Leu Ser Pro Gly
1               5                   10                  15

Glu Arg Ala Thr Leu Thr Cys Arg Ala Ser Gln His Val Asn Thr His
            20                  25                  30

Val Ala Trp Tyr Gln Gln Arg Pro Gly Gln Ala Pro Arg Leu Ile Ile
        35                  40                  45

Tyr Asp Ala Thr Asn Arg Ala Asn Asp Val Pro Asp Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Tyr Asn Asn Trp Pro Pro
                85                  90                  95

Leu Thr Phe Gly Gly Gly Thr Lys Val Glu Ile Lys
            100                 105
```

<210> SEQ ID NO 260
<211> LENGTH: 114
<212> TYPE: PRT
<213> ORGANISM: Artificial sequence
<220> FEATURE:
<223> OTHER INFORMATION: human mAb p5.46 - VH

<400> SEQUENCE: 260

```
Asp Val Gln Leu Val Glu Ser Gly Gly Gly Val Val Arg Pro Gly Glu
1               5                   10                  15

Ser Leu Thr Leu Ser Cys Val Ala Ser Gly Phe Thr Phe Ser Ser Tyr
            20                  25                  30

Gly Met Ser Trp Val Arg Gln Ala Pro Gly Glu Gly Leu Glu Trp Val
        35                  40                  45

Ser Ala Ile Asn Gly Gly Ser Thr Phe Tyr Ala Asp Ser Val Lys Gly
    50                  55                  60

Arg Phe Thr Ile Ser Arg Asp Asn Ser Lys Asn Ile Leu Tyr Leu Gln
65                  70                  75                  80
```

```
Met Asn Ser Leu Arg Ala Glu Asp Thr Ala Ile Tyr Tyr Cys Ala Asn
            85                  90                  95

Trp Asn Ser Phe Phe Asp Tyr Trp Gly Leu Gly Thr Leu Val Thr Val
            100                 105                 110

Ser Ser

<210> SEQ ID NO 261
<211> LENGTH: 108
<212> TYPE: PRT
<213> ORGANISM: Artificial sequence
<220> FEATURE:
<223> OTHER INFORMATION: human mAb p5.46 - VL

<400> SEQUENCE: 261

Glu Ile Val Leu Thr Gln Ser Pro Gly Thr Leu Ser Leu Ser Pro Gly
1               5                   10                  15

Glu Arg Ala Thr Leu Thr Cys Arg Ala Ser Gln His Val Asn Thr His
            20                  25                  30

Val Ala Trp Tyr Gln Gln Arg Pro Gly Gln Ala Pro Arg Leu Ile Ile
            35                  40                  45

Tyr Asp Ala Thr Asn Arg Ala Asn Asp Val Pro Asp Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Tyr Asn Asn Trp Pro Pro
            85                  90                  95

Leu Thr Phe Gly Gly Gly Thr Lys Val Glu Ile Lys
            100                 105

<210> SEQ ID NO 262
<211> LENGTH: 119
<212> TYPE: PRT
<213> ORGANISM: Artificial sequence
<220> FEATURE:
<223> OTHER INFORMATION: human mAb p1.6 - VH

<400> SEQUENCE: 262

Asp Val Gln Leu Val Glu Ser Gly Gly Val Val Arg Pro Gly Glu
1               5                   10                  15

Ser Leu Arg Leu Ser Cys Thr Ala Ser Gly Phe Ser Phe Asp Val Tyr
            20                  25                  30

Ala Met Thr Trp Val Arg Gln Ala Pro Gly Lys Gly Leu Glu Trp Leu
            35                  40                  45

Thr Leu Ile Ser Gly Thr Gly Arg Met Thr Tyr Tyr Ala Asp Ser Val
    50                  55                  60

Lys Gly Arg Phe Thr Val Ser Arg Asp Asn Ser Lys Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Pro Phe Gly His Gly Phe Phe Asp Tyr Trp Gly Leu Gly
            100                 105                 110

Thr Leu Val Thr Val Ser Ser
            115

<210> SEQ ID NO 263
<211> LENGTH: 108
<212> TYPE: PRT
<213> ORGANISM: Artificial sequence
```

<220> FEATURE:
<223> OTHER INFORMATION: human mAb p1.6 - VL

<400> SEQUENCE: 263

```
Glu Ile Val Leu Thr Gln Ser Pro Gly Thr Leu Thr Leu Ser Pro Gly
1               5                   10                  15

Glu Thr Ala Thr Leu Thr Cys Arg Ala Ser Gln Ser Val Asn Arg Asn
            20                  25                  30

Leu Ala Trp Tyr Gln Glu Lys Pro Asp Gln Ala Pro Arg Leu Leu Ile
        35                  40                  45

Tyr Asp Ala Arg Thr Arg Ala Thr Gly Val Pro Asp Arg Phe Ser Gly
    50                  55                  60

Ser Gly Ser Gly Thr Asp Phe Thr Leu Thr Ile Asn Ser Leu Gln Ser
65                  70                  75                  80

Glu Asp Phe Ala Val Tyr Val Cys Gln Gln Tyr Tyr Asp Trp Pro Pro
                85                  90                  95

Phe Thr Phe Gly Gly Gly Thr Lys Val Glu Ile Lys
            100                 105
```

<210> SEQ ID NO 264
<211> LENGTH: 122
<212> TYPE: PRT
<213> ORGANISM: Artificial sequence
<220> FEATURE:
<223> OTHER INFORMATION: human mAb p4.2.47 - VH

<400> SEQUENCE: 264

```
Asp Val Gln Leu Val Glu Ser Gly Gly Gly Glu Val Arg Pro Gly Glu
1               5                   10                  15

Pro Leu Arg Leu Ser Cys Ala Ala Ser Gly Phe Thr Phe Asn Thr Tyr
            20                  25                  30

Gly Met Ser Trp Val Arg Gln Ala Pro Gly Glu Gly Leu Glu Trp Val
        35                  40                  45

Ser Val Ile Ser Gly Ser Gly Gly Ser Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Ile Tyr Tyr Cys
                85                  90                  95

Ala Lys Asp Ser Gly Ser Trp Thr Ser Ser Gly Phe Phe Asp Tyr Trp
            100                 105                 110

Gly Leu Gly Thr Leu Val Thr Val Ser Ser
        115                 120
```

<210> SEQ ID NO 265
<211> LENGTH: 108
<212> TYPE: PRT
<213> ORGANISM: Artificial sequence
<220> FEATURE:
<223> OTHER INFORMATION: human mAb p4.2.47 - VL

<400> SEQUENCE: 265

```
Glu Ile Val Leu Thr Gln Ser Pro Gly Thr Leu Ser Val Ser Pro Gly
1               5                   10                  15

Glu Lys Ala Thr Leu Asn Cys Arg Ala Ser Gln Asn Ile Asn Ser Lys
            20                  25                  30

Leu Ala Trp Tyr Gln Gln Lys Pro Gly Gln Ala Pro Arg Leu Leu Ile
        35                  40                  45
```

Tyr Asp Ala Gly Asn Arg Ala Ala Gly Ile Pro Asp Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Trp Arg Pro
                85                  90                  95

Leu Thr Phe Gly Gly Gly Thr Lys Val Glu Ile Lys
            100                 105

<210> SEQ ID NO 266
<211> LENGTH: 117
<212> TYPE: PRT
<213> ORGANISM: Artificial sequence
<220> FEATURE:
<223> OTHER INFORMATION: human mAb p5.48 - VH

<400> SEQUENCE: 266

Asp Val Gln Leu Val Glu Ser Gly Gly Ala Val Val Arg Pro Gly Glu
1               5                   10                  15

Ser Leu Arg Leu Ser Cys Ala Ala Ser Gly Phe Ser Phe Asp Ile Tyr
                20                  25                  30

Gly Met Asn Trp Val Arg Gln Ala Pro Gly Lys Gly Leu Glu Trp Val
            35                  40                  45

Ser Arg Ile Ser Gly Asn Gly Gly Ser Thr Phe Tyr Ser Glu Ser Val
        50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Leu Asn Asn Phe Phe Asp Tyr Trp Gly Leu Gly Thr Leu
                100                 105                 110

Val Thr Val Ser Ser
            115

<210> SEQ ID NO 267
<211> LENGTH: 108
<212> TYPE: PRT
<213> ORGANISM: Artificial sequence
<220> FEATURE:
<223> OTHER INFORMATION: human mAb p5.48 - VL

<400> SEQUENCE: 267

Glu Ile Val Leu Thr Gln Ser Pro Gly Thr Leu Ser Val Ser Pro Gly
1               5                   10                  15

Glu Arg Ala Thr Leu Ser Cys Arg Ala Ser Gln His Val Gly Gly Asn
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Asp Arg Phe Ser Gly
        50                  55                  60

Ser Gly Ser Gly Thr Asp Phe Ser Leu Thr Ile Ser Arg Leu Glu Pro
65                  70                  75                  80

Glu Asp Phe Ala Val Tyr Tyr Cys Gln Gln Tyr Tyr Asp Trp Pro Pro
                85                  90                  95

Leu Thr Phe Gly Gly Gly Thr Lys Val Glu Ile Lys
            100                 105

<210> SEQ ID NO 268

```
<211> LENGTH: 119
<212> TYPE: PRT
<213> ORGANISM: Artificial sequence
<220> FEATURE:
<223> OTHER INFORMATION: human mAb p1.5 - VH

<400> SEQUENCE: 268
```

Asp Val Gln Leu Val Glu Ser Gly Gly Gly Val Val Arg Pro Gly Glu
1               5                   10                  15

Ser Leu Arg Leu Ser Cys Thr Ala Ser Gly Phe Ser Phe Asp Val Tyr
            20                  25                  30

Ala Met Thr Trp Val Arg Gln Ala Pro Gly Lys Gly Leu Glu Trp Leu
        35                  40                  45

Thr Leu Ile Ser Gly Thr Gly Arg Met Thr Tyr Tyr Ala Asp Ser Val
    50                  55                  60

Lys Gly Arg Phe Thr Val Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Phe Gly His Gly Phe Phe Asp Tyr Trp Gly Leu Gly
            100                 105                 110

Thr Leu Val Thr Val Ser Ser
        115

```
<210> SEQ ID NO 269
<211> LENGTH: 108
<212> TYPE: PRT
<213> ORGANISM: Artificial sequence
<220> FEATURE:
<223> OTHER INFORMATION: human mAb p1.5 - VL

<400> SEQUENCE: 269
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Gly Ser Lys
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Asp Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Leu Thr Phe Gly Gly Gly Thr Lys Val Glu Ile Lys
            100                 105

```
<210> SEQ ID NO 270
<211> LENGTH: 120
<212> TYPE: PRT
<213> ORGANISM: Artificial sequence
<220> FEATURE:
<223> OTHER INFORMATION: human mAb p3.2.49 - VH

<400> SEQUENCE: 270
```

Asp Val Gln Leu Val Glu Ser Gly Gly Gly Val Val Arg Pro Gly Glu
1               5                   10                  15

Ser Leu Arg Leu Ser Cys Ser Ala Ser Gly Phe Thr Phe Asp Ile Tyr
            20                  25                  30

Ala Met Thr Trp Val Arg Gln Ala Pro Gly Glu Gly Leu Glu Trp Val
            35                  40                  45

Ser Thr Leu Thr Gly Ile Ser Gly Arg Gly Gly Ser Thr Phe Tyr Ala
 50                  55                  60

Asp Ser Val Lys Gly Arg Phe Thr Ile Ser Arg Asp Ser Ser Asp Asn
 65                  70                  75                  80

Ile Leu Tyr Leu Gln Met Asn Ser Leu Arg Ala Glu Asp Thr Ala Ile
            85                  90                  95

Tyr Tyr Cys Ala Gly Gly Thr Asp Ile Phe Phe Asp Tyr Trp Gly Leu
            100                 105                 110

Gly Ile Leu Val Thr Val Ser Ser
            115                 120

<210> SEQ ID NO 271
<211> LENGTH: 108
<212> TYPE: PRT
<213> ORGANISM: Artificial sequence
<220> FEATURE:
<223> OTHER INFORMATION: human mAb p3.2.49 - VL

<400> SEQUENCE: 271

Glu Met Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asn Tyr
            20                  25                  30

Leu Ala Trp Tyr Gln Gln Lys Pro Gly Gln Ala Pro Arg Leu Leu Ile
            35                  40                  45

Tyr Asp Ala Ser Ser Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Pro
            85                  90                  95

Leu Thr Phe Gly Gly Gly Thr Lys Val Glu Ile Lys
            100                 105

<210> SEQ ID NO 272
<211> LENGTH: 120
<212> TYPE: PRT
<213> ORGANISM: Artificial sequence
<220> FEATURE:
<223> OTHER INFORMATION: human mAb p1.31 - VH

<400> SEQUENCE: 272

Asp Val Gln Leu Val Glu Ser Gly Gly Gly Val Val Arg Pro Gly Glu
1               5                   10                  15

Ser Pro Arg Leu Ser Cys Ala Ala Ser Gly Phe Ser Phe Ile Asn Phe
            20                  25                  30

Ala Met Thr Trp Val Arg Gln Ala Pro Gly Glu Gly Pro Glu Trp Val
            35                  40                  45

Ser Leu Ile Ser Asp Asp Gly Arg Gly Asn Arg Pro Tyr Tyr Ala Asp
 50                  55                  60

Ser Val Lys Gly Arg Phe Thr Ile Ser Arg Asp Asn Ser Lys Asn Ile
 65                  70                  75                  80

Leu Tyr Leu Gln Met Asn Ser Leu Arg Val Glu Asp Thr Ala Thr Tyr
            85                  90                  95

Tyr Cys Ala Lys Val Ser Trp Asp Val Phe Phe Asp Tyr Trp Gly Leu
            100                 105                 110

```
Gly Thr Leu Val Thr Val Ser Ser
        115                 120

<210> SEQ ID NO 273
<211> LENGTH: 108
<212> TYPE: PRT
<213> ORGANISM: Artificial sequence
<220> FEATURE:
<223> OTHER INFORMATION: human mAb p1.31 - VL

<400> SEQUENCE: 273

Glu Ile Val Leu Thr Gln Ser Pro Gly Thr Val Ser Leu Ser Pro Gly
1               5                   10                  15

Glu Arg Val Thr Leu Ser Cys Arg Ala Ser Gln Pro Ile Asp Val Tyr
            20                  25                  30

Leu Ala Trp Tyr Gln Gln Lys Pro Gly Gln Ala Pro Arg Leu Leu Ile
        35                  40                  45

Tyr Gly Ala Asn Arg Arg Ala Ile Asp Ile Pro Asp Arg Phe Ser Gly
    50                  55                  60

Ser Gly Ser Gly Thr Glu Phe Thr Leu Thr Ile Asn Ser Leu Gln Asn
65                  70                  75                  80

Glu Asp Phe Ala Val Tyr Phe Cys Gln Gln Tyr Met Thr Trp Pro Pro
                85                  90                  95

Val Thr Phe Gly Gly Gly Thr Lys Val Glu Ile Lys
            100                 105

<210> SEQ ID NO 274
<211> LENGTH: 445
<212> TYPE: PRT
<213> ORGANISM: Artificial sequence
<220> FEATURE:
<223> OTHER INFORMATION: Artificial p2.3 with pro-hexamerizing and
      ADCC/CDC abrogating Fc mutations (heavy chain)

<400> SEQUENCE: 274

Asp Val Gln Leu Val Glu Ser Gly Gly Gly Val Val Arg Pro Gly Glu
1               5                   10                  15

Ser Leu Arg Leu Ser Cys Thr Ala Ser Gly Phe Thr Phe Asp Ser Tyr
            20                  25                  30

Gly Met Ser Trp Val Arg Gln Ala Pro Gly Lys Gly Leu Glu Trp Val
        35                  40                  45

Ser Ser Ile Asn Val Gly Asp Asn Thr Tyr Tyr Ala Asp Ser Val Arg
    50                  55                  60

Gly Arg Phe Ile Ile Ser Arg Asp Ser Ser Arg Asn Thr Leu Tyr Leu
65                  70                  75                  80

Gln Met Asn Ser Leu Thr Ala Glu Asp Thr Ala Val Tyr Tyr Cys Ala
                85                  90                  95

Asn Trp Asn Ser Phe Phe Asp Tyr Trp Gly Leu Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Gly Ala Leu His Asn
            420                 425                 430

His Tyr Thr Gln Lys Ser Leu Ser Leu Ser Pro Gly Lys
            435                 440                 445

<210> SEQ ID NO 275
<211> LENGTH: 215
<212> TYPE: PRT
<213> ORGANISM: Artificial sequence
<220> FEATURE:
<223> OTHER INFORMATION: Artificial p2.3 with pro-hexamerizing and
      ADCC/CDC abrogating Fc mutations (light chain (kappa))

<400> SEQUENCE: 275

Glu Ile Val Leu Thr Gln Ser Pro Gly Thr Leu Ser Leu Ser Pro Gly
1               5                   10                  15

Glu Ile Ala Thr Leu Ser Cys Arg Ala Ser Gln Asn Val Arg Ser Asp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Pro
                85                  90                  95
```

-continued

```
Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 276
<211> LENGTH: 696
<212> TYPE: PRT
<213> ORGANISM: Artificial sequence
<220> FEATURE:
<223> OTHER INFORMATION: Artificial p2.3 IgG-scFv fusion tetravalent mAb
      with HC C-terminal p2.3-scFv and ADCC/CDC abrogating Fc mutations
      (heavy chain)

<400> SEQUENCE: 276

Asp Val Gln Leu Val Glu Ser Gly Gly Gly Val Val Arg Pro Gly Glu
1               5                   10                  15

Ser Leu Ar

-continued

```
Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys Gly Gly Gly
    435                 440                 445

Gly Ser Gly Gly Gly Ser Glu Ile Val Leu Thr Gln Ser Pro Gly
450                 455                 460

Thr Leu Ser Leu Ser Pro Gly Glu Ile Ala Thr Leu Ser Cys Arg Ala
465                 470                 475                 480

Ser Gln Asn Val Arg Ser Asp Leu Ala Trp Tyr Gln Gln Lys Pro Gly
            485                 490                 495

Gln Ala Pro Arg Leu Leu Ile Tyr Asp Ala Ser Asn Arg Ala Thr Gly
        500                 505                 510

Ile Pro Asp Arg Phe Ser Gly Ser Gly Ser Gly Thr Asp Phe Thr Leu
    515                 520                 525

Thr Ile Ser Ser Leu Gln Ser Glu Asp Phe Ala Val Tyr Tyr Cys Gln
530                 535                 540

Gln Tyr Ser Asn Trp Pro Pro Leu Thr Phe Gly Gly Gly Thr Lys Val
545                 550                 555                 560

Glu Ile Lys Gly Gln Ser Ser Arg Ser Ser Gly Gly Gly Ser Ser
            565                 570                 575

Gly Gly Gly Gly Ser Asp Val Gln Leu Val Glu Ser Gly Gly Gly Val
        580                 585                 590

Val Arg Pro Gly Glu Ser Leu Arg Leu Ser Cys Thr Ala Ser Gly Phe
    595                 600                 605

Thr Phe Asp Ser Tyr Gly Met Ser Trp Val Arg Gln Ala Pro Gly Lys
610                 615                 620

Gly Leu Glu Trp Val Ser Ser Ile Asn Val Gly Asp Asn Thr Tyr Tyr
625                 630                 635                 640

Ala Asp Ser Val Arg Gly Arg Phe Ile Ile Ser Arg Asp Ser Ser Arg
```

```
                    645                 650                 655
Asn Thr Leu Tyr Leu Gln Met Asn Ser Leu Thr Ala Glu Asp Thr Ala
                660                 665                 670

Val Tyr Tyr Cys Ala Asn Trp Asn Ser Phe Phe Asp Tyr Trp Gly Leu
            675                 680                 685

Gly Thr Leu Val Thr Val Ser Ser
        690                 695
```

<210> SEQ ID NO 277
<211> LENGTH: 215
<212> TYPE: PRT
<213> ORGANISM: Artificial sequence
<220> FEATURE:
<223> OTHER INFORMATION: Artificial p2.3 IgG-scFv fusion tetravalent
      mAb with HC C-terminal p2.3-scFv and ADCC/CDC abrogating Fc
      mutations (light chain (kappa))

<400> SEQUENCE: 277

```
Glu Ile Val Leu Thr Gln Ser Pro Gly Thr Leu Ser Leu Ser Pro Gly
1               5                   10                  15

Glu Ile Ala Thr Leu Ser Cys Arg Ala Ser Gln Asn Val Arg Ser Asp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 278
<211> LENGTH: 696
<212> TYPE: PRT
<213> ORGANISM: Artificial sequence
<220> FEATURE:
<223> OTHER INFORMATION: Artificial p2.3 IgG-scFv fusion tetravalent mAb
      with HC N-terminal p2.3-scFv and ADCC/CDC abrogating Fc mutations
      (heavy chain)

<400> SEQUENCE: 278

```
Glu Ile Val Leu Thr Gln Ser Pro Gly Thr Leu Ser Leu Ser Pro Gly
1               5                   10                  15
```

```
Glu Ile Ala Thr Leu Ser Cys Arg Ala Ser Gln Asn Val Arg Ser Asp
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Asp Arg Phe Ser Gly
 50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Pro
                 85                  90                  95

Leu Thr Phe Gly Gly Gly Thr Lys Val Glu Ile Lys Gly Gln Ser Ser
             100                 105                 110

Arg Ser Ser Gly Gly Gly Gly Ser Gly Gly Gly Gly Ser Asp Val
             115                 120                 125

Gln Leu Val Glu Ser Gly Gly Val Val Arg Pro Gly Glu Ser Leu
130                 135                 140

Arg Leu Ser Cys Thr Ala Ser Gly Phe Thr Phe Asp Ser Tyr Gly Met
145                 150                 155                 160

Ser Trp Val Arg Gln Ala Pro Gly Lys Gly Leu Glu Trp Val Ser Ser
                 165                 170                 175

Ile Asn Val Gly Asp Asn Thr Tyr Tyr Ala Asp Ser Val Arg Gly Arg
             180                 185                 190

Phe Ile Ile Ser Arg Asp Ser Ser Arg Asn Thr Leu Tyr Leu Gln Met
         195                 200                 205

Asn Ser Leu Thr Ala Glu Asp Thr Ala Val Tyr Tyr Cys Ala Asn Trp
210                 215                 220

Asn Ser Phe Phe Asp Tyr Trp Gly Leu Gly Thr Leu Val Thr Val Ser
225                 230                 235                 240

Ser Gly Gly Gly Gly Ser Gly Gly Gly Gly Ser Asp Val Gln Leu Val
                 245                 250                 255

Glu Ser Gly Gly Gly Val Val Arg Pro Gly Glu Ser Leu Arg Leu Ser
             260                 265                 270

Cys Thr Ala Ser Gly Phe Thr Phe Asp Ser Tyr Gly Met Ser Trp Val
         275                 280                 285

Arg Gln Ala Pro Gly Lys Gly Leu Glu Trp Val Ser Ser Ile Asn Val
290                 295                 300

Gly Asp Asn Thr Tyr Tyr Ala Asp Ser Val Arg Gly Arg Phe Ile Ile
305                 310                 315                 320

Ser Arg Asp Ser Ser Arg Asn Thr Leu Tyr Leu Gln Met Asn Ser Leu
                 325                 330                 335

Thr Ala Glu Asp Thr Ala Val Tyr Tyr Cys Ala Asn Trp Asn Ser Phe
             340                 345                 350

Phe Asp Tyr Trp Gly Leu Gly Thr Leu Val Thr Val Ser Ser Ala Ser
         355                 360                 365

Thr Lys Gly Pro Ser Val Phe Pro Leu Ala Pro Ser Ser Lys Ser Thr
370                 375                 380

Ser Gly Gly Thr Ala Ala Leu Gly Cys Leu Val Lys Asp Tyr Phe Pro
385                 390                 395                 400

Glu Pro Val Thr Val Ser Trp Asn Ser Gly Ala Leu Thr Ser Gly Val
                 405                 410                 415

His Thr Phe Pro Ala Val Leu Gln Ser Ser Gly Leu Tyr Ser Leu Ser
             420                 425                 430
```

```
Ser Val Val Thr Val Pro Ser Ser Leu Gly Thr Gln Thr Tyr Ile
        435                 440                 445

Cys Asn Val Asn His Lys Pro Ser Asn Thr Lys Val Asp Lys Lys Val
450                 455                 460

Glu Pro Lys Ser Cys Asp Lys Thr His Thr Cys Pro Pro Cys Pro Ala
465                 470                 475                 480

Pro Glu Ala Ala Gly Gly Pro Ser Val Phe Leu Phe Pro Pro Lys Pro
            485                 490                 495

Lys Asp Thr Leu Met Ile Ser Arg Thr Pro Glu Val Thr Cys Val Val
                500                 505                 510

Val Asp Val Ser His Glu Asp Pro Glu Val Lys Phe Asn Trp Tyr Val
        515                 520                 525

Asp Gly Val Glu Val His Asn Ala Lys Thr Lys Pro Arg Glu Glu Gln
    530                 535                 540

Tyr Asn Ser Thr Tyr Arg Val Val Ser Val Leu Thr Val Leu His Gln
545                 550                 555                 560

Asp Trp Leu Asn Gly Lys Glu Tyr Lys Cys Lys Val Ser Asn Lys Ala
                565                 570                 575

Leu Gly Ala Pro Ile Glu Lys Thr Ile Ser Lys Ala Lys Gly Gln Pro
            580                 585                 590

Arg Glu Pro Gln Val Tyr Thr Leu Pro Pro Ser Arg Glu Glu Met Thr
        595                 600                 605

Lys Asn Gln Val Ser Leu Thr Cys Leu Val Lys Gly Phe Tyr Pro Ser
    610                 615                 620

Asp Ile Ala Val Glu Trp Glu Ser Asn Gly Gln Pro Glu Asn Asn Tyr
625                 630                 635                 640

Lys Thr Thr Pro Pro Val Leu Asp Ser Asp Gly Ser Phe Phe Leu Tyr
                645                 650                 655

Ser Lys Leu Thr Val Asp Lys Ser Arg Trp Gln Gln Gly Asn Val Phe
            660                 665                 670

Ser Cys Ser Val Met His Glu Ala Leu His Asn His Tyr Thr Gln Lys
        675                 680                 685

Ser Leu Ser Leu Ser Pro Gly Lys
    690                 695

<210> SEQ ID NO 279
<211> LENGTH: 215
<212> TYPE: PRT
<213> ORGANISM: Artificial sequence
<220> FEATURE:
<223> OTHER INFORMATION: Artificial p2.3 IgG-scFv fusion tetravalent mAb
      with HC N-terminal p2.3-scFv and ADCC/CDC abrogating Fc mutations
      (light chain (kappa))

<400> SEQUENCE: 279

```
                        85                  90                  95
Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 280
<211> LENGTH: 701
<212> TYPE: PRT
<213> ORGANISM: Artificial sequence
<220> FEATURE:
<223> OTHER INFORMATION: Artificial p2.3 IgG-scFv fusion biparatopic mAb
      with HC C-terminal p1.2-scFv and ADCC/CDC abrogating Fc mutations
      (heavy chain)

<400> SEQUENCE: 280

Asp Val Gln Leu Val Glu Ser Gly Gly Gly Val Val Arg Pro Gly Glu
1               5                   10                  15

Ser Leu Arg Leu Ser Cys Thr Ala Ser Gly Phe Thr Phe Asp Ser Tyr
                20                  25                  30

Gly Met Ser Trp Val Arg Gln Ala Pro Gly Lys Gly Leu Glu Trp Val
            35                  40                  45

Ser Ser Ile Asn Val Gly Asp Asn Thr Tyr Tyr Ala Asp Ser Val Arg
50                  55                  60

Gly Arg Phe Ile Ile Ser Arg Asp Ser Ser Arg Asn Thr Leu Tyr Leu
65                  70                  75                  80

Gln Met Asn Ser Leu Thr Ala Glu Asp Thr Ala Val Tyr Tyr Cys Ala
                85                  90                  95

Asn Trp Asn Ser Phe Phe Asp Tyr Trp Gly Leu Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220
```

```
Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
        435                 440                 445

Gly Ser Gly Gly Gly Gly Ser Glu Ile Val Leu Thr Gln Ser Pro Gly
    450                 455                 460

Thr Val Ser Leu Ser Pro Gly Glu Arg Val Thr Leu Ser Cys Arg Ala
465                 470                 475                 480

Ser Gln Pro Ile Asp Val Tyr Leu Ala Trp Tyr Gln Gln Lys Pro Gly
                485                 490                 495

Gln Ala Pro Arg Leu Leu Ile Tyr Gly Ala Asn Arg Arg Ala Ile Asp
            500                 505                 510

Ile Pro Asp Arg Phe Ser Gly Ser Gly Ser Gly Thr Glu Phe Thr Leu
        515                 520                 525

Thr Ile Asn Ser Leu Gln Asn Glu Asp Phe Ala Val Tyr Phe Cys Gln
    530                 535                 540

Gln Tyr Met Thr Trp Pro Pro Val Thr Phe Gly Gly Gly Thr Lys Val
545                 550                 555                 560

Glu Ile Lys Gly Gln Ser Ser Arg Ser Ser Gly Gly Gly Ser Ser
                565                 570                 575

Gly Gly Gly Gly Ser Asp Val Gln Leu Val Glu Ser Gly Gly Val
            580                 585                 590

Val Arg Pro Gly Glu Ser Leu Arg Leu Ser Cys Ala Ala Ser Gly Phe
        595                 600                 605

Ser Phe Ile Asn Phe Ala Met Thr Trp Val Arg Gln Ala Pro Gly Glu
    610                 615                 620

Gly Pro Glu Trp Val Ser Leu Ile Ser Asp Asp Gly Arg Gly Asn Arg
625                 630                 635                 640
```

```
Pro Tyr Tyr Ala Asp Ser Val Lys Gly Arg Phe Thr Ile Ser Arg Asp
            645                 650                 655

Asn Ser Lys Asn Ile Leu Tyr Leu Gln Met Asn Ser Leu Arg Val Glu
            660                 665                 670

Asp Thr Ala Thr Tyr Tyr Cys Ala Lys Val Ser Trp Asp Val Phe Phe
            675                 680                 685

Asp Tyr Trp Gly Leu Gly Thr Val Val Thr Val Ser Ser
            690                 695                 700
```

<210> SEQ ID NO 281
<211> LENGTH: 215
<212> TYPE: PRT
<213> ORGANISM: Artificial sequence
<220> FEATURE:
<223> OTHER INFORMATION: Artificial p2.3 IgG-scFv fusion biparatopic mAb
      with HC C-terminal p1.2-scFv and ADCC/CDC abrogating Fc mutations
      (light chain (kappa))

<400> SEQUENCE: 281

```
Glu Ile Val Leu Thr Gln Ser Pro Gly Thr Leu Ser Leu Ser Pro Gly
1               5                   10                  15

Glu Ile Ala Thr Leu Ser Cys Arg Ala Ser Gln Asn Val Arg Ser Asp
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215
```

<210> SEQ ID NO 282
<211> LENGTH: 701
<212> TYPE: PRT
<213> ORGANISM: Artificial sequence
<220> FEATURE:
<223> OTHER INFORMATION: Artificial p2.3 IgG-scFv fusion Tie2/VEGF
      bispecific mAb with HC C-terminal VEGF-scFv and ADCC/CDC
      abrogating Fc mutations (heavy chain)

<400> SEQUENCE: 282

```
Asp Val Gln Leu Val Glu Ser Gly Gly Gly Val Val Arg Pro Gly Glu
```

-continued

```
1               5                   10                  15
Ser Leu Arg Leu Ser Cys Thr Ala Ser Gly Phe Thr Phe Asp Ser Tyr
            20                  25                  30
Gly Met Ser Trp Val Arg Gln Ala Pro Gly Lys Gly Leu Glu Trp Val
            35                  40                  45
Ser Ser Ile Asn Val Gly Asp Asn Thr Tyr Tyr Ala Asp Ser Val Arg
 50                  55                  60
Gly Arg Phe Ile Ile Ser Arg Asp Ser Ser Arg Asn Thr Leu Tyr Leu
 65                  70                  75                  80
Gln Met Asn Ser Leu Thr Ala Glu Asp Thr Ala Val Tyr Tyr Cys Ala
            85                  90                  95
Asn Trp Asn Ser Phe Phe Asp Tyr Trp Gly Leu Gly Thr Leu Val Thr
            100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
            130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
            165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
210                 215                 220
Pro Pro Cys Pro Ala Pro Glu Ala Ala Gly Gly Pro Ser Val Phe Leu
225                 230                 235                 240
Phe Pro Pro Lys Pro Lys Asp Thr Leu Met Ile Ser Arg Thr Pro Glu
            245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
            275                 280                 285
Pro Arg Glu Glu Gln Tyr Asn Ser Thr Tyr Arg Val Val Ser Val Leu
            290                 295                 300
Thr Val Leu His Gln Asp Trp Leu Asn Gly Lys Glu Tyr Lys Cys Lys
305                 310                 315                 320
Val Ser Asn Lys Ala Leu Gly Ala Pro Ile Glu Lys Thr Ile Ser Lys
            325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
            405                 410                 415
Gln Gly Asn Val Phe Ser Cys Ser Val Met His Glu Ala Leu His Asn
            420                 425                 430
```

His Tyr Thr Gln Lys Ser Leu Ser Leu Ser Pro Gly Lys Gly Gly
            435                 440                 445

Gly Ser Gly Gly Gly Gly Ser Asp Ile Gln Met Thr Gln Ser Pro Ser
    450                 455                 460

Ser Leu Ser Ala Ser Val Gly Asp Arg Val Thr Ile Thr Cys Arg Ala
465                 470                 475                 480

Ser Gln Val Ile Arg Arg Ser Leu Ala Trp Tyr Gln Gln Lys Pro Gly
                485                 490                 495

Lys Ala Pro Lys Leu Leu Ile Tyr Ala Ala Ser Asn Leu Ala Ser Gly
            500                 505                 510

Val Pro Ser Arg Phe Ser Gly Ser Gly Ser Gly Thr Asp Phe Thr Leu
        515                 520                 525

Thr Ile Ser Ser Leu Gln Pro Glu Asp Phe Ala Thr Tyr Tyr Cys Gln
530                 535                 540

Gln Ser Asn Thr Ser Pro Leu Thr Phe Gly Gln Gly Thr Lys Val Glu
545                 550                 555                 560

Ile Lys Gly Gln Ser Ser Arg Ser Ser Gly Gly Gly Ser Ser Gly
                565                 570                 575

Gly Gly Gly Ser Glu Val Gln Leu Val Glu Ser Gly Gly Leu Val
        580                 585                 590

Gln Pro Gly Gly Ser Leu Arg Leu Ser Cys Ala Ala Ser Gly Phe Ser
        595                 600                 605

Ile Asn Gly Ser Trp Ile Phe Trp Val Arg Gln Ala Pro Gly Lys Gly
        610                 615                 620

Leu Glu Trp Val Gly Ala Ile Trp Pro Phe Gly Gly Tyr Thr His Tyr
625                 630                 635                 640

Ala Asp Ser Val Lys Gly Arg Phe Thr Ile Ser Ala Asp Thr Ser Lys
                645                 650                 655

Asn Thr Ala Tyr Leu Gln Met Asn Ser Leu Arg Ala Glu Asp Thr Ala
            660                 665                 670

Val Tyr Tyr Cys Ala Arg Trp Gly His Ser Thr Ser Pro Trp Ala Met
        675                 680                 685

Asp Tyr Trp Gly Gln Gly Thr Leu Val Thr Val Ser Ser
        690                 695                 700

<210> SEQ ID NO 283
<211> LENGTH: 215
<212> TYPE: PRT
<213> ORGANISM: Artificial sequence
<220> FEATURE:
<223> OTHER INFORMATION: Artificial p2.3 IgG-scFv fusion Tie2/VEGF
      bispecific mAb with HC C-terminal VEGF-scFv and ADCC/CDC
      abrogating Fc mutations (light chain (kappa))

<400> SEQUENCE: 283

Glu Ile Val Leu Thr Gln Ser Pro Gly Thr Leu Ser Leu Ser Pro Gly
1               5                   10                  15

Glu Ile Ala Thr Leu Ser Cys Arg Ala Ser Gln Asn Val Arg Ser Asp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Ser Leu Gln Ser
65                  70                  75                  80

```
Glu Asp Phe Ala Val Tyr Tyr Cys Gln Gln Tyr Ser Asn Trp Pro Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210             215

<210> SEQ ID NO 284
<211> LENGTH: 682
<212> TYPE: PRT
<213> ORGANISM: Artificial sequence
<220> FEATURE:
<223> OTHER INFORMATION: Aflibercept-p2.3 scFv fusion Tie2/VEGF
      bispecific mAb with C-terminal p2.3-scFv

<400> SEQUENCE: 284

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
            130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
            195                 200                 205

His Thr Cys Pro Pro Cys Pro Ala Pro Glu Leu Leu Gly Gly Pro Ser
            210                 215                 220
```

```
Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
            245                 250                 255

Glu Val Lys Phe Asn Trp Tyr Val Asp Gly Val Glu Val His Asn Ala
        260                 265                 270

Lys Thr Lys Pro Arg Glu Glu Gln Tyr Asn Ser Thr Tyr Arg Val Val
    275                 280                 285

Ser Val Leu Thr Val Leu His Gln Asp Trp Leu Asn Gly Lys Glu Tyr
290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Gly
            420                 425                 430

Gly Gly Gly Ser Gly Gly Gly Gly Ser Glu Ile Val Leu Thr Gln Ser
        435                 440                 445

Pro Gly Thr Leu Ser Leu Ser Pro Gly Glu Ile Ala Thr Leu Ser Cys
    450                 455                 460

Arg Ala Ser Gln Asn Val Arg Ser Asp Leu Ala Trp Tyr Gln Gln Lys
465                 470                 475                 480

Pro Gly Gln Ala Pro Arg Leu Leu Ile Tyr Asp Ala Ser Asn Arg Ala
                485                 490                 495

Thr Gly Ile Pro Asp Arg Phe Ser Gly Ser Gly Ser Gly Thr Asp Phe
            500                 505                 510

Thr Leu Thr Ile Ser Ser Leu Gln Ser Glu Asp Phe Ala Val Tyr Tyr
        515                 520                 525

Cys Gln Gln Tyr Ser Asn Trp Pro Pro Leu Thr Phe Gly Gly Gly Thr
530                 535                 540

Lys Val Glu Ile Lys Gly Gln Ser Ser Arg Ser Ser Gly Gly Gly Gly
545                 550                 555                 560

Ser Ser Gly Gly Gly Gly Ser Asp Val Gln Leu Val Glu Ser Gly Gly
                565                 570                 575

Gly Val Val Arg Pro Gly Glu Ser Leu Arg Leu Ser Cys Thr Ala Ser
            580                 585                 590

Gly Phe Thr Phe Asp Ser Tyr Gly Met Ser Trp Val Arg Gln Ala Pro
        595                 600                 605

Gly Lys Gly Leu Glu Trp Val Ser Ser Ile Asn Val Gly Asp Asn Thr
    610                 615                 620

Tyr Tyr Ala Asp Ser Val Arg Gly Arg Phe Ile Ile Ser Arg Asp Ser
625                 630                 635                 640
```

```
Ser Arg Asn Thr Leu Tyr Leu Gln Met Asn Ser Leu Thr Ala Glu Asp
            645                 650                 655

Thr Ala Val Tyr Tyr Cys Ala Asn Trp Asn Ser Phe Phe Asp Tyr Trp
            660                 665                 670

Gly Leu Gly Thr Leu Val Thr Val Ser Ser
        675                 680

<210> SEQ ID NO 285
<211> LENGTH: 682
<212> TYPE: PRT
<213> ORGANISM: Artificial sequence
<220> FEATURE:
<223> OTHER INFORMATION: Aflibercept-p2.3 scFv fusion Tie2/VEGF
      bispecific mAb with C-terminal p2.3-scFv and ADCC/CDC abrogating
      Fc mutations

<400> SEQUENCE: 285

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Ala Ala Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Gly Ala Pro Ile Glu Lys Thr
```

```
                    305                 310                 315                 320
            Ile Ser Lys Ala Lys Gly Gln Pro Arg Glu Pro Gln Val Tyr Thr Leu
                            325                 330                 335

Pro Pro Ser Arg Asp Glu Leu Thr Lys Asn Gln Val Ser Leu Thr Cys
                            340                 345                 350

Leu Val Lys Gly Phe Tyr Pro Ser Asp Ile Ala Val Glu Trp Glu Ser
                            355                 360                 365

Asn Gly Gln Pro Glu Asn Asn Tyr Lys Thr Thr Pro Pro Val Leu Asp
                370                 375                 380

Ser Asp Gly Ser Phe Phe Leu Tyr Ser Lys Leu Thr Val Asp Lys Ser
            385                 390                 395                 400

Arg Trp Gln Gln Gly Asn Val Phe Ser Cys Ser Val Met His Glu Ala
                            405                 410                 415

Leu His Asn His Tyr Thr Gln Lys Ser Leu Ser Leu Ser Pro Gly Gly
                            420                 425                 430

Gly Gly Gly Ser Gly Gly Gly Gly Ser Glu Ile Val Leu Thr Gln Ser
                            435                 440                 445

Pro Gly Thr Leu Ser Leu Ser Pro Gly Glu Ile Ala Thr Leu Ser Cys
                    450                 455                 460

Arg Ala Ser Gln Asn Val Arg Ser Asp Leu Ala Trp Tyr Gln Gln Lys
            465                 470                 475                 480

Pro Gly Gln Ala Pro Arg Leu Leu Ile Tyr Asp Ala Ser Asn Arg Ala
                            485                 490                 495

Thr Gly Ile Pro Asp Arg Phe Ser Gly Ser Gly Ser Gly Thr Asp Phe
                            500                 505                 510

Thr Leu Thr Ile Ser Ser Leu Gln Ser Glu Asp Phe Ala Val Tyr Tyr
                            515                 520                 525

Cys Gln Gln Tyr Ser Asn Trp Pro Pro Leu Thr Phe Gly Gly Gly Thr
                    530                 535                 540

Lys Val Glu Ile Lys Gly Gln Ser Ser Arg Ser Ser Gly Gly Gly Gly
            545                 550                 555                 560

Ser Ser Gly Gly Gly Gly Ser Asp Val Gln Leu Val Glu Ser Gly Gly
                            565                 570                 575

Gly Val Val Arg Pro Gly Glu Ser Leu Arg Leu Ser Cys Thr Ala Ser
                            580                 585                 590

Gly Phe Thr Phe Asp Ser Tyr Gly Met Ser Trp Val Arg Gln Ala Pro
                    595                 600                 605

Gly Lys Gly Leu Glu Trp Val Ser Ser Ile Asn Val Gly Asp Asn Thr
                610                 615                 620

Tyr Tyr Ala Asp Ser Val Arg Gly Arg Phe Ile Ile Ser Arg Asp Ser
            625                 630                 635                 640

Ser Arg Asn Thr Leu Tyr Leu Gln Met Asn Ser Leu Thr Ala Glu Asp
                            645                 650                 655

Thr Ala Val Tyr Tyr Cys Ala Asn Trp Asn Ser Phe Phe Asp Tyr Trp
                            660                 665                 670

Gly Leu Gly Thr Leu Val Thr Val Ser Ser
                    675                 680

<210> SEQ ID NO 286
<211> LENGTH: 696
<212> TYPE: PRT
<213> ORGANISM: Artificial sequence
<220> FEATURE:
<223> OTHER INFORMATION: p2.3-ranibizumab Tie2/VEGF bispecific mAb with
      HC C-terminal ranibizumab-scFv and ADCC/CDC abrogating Fc
``` mutations (heavy chain)

<400> SEQUENCE: 286

Asp Val Gln Leu Val Glu Ser Gly Gly Gly Val Val Arg Pro Gly Glu
1               5                   10                  15

Ser Leu Arg Leu Ser Cys Thr Ala Ser Gly Phe Thr Phe Asp Ser Tyr
            20                  25                  30

Gly Met Ser Trp Val Arg Gln Ala Pro Gly Lys Gly Leu Glu Trp Val
        35                  40                  45

Ser Ser Ile Asn Val Gly Asp Asn Thr Tyr Tyr Ala Asp Ser Val Arg
    50                  55                  60

Gly Arg Phe Ile Ile Ser Arg Asp Ser Ser Arg Asn Thr Leu Tyr Leu
65                  70                  75                  80

Gln Met Asn Ser Leu Thr Ala Glu Asp Thr Ala Val Tyr Tyr Cys Ala
                85                  90                  95

Asn Trp Asn Ser Phe Phe Asp Tyr Trp Gly Leu Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

```
Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
        435                 440                 445

Gly Ser Gly Gly Gly Gly Ser Glu Ile Val Leu Thr Gln Ser Pro Gly
    450                 455                 460

Thr Leu Ser Leu Ser Pro Gly Glu Ile Ala Thr Leu Ser Cys Arg Ala
465                 470                 475                 480

Ser Gln Asn Val Arg Ser Asp Leu Ala Trp Tyr Gln Gln Lys Pro Gly
                485                 490                 495

Gln Ala Pro Arg Leu Leu Ile Tyr Asp Ala Ser Asn Arg Ala Thr Gly
            500                 505                 510

Ile Pro Asp Arg Phe Ser Gly Ser Gly Ser Gly Thr Asp Phe Thr Leu
        515                 520                 525

Thr Ile Ser Ser Leu Gln Ser Glu Asp Phe Ala Val Tyr Tyr Cys Gln
    530                 535                 540

Gln Tyr Ser Asn Trp Pro Pro Leu Thr Phe Gly Gly Gly Thr Lys Val
545                 550                 555                 560

Glu Ile Lys Gly Gln Ser Ser Arg Ser Ser Gly Gly Gly Ser Ser
                565                 570                 575

Gly Gly Gly Gly Ser Asp Val Gln Leu Val Glu Ser Gly Gly Gly Val
            580                 585                 590

Val Arg Pro Gly Glu Ser Leu Arg Leu Ser Cys Thr Ala Ser Gly Phe
        595                 600                 605

Thr Phe Asp Ser Tyr Gly Met Ser Trp Val Arg Gln Ala Pro Gly Lys
    610                 615                 620

Gly Leu Glu Trp Val Ser Ser Ile Asn Val Gly Asp Asn Thr Tyr Tyr
625                 630                 635                 640

Ala Asp Ser Val Arg Gly Arg Phe Ile Ile Ser Arg Asp Ser Ser Arg
                645                 650                 655

Asn Thr Leu Tyr Leu Gln Met Asn Ser Leu Thr Ala Glu Asp Thr Ala
            660                 665                 670

Val Tyr Tyr Cys Ala Asn Trp Asn Ser Phe Phe Asp Tyr Trp Gly Leu
        675                 680                 685

Gly Thr Leu Val Thr Val Ser Ser
    690                 695

<210> SEQ ID NO 287
<211> LENGTH: 215
<212> TYPE: PRT
<213> ORGANISM: Artificial sequence
<220> FEATURE:
<223> OTHER INFORMATION: p2.3-ranibizumab Tie2/VEGF bispecific mAb with
      HC C-terminal ranibizumab-scFv and ADCC/CDC abrogating Fc
      mutations (light chain (kappa))

<400> SEQUENCE: 287

Glu

```
                50                  55                  60
Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Ser Asn Trp Pro Pro
                    85                  90                  95

Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 288
<211> LENGTH: 696
<212> TYPE: PRT
<213> ORGANISM: Artificial sequence
<220> FEATURE:
<223> OTHER INFORMATION: p2.3-ranibizumab Tie2/VEGF bispecific mAb with
      HC N-terminal ranibizumab-scFv and ADCC/CDC abrogating Fc
      mutations (he -continued

```
Phe Ile Ile Ser Arg Asp Ser Arg Asn Thr Leu Tyr Leu Gln Met
        195                 200                 205

Asn Ser Leu Thr Ala Glu Asp Thr Ala Val Tyr Tyr Cys Ala Asn Trp
210                 215                 220

Asn Ser Phe Phe Asp Tyr Trp Gly Leu Gly Thr Leu Val Thr Val Ser
225                 230                 235                 240

Ser Gly Gly Gly Gly Ser Gly Gly Gly Ser Asp Val Gln Leu Val
                245                 250                 255

Glu Ser Gly Gly Gly Val Val Arg Pro Gly Glu Ser Leu Arg Leu Ser
                260                 265                 270

Cys Thr Ala Ser Gly Phe Thr Phe Asp Ser Tyr Gly Met Ser Trp Val
                275                 280                 285

Arg Gln Ala Pro Gly Lys Gly Leu Glu Trp Val Ser Ser Ile Asn Val
            290                 295                 300

Gly Asp Asn Thr Tyr Tyr Ala Asp Ser Val Arg Gly Arg Phe Ile Ile
305                 310                 315                 320

Ser Arg Asp Ser Ser Arg Asn Thr Leu Tyr Leu Gln Met Asn Ser Leu
                325                 330                 335

Thr Ala Glu Asp Thr Ala Val Tyr Tyr Cys Ala Asn Trp Asn Ser Phe
                340                 345                 350

Phe Asp Tyr Trp Gly Leu Gly Thr Leu Val Thr Val Ser Ser Ala Ser
                355                 360                 365

Thr Lys Gly Pro Ser Val Phe Pro Leu Ala Pro Ser Ser Lys Ser Thr
            370                 375                 380

Ser Gly Gly Thr Ala Ala Leu Gly Cys Leu Val Lys Asp Tyr Phe Pro
385                 390                 395                 400

Glu Pro Val Thr Val Ser Trp Asn Ser Gly Ala Leu Thr Ser Gly Val
                405                 410                 415

His Thr Phe Pro Ala Val Leu Gln Ser Ser Gly Leu Tyr Ser Leu Ser
                420                 425                 430

Ser Val Val Thr Val Pro Ser Ser Ser Leu Gly Thr Gln Thr Tyr Ile
            435                 440                 445

Cys Asn Val Asn His Lys Pro Ser Asn Thr Lys Val Asp Lys Lys Val
450                 455                 460

Glu Pro Lys Ser Cys Asp Lys Thr His Thr Cys Pro Pro Cys Pro Ala
465                 470                 475                 480

Pro Glu Ala Ala Gly Gly Pro Ser Val Phe Leu Phe Pro Pro Lys Pro
                485                 490                 495

Lys Asp Thr Leu Met Ile Ser Arg Thr Pro Glu Val Thr Cys Val Val
                500                 505                 510

Val Asp Val Ser His Glu Asp Pro Glu Val Lys Phe Asn Trp Tyr Val
            515                 520                 525

Asp Gly Val Glu Val His Asn Ala Lys Thr Lys Pro Arg Glu Glu Gln
530                 535                 540

Tyr Asn Ser Thr Tyr Arg Val Val Ser Val Leu Thr Val Leu His Gln
545                 550                 555                 560

Asp Trp Leu Asn Gly Lys Glu Tyr Lys Cys Lys Val Ser Asn Lys Ala
                565                 570                 575

Leu Gly Ala Pro Ile Glu Lys Thr Ile Ser Lys Ala Lys Gly Gln Pro
                580                 585                 590

Arg Glu Pro Gln Val Tyr Thr Leu Pro Pro Ser Arg Glu Glu Met Thr
            595                 600                 605
```

-continued

```
Lys Asn Gln Val Ser Leu Thr Cys Leu Val Lys Gly Phe Tyr Pro Ser
    610                 615                 620

Asp Ile Ala Val Glu Trp Glu Ser Asn Gly Gln Pro Glu Asn Asn Tyr
625                 630                 635                 640

Lys Thr Thr Pro Pro Val Leu Asp Ser Asp Gly Ser Phe Phe Leu Tyr
                645                 650                 655

Ser Lys Leu Thr Val Asp Lys Ser Arg Trp Gln Gln Gly Asn Val Phe
            660                 665                 670

Ser Cys Ser Val Met His Glu Ala Leu His Asn His Tyr Thr Gln Lys
        675                 680                 685

Ser Leu Ser Leu Ser Pro Gly Lys
    690                 695
```

<210> SEQ ID NO 289
<211> LENGTH: 215
<212> TYPE: PRT
<213> ORGANISM: Artificial sequence
<220> FEATURE:
<223> OTHER INFORMATION: p2.3-ranibizumab Tie2/VEGF bispecific mAb with
      HC N-terminal ranibizumab-scFv and ADCC/CDC abrogating Fc
      mutations (light chain (kappa))

<400> SEQUENCE: 289

```
Glu Ile Val Leu Thr Gln Ser Pro Gly Thr Leu Ser Leu Ser Pro Gly
1               5                   10                  15

Glu Ile Ala Thr Leu Ser Cys Arg Ala Ser Gln Asn Val Arg Ser Asp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```